(12) United States Patent
Doudna et al.

(10) Patent No.: US 8,852,911 B2
(45) Date of Patent: Oct. 7, 2014

(54) METHOD OF PRODUCING DICER

(75) Inventors: Jennifer A. Doudna, Berkeley, CA (US); Enbo Ma, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/565,453

(22) Filed: Aug. 2, 2012

(65) Prior Publication Data

US 2013/0196383 A1    Aug. 1, 2013

Related U.S. Application Data

(60) Provisional application No. 61/515,135, filed on Aug. 4, 2011, provisional application No. 61/515,647, filed on Aug. 5, 2011.

(51) Int. Cl.

| | |
|---|---|
| *C12N 9/22* | (2006.01) |
| *C12N 15/74* | (2006.01) |
| *C12N 1/20* | (2006.01) |
| *C12N 15/00* | (2006.01) |
| *C12N 15/11* | (2006.01) |
| *C12N 9/16* | (2006.01) |

(52) U.S. Cl.
CPC ................ *C12N 9/16* (2013.01); *C12N 15/111* (2013.01); *C12N 2330/00* (2013.01); *C12N 2310/14* (2013.01); *C12Y 301/26003* (2013.01)
USPC .... 435/199; 435/488; 435/252.33; 435/320.1

(58) Field of Classification Search
None
See application file for complete search history.

(56) References Cited

U.S. PATENT DOCUMENTS

| | | |
|---|---|---|
| 2003/0224432 A1 | 12/2003 | Myers et al. |
| 2007/0031417 A2 | 2/2007 | Mello |
| 2011/0117610 A1 | 5/2011 | Doudna et al. |

FOREIGN PATENT DOCUMENTS

| | | |
|---|---|---|
| WO | WO03/093430 | 12/2003 |
| WO | WO 2009117513 A2 * | 9/2009 |

OTHER PUBLICATIONS

Li T et al. High-Level Expression and Purification of Recombinant SCF Ubiquitin Ligases. 2005. Methods in Enzymology. vol. 398. p. 125-142.*
Takeshita D et al. Homodimeric Structure and Double-stranded RNA Cleavage Activity of the C-terminal RNase III Domain of Human Dicer. 2007. Journal of Molecular Biology. 374. p. 106-120.*
Macrae, et al. "Ribonuclease Revisited: Structural Insights Into Ribonuclease III Family Enzymes", 2007, Current Opinion in Structural Biology, vol. 17, pp. 1-8.
Krol, et al., "Ribonuclease Dicer Cleaves Triplet Repeat Hairpins into Shorter Repeats that Silence Specific Targets", 2007, Molecular Cell, vol. 25, pp. 576-586.
Provost, et al., "Ribonuclease Activity and RNA Binding of Recombinant Human Dicer", 2002, vol. 21, No. 21, pp. 5864-5874.
Zhang, et al., "Human Dicer Preferentially Cleaves dsRNAs at their Termini Without a Requirement for ADP", 2002, EMBO Journal, vol. 21, No. 21, pp. 5875-5885.

* cited by examiner

*Primary Examiner* — David J Steadman
*Assistant Examiner* — Paul Holland
(74) *Attorney, Agent, or Firm* — Paula A. Borden; Kyle A. Gurley; Bozicevic, Field & Francis LLP

(57) ABSTRACT

The present disclosure provides a method for producing a Dicer polypeptide in a prokaryotic host cell. The present disclosure further provides a purified Dicer complex. The present disclosure further provides kits for producing a Dicer polypeptide in a prokaryotic host cell.

21 Claims, 22 Drawing Sheets

Human Dicer 1
GenBank NP_803187
*Homo sapiens*

```
   1  mkspalqpls  maglqlmtpa  sspmgpffgl  pwqqeaihdn  iytprkyqve  lleaaldhnt
  61  ivcintgsgk  tfiavlitke  isyqirgdfs  rngkrtvflv  nsanqvaqqv  savrthsdlk
 121  vgeysnlevn  aswtkerwnq  eftkhqvlim  tcyvainvik  ngylslsdin  llvfdechla
 181  ildhpyreim  klcencpscp  riilgltasil  ngkcdpeele  ekiqklekil  ksnaetatdl
 241  vvldrytsqp  ceivvdcgpf  tdrsglyerl  lmeleeainf  indcnisvhs  kerdstlisk
 301  qiisdcravl  vvlgpwcadk  vagmmvrelq  kylkheqeel  hrkflliftdt  flrkihalce
 361  ehfspasldl  kfvtpkviki  leilrkykpy  erqqfesvew  ynnrnqdnyv  swsdsedde
 421  deeieekekp  etnfpspftn  ilcgiiifver  rytavvinrl  ikeagkqdpe  layissnfit
 481  ghgigknqpr  nkqmeaefrk  qeevlrkfra  hetnlliats  iveegvdipk  cnivvrfdlp
 541  teyrsyvqsk  grarapisny  imladtdkik.  sfeediktyk  aiekilrnkc  sksvdtgetd
 601  idpvmddddv  fppyvlrpdd  ggprvtinta  ighinrycar  lpsdpfthla  pkcrtrelpd
 661  gtfystlylp  insplrasiv  gppmscvrla  ervvalicce  klhkigeldd  hlmpvgketv
 721  kyeeeldlhd  eeetsvpgrp  gstkrrgcyp  kaipecirds  yprpdqpcyl  yvigmvittp
 781  ipdeinfrrr  klyppedttr  cfgiltakpi  pqiphfpvyt  rsgevtisie  lkksgfmlsl
 841  qmlelitrlh  qyifshilrl  ekpalefkpt  dadsaycvip  lnvvndssti  didfkfmedi
 901  eksearigip  stkytketpf  vfkledyqda  viipryrnfd  qphrfyvadv  ytditplskf
 961  pspeyetfae  yyktkynidi  tnlnqplldv  dhtssrinll  tprhlnqkgk  aiplssaekr
1021  kakweslqnk  qilvpeicai  hpipaslwrk  avcipsillyr  lhclltaeel  raqtasdagv
1081  gvrslpadfr  ypnldfgwkk  sidsksfisi  snsssaendn  yckhstivpe  naahgganrt
```

FIG. 9

```
1141 sslenhdqms vncrtlises pgklhvevsa dltainglsy nqnlangsyd lanrdfcqgn
1201 qlnyykqeip vqpttsysiq nlysyenqpg psdectilsn kyldgnanks tsdgspvmav
1261 mpgttdtiqv lkgrmdseqs psigyssrtl gpnpgliiga itlsnasdgf nierlemlgd
1321 sfikhaitty lfctypdahe grlsymrskk vsncnlyrlg kkkglpsrmv vsifdppvnw
1381 lppgyvvnqd ksntdkwekd emtkdcmlan gkidedyeee deeee DexD/H-box

```
  1 mkspalqpls magiqimtpa sspmgpffgl pwqgeaihdn iytprkyqve lleaaldhnt
 61 ivclntgsgk tfiaviltke lsyqirgdfs rngkrtvflv nsanqvaqqv savrthsdlk
121 vgeysnlevn aswtkerwnq eftkhqvlim tcyvalnvlk ngylsisdin llvfdechla
181 ildhpyreim kicencpscp rilgltasil ngkcdpeele ekiqkiekil ksnaetatdl
241 vvldrytsqp ceivvdcgpf tdrsglyerl imeleealnf indcnisvhs kerdstlisk
301 qilsdcravl vvlgpwcadk vagmmvreiq kyikheqeel hrkflilftdt flrkihalce
361 ehfspasldl kfvtpkvikl leilrkykpy erqfesvew ynnrnqdnyv swsdsedde
421 deeieekekp etnfpspftn ilcgiifver rytavvlnrl ikeagkqdpe layissnfit
481 ghgigknqpr nkqmeaefrk qeevlrkfra hetnllliats iveegvdipk cnlvvrfdlp
541 teyrsyvqsk grarapisny imladtdkik sfeedlktyk aiekilrnkc sksvdtgetd
601 idpv
```

SEQ ID NO:2

FIG. 10

Modified Dicer (Δ DEAD)

```
    mddddv fppyvlrpdd ggprvtinta ighinrycar lpsdpfthla pkcrtrelpd
gtfystlyip inspirasiv gppmscvrla ervvalicce klhkigeldd hlmpvgketv
kyeeeldihd eeetsvpgrp gstkrrgcyp kaipeclrds yprpdqpcyl yvigmvlttp
ipdelnfrrr klyppedttr cfgiitakpi pqiphfpvyt rsgevtisie lkksgfmisl
qmielitrih qyifshilri ekpaiefkpt dadsaycvip invvndsstl didfkfmedi
eksearigip stkytketpf vfkled Modified Dicer (K70A)

```
   1  mkspalqpls  maglqlmtpa  sspmpffigl  pwqgeaihdn  iytprkyqve  lleaaldhnt
  61  ivcintgsga  tfiavlitke  lsvqirgdfs  rngkrtvflv  nsarqvaqqv  savrthsdik
 121  vgeysnlevn  aswtkerwnq  eftkhqvlim  tcyvalnvik  ngyislsdin  ilvfdechla
 181  ildhpyreim  kicencpscp  rilgitasil  ngkcdpeele  ekiqklekil  ksnaetatdl
 241  vvldrytsqp  ceivvdcgpf  tdrsglyeri  imeleealnf  indcnisvhs  kerdstlisk
 301  qiisdcravl  vvlgpwcadk  vagmmvrelq  kyikheqeel  hrkfilifdt  firkihalce
 361  ehfspasldl  kfvtpkvikl  leiirkykpy  erqqfesvew  ynrrnqdnyv  swsdsedde
 421  deeieeekp   etnfpspftn  ilcgiifver  rytavinrl   ikeagkqdpe  layissnfit
 481  ghgigknqpr  nkqmeaefrk  qeevirkfra  hetnlliats  iveegvdipk  cnlvvrfdip
 541  teyrsyvqsk  grarapisny  imladtdkik  sfeedlktyk  aiekilrnkc  sksvdtgetd
 601  idpvmdddv   fppyvlrpdd  ggprvtinta  ighinrycar  lpsdpfthla  pkcrtreipd
 661  gtfystlylp  insplrasiv  gppmscvrla  ervvalicce  klhkigeldd  himpvgketv
 721  kyeeeldlhd  eeetsvpgrp  gstkzrqcyp  kaipecirds  yprpdqpcyl  yvigmvittp
 781  lpdeinfrrr  klyppedttr  cfgiitakpi  pqiphfpvyt  rsgevtisie  ikksgfmlsl
 841  qmielitrlh  qyifshilrl  ekpalefkpt  dadsaycvip  lnvvndsstl  didfkfmedi
 901  eksearigip  stkytketpf  vfkiedyqda  viipryrnfd  qphrfyvadv  ytdltpiskf
 961  pspeyetfae  yyktkynidl  tninqplldv  dhtssrinli  tprhincqkg  aiplssaekr
1021  kakweslqnk  qilvpeicai  hpipaslwrk  avclpsilyr  lhciitaeel  raqtasdagv
1081  gvrsipadfr  ypnldfgwkk  sidsksfisi  snsssaendn  yckhstivpe  naahgganrt
1141  ssienhdqms  vncrtlises  pgkihvevsa  ditainglsy  nqniangsyd  lanrdfcqgn
1201  qlnyykqeip  vqptsysiq   nlysyenqpq  psdectiisn  kyldgnanks  tsdgspvmav
1261  mpgttdtiqv  ikgrmdseqs  psigyssrtl  gpnpgliiqa  ltisnasdgf  nlerlemigd
1321  sfikhaitty  ifctypdahe  grlsymrskk  vsncnlyrlg  kkkgipsrmv  vsifdppvnw
1381  lppgyvvnqd  ksntdkwekd  entkdcmlan  gkldedyeee  deeeeslmwr  apkeeadyed
1441  dfieydqehi  rfidnmlmgs  gafvkkisls  pfsttdsaye  wkmpkksslg  smpfssdfed
1501  fdysswdamc  yldpskavee  ddfvvgfwnp  seencgvdtg  kgsisydlht  eqciadksia
1561  dcveallgcy  itscgeraaq  lflcsiglkv  lpvikitdre  kalcptrenf  nsqqknisvs
1621  caaasvassr  ssvlkdseyg  clkipprcmf  dhpdadktln  hlisgfenfe  kkinyrfknk
1681  ayilqaftha  syhyntitdc  yqriefigda  iidylltkhl  yedprqhspg  vitdlrsalv
1741  nntifaslav  kydyhkyfka  vspelfhvid  dfvqfqiekn  emqgmdselr  rseedeekee
1801  dievpkamgd  ifeslagaiy  ndsgmsletv  wqvyypmmrp  liekfsanvp  rspvrellem
1861  epetakfspa  ertydgkvrv  tvevvgkgkf  kgvgrsyria  ksaaarralr  sikanqpqvp
1921  ns
```

(SEQ ID NO:4)

FIG. 12

Dicer amino acid sequence alignment

Sequence 1 : Homo sapiens -- GenBank NP_803187
Sequence 2 : Pan troglodytes -- GenBank XP_001154010
Sequence 3 : Canis familiaris -- GenBank XP_537547
Sequence 4 : Rattus norvegicus -- GenBank XP_001068155
Sequence 5 : Mus musculus -- GenBank EDL18787

```
sequence1    MKSPALQPLSMAGLQLMTPASSPMGPFFGLPWQQEAIHDNIYTPRKYQVELLEAALDHNT    60
sequence2    MKNPALQPLSMAGLQLMTPASSPMGPFFGLPWQQEAIHDNIYTPRKYQVELLEAALDHNT    60
sequence3    MKSPALQPLSMAGLQLMTPASSPMGPFFGLPWQQEAIHDNIYTPRKYQVELLEAALDHNT    60
sequence4    MKSPALQPLSMAGLQLMTPASSPMGPFFGLPWQQEAIHDNIYTPRKYQVELLEAALDHNT    60
sequence5    LKSPALQPLSMAGLQLMTPASSPMGPFFGLPWQQEAIHDNIYTPRKYQVELLEAALDHNT    60
             :*.********************************************************* sequence1    IVCLNTGSGKTFIAVLLTKELSYQIRGDFSRNGKRTVFLVNSANQVAQQVSAVRTHSDLK   120
sequence2    IVCLNTGSGKTFIAVLLTKELSYQIRGDFSRNGKRTVFLVNSANQVAQQVSAVRTHSDLK   120
sequence3    IVCLNTGSGKTFIAVLLTKELSYQIRGDFNRNGKRTVFLVNSANQVAQQVSAVRTHSDLK   120
sequence4    IVCLNTGSGKTFIAVLLTKELAHQIRGDLSPHAKRTVFLVNSANQVAQQVSAVRTHSDLK   120
sequence5    IVCLNTGSGKTFIAVLLTKELAHQIRGDLNPHAKRTVFLVNSANQVAQQVSAVRTHSDLK   120
             *******************: :: .: .*********************** sequence1    VGEYSNLEVNASWTKERWNQEFTKHQVLIMTCYVALNVLKNGYLSLSDINLLVFDECHLA   180
sequence2    VGEYSNLEVNASWTKERWNQEFTKHQVLIMTCYVALNVLKNGYLSLSDINLLVFDECHLA   180
sequence3    VGEYSNLEVNASWTKEKWNQEFTKHQVLVMTCYVALNVLKNGYLSLSDINLLVFDECHLA   180
sequence4    VGEYSNLEVNASWTKERWSQEFTKHQVLIMTCYVALTVLKNGYLSLSDINLLVFDECHLA   180
sequence5    VGEYSDLEVNASWTKERWSQEFTKHQVLIMTCYVALTVLKNGYLSLSDINLLVFDECHLA   180
             *****:**********:**.********:******.************************
```

FIG. 13A

```
sequence1      ILDHPYREIMKLCENCPSCPRILGLTASILNGKCDPEELEEKIQKLEKILKSNAETATDL 240
sequence2      ILDHPYREIMKLCENCPSCPRILGLTASILNGKCDPEELEEKIQKLEKILKSNAETATDL 240
sequence3      ILDHPYREIMKLCENCPSCPRILGLTASILNGKCDPEELEEKIQKLEKILKSNAETATDL 240
sequence4      ILDHPYREIMKLCDSCPSCPRILGLTASILNGKCDPDELEEKIQKLEKILKSGAETATDL 240
sequence5      ILDHPYREIMKLCESCPSCPRILGLTASILNGKCDPEELEEKIQKLERILRSDAETATDL 240
               ********** .******************** ********* *.****** sequence1      VVLDRYTSQPCEIVVDCGPFTDRSGLYERLLMELEEALNFINDCNISVHSKERDSTLISK 300
sequence2      VVLDRYTSQPCEIVVDCGPFTDRSGLYERLLMELEEALNFINDCNISVHSKERDSTLISK 300
sequence3      VVLDRYTSQPCEIVVDCGPFTDRSGLYERLLVELEEALNFINDCNISVHSKERDSTLISK 300
sequence4      VVLDRYTSQPCEIVVDCGPFTDRSGLYGRLLVELEEALNFINDCNVSVHSKERDSTLISK 300
sequence5      VVLDRYTSQPCEIVVDCGPFTDRSGLYERLLMELEEALDFINDCNVAVHSKERDSTLISK 300
               ************************* *:****:*: *********** sequence1      QILSDCRAVLVVLGPWCADKVAGMMVRELQKYIKHEQEELHRKFLLFTDTFLRKIHALCE 360
sequence2      QILSDCRAVLVVLGPWCADKVAGMMVRELQKYIKHEQEELHRKFLLFTDTFLRKIHALCE 360
sequence3      QILSDCRAVLVVLGPWCADKVAGMMVRELQKYIKHEQEELHRKFLLFTDTFLRKIHALCE 360
sequence4      QILSDCRAVLVVLGPWCADKVAGMMVRELQKYIKHEQEELHRKFLLFTDTLLRKIHALCE 360
sequence5      QILSDCRAVLVVLGPWCADKVAGMMVRELQKYIKHEQEELHRKFLLFTDTLLRKIHALCE 360
               ***********************************************:******* sequence1      EHFSPASLDLKFVTPKVIKLLEILRKYKPYERQQFESVEWYNNRNQDNYVSWSDSEDDDE 420
sequence2      EHFSPASLDLKFVTPKVIKLLEILRKYKPYERQQFESVEWYNNRNQDNYVSWSDSEDDDE 420
sequence3      EHFSPASLDLKFVTPKVIKLLEILRKYKPYERQQFESVEWYNNRNQDNYVSWSDSEDDDE 420
sequence4      EYFSPASLDLKFVTPKVMKLLEILRKYKPYERQQFESVEWYNNRNQDNYVSWSDSEDDDD 420
sequence5      EYFSPASLDLKYVTPKVMKLLEILRKYKPYERQQFESVEWYNNRNQDNYVSWSDSEDDDD 420
               *:*********:*****:******************************************:
```

FIG. 13B

```
sequence1    DEEIEEKEKPETNFPSPFTNILCGIIFVERRYTAVVLNRLIKEAGKQDPELAYISSNFIT  480
sequence2    DEEIEEKEKPETNFPSPFTNILCGIIFVERRYTAVVLNRLIKEAGKQDPELAYISSNFIT  480
sequence3    DEEIEEKEKPETNFPSPFTNILCGIIFVERRYTAVVLNRLIKEAGKQDPELAYISSNFIT  480
sequence4    DEEIEEKEKPETNFPSPFTNILCGIIFVERRYTAVVLNRLIKEAGKQDPELAYISSNFIT  480
sequence5    DEEIEEKEKPETNFPSPFTNILCGIIFVERRYTAVVLNRLIKEAGKQDPELAYISSNFIT  480
             ************************************************************ sequence1    GHGIGKNQPRNKQMEAEFRKQEEVLRKFRAHETNLLIATSIVEEGVDIPKCNLVVRFDLP  540
sequence2    GHGIGKNQPRNKQMEAEFRKQEEVLRKFRAHETNLLIATSIVEEGVDIPKCNLVVRFDLP  540
sequence3    GHGIGKNQPRNKQMEAEFRKQEEVLRKFRAHETNLLIATSIVEEGVDIPKCNLVVRFDLP  540
sequence4    GHGIGKNQPRSKQMEAEFRKQEEVLRKFRAHETNLLIATSVVEEGVDIPKCNLVVRFDLP  540
sequence5    GHGIGKNQPRSKQMEAEFRKQEEVLRKFRAHETNLLIATSVVEEGVDIPKCNLVVRFDLP  540
             ********.*********************** ***************** sequence1    TEYRSYVQSKGRARAPISNYIMLADTDKIKSFEEDLKTYKAIEKILRNKCSKSVDTGETD  600
sequence2    TEYRSYVQSKGRARAPISNYIMLADTDKIKSFEEDLKTYKAIEKILRNKCSKSVDTGETD  600
sequence3    TEYRSYVQSKGRARAPISNYIMLADTDKIKSFEEDLKTYKAIEKILRNKCSKSVDTGEID  600
sequence4    TEYRSYVQSKGRARAPISNYVMLADTDKIKSFEEDLKTYKAIEKILRNKCSKSVDGAEAD  600
sequence5    TEYRSYVQSKGRARAPISNYVMLADTDKIKSFEEDLKTYKAIEKILRNKCSKSADGAEAD  600
             ******************:*******************************..: * sequence1    IDPVMDDDDVFPPYVLRPDDGGPRVTINTAIGHINRYCARLPSDPFTHLAPKCRTRELPD  660
sequence2    IDPVMDDDDVFPPYVLRPDDGGPRVTINTAIGHINRYCARLPSDPFTHLAPKCRTRELPD  660
sequence3    IEPVVDDDDVFPPYVLRPDDGGPRVTINTAIGHINRYCARLPSDPFTHLAPKCRTRELPD  660
sequence4    VHAVVDDDDAFPPYVLRPDDGGPRVTINTAIGHINRYCARLPSDPFTHLAPKCRTRELPD  660
sequence5    VHAGVDDEDAFPPYVLRPDDGGPRVTINTAIGHINRYCARLPSDPFTHLAPKCRTRELPD  660
             :..  **:** *************************************************
```

FIG. 13C

```
sequence1      GTFYSTLYLPINSPLRASIVGPPMSCVRLAERVVALICCEKLHKIGELDDHLMPVGKETV  720
sequence2      GTFYSTLYLPINSPLRASIVGPPMSCVRLAERVVALICCEKLHKIGELDDHLMPVGKETV  720
sequence3      GTFYSTLYLPINSPLRASIVGPPMSCVRLAERVVALICCEKLHKIGELDDHLMPVGKETV  720
sequence4      GTFYSTLYLPINSPLRASIVGPPMGCVRLAERVVALICCEKLHKIGELDEHLMPVGKETV  720
sequence5      GTFYSTLYLPINSPLRASIVGPPMDSVRLAERVVALICCEKLHKIGELDEHLMPVGKETV  720
                                       ****.***************:****** sequence1      KYEEELDLHDEEETSVPGRPGSTKRRQCYPKAIPECLRDSYPRPDQPCYLYVIGMVLTTP  780
sequence2      KYEEELDLHDEEETSVPGRPGSTKRRQCYPKAIPECLRDSYPRPDQPCYLYVIGMVLTTP  780
sequence3      KYEEELDLHDEEETSVPGRPGSTKRRQCYPKAIPECLRDSYPKPDQPCYLYVIGMVLTTP  780
sequence4      KYEEELDLHDEEETSVPGRPGSTKRRQCYPKAIPECLRESYPKPDQPCYLYVIGMVLTTP  780
sequence5      KYEEELDLHDEEETSVPGRPGSTKRRQCYPKAIPECLRESYPKPDQPCYLYVIGMVLTTP  780
                                       ********************:.*:***************** sequence1      LPDELNFRRRKLYPPEDTTRCFGILTAKPIPQIPHFPVYTRSGEVTISIELKKSGFMLSL  840
sequence2      LPDELNFRRRKLYPPEDTTRCFGILTAKPIPQIPHFPVYTRSGEVTISIELKKSGFMLSL  840
sequence3      LPDELNFRRRKLYPPEDTTRCFGILTAKPIPQIPHFPVYTRSGEVTISIELKKSGFTLSL  840
sequence4      LPDELNFRRRKLYPPEDTTRCFGILTAKPIPQIPHFPVYTRSGEVTISIELKKSGFTLSQ  840
sequence5      LPDELNFRRRKLYPPEDTTRCFGILTAKPIPQIPHFPVYTRSGEVTISIELKKSGFTLSQ  840
                                       *****************************************:* sequence1      QMLELITRLHQYIFSHIILRLEKPALEFKPTDADSAYCVLPLNVVNDSSTLDIDFKFMEDI  900
sequence2      QMLELITRLHQYIFSHIILRLEKPALEFKPTDADSAYCVLPLNVVNDSSTLDIDFKFMEDI  900
sequence3      QMLELITRLHQYIFSHIILRLEKPALEFKPTDADSAYCVLPLNVVNDSSTLDIDFKFMEDI  900
sequence4      QMLELVTRLHQYIFSHIILRLEKPALEFQPAGAESAYCVLPLNVVNDSSTLDIDFKFMEDI  900
sequence5      QMLELITRLHQYIFSHIILRLEKPALEFKPTGAESAYCVLPLNVVNDSGTLDIDFKFMEDI  900
                                       *****:**********************:.: .**************.***********
```

FIG. 13D

```
sequence1      EKSEARIGIPSTKYTKETPFVFKLEDYQDAVIIPRYRNFDQPHRFYVADVYTDLTPLSKF  960
sequence2      EKSEARIGIPSTKYTKETPFVFKLEDYQDAVIIPRYRNFDQPHRFYVADVYTDLTPLSKF  960
sequence3      EKSEARIGIPSTKYSKETPFVFKLEDYQDAVIIPRYRNFDQPHRFYVADVYTDLTPLSKF  960
sequence4      EKSEARIGIPSTKYSKETPFVFKLEDYQDAVIIPRYRNFDQPHRFYVADVYTDLTPLSKF  960
sequence5      EKSEARIGIPSTKYSKETPFVFKLEDYQDAVIIPRYRNFDQPHRFYVADVYTDLTPLSKF  960
               ************ ****************************************** sequence1      PSPEYETFAEYYKTKYNLDLTNLNQPLLDVDHTSSRLNLLTPRHLNQKGKALPLSSAEKR  1020
sequence2      PSPEYETFAEYYKTKYNLDLTNLNQPLLDVDHTSSRLNLLTPRHLNQKGKALPLSSAEKR  1020
sequence3      PSPEYETFAEYYKTKYNLDLTNLNQPLLDVDHTSSRLNLLTPRHLNQKGKALPLSSAEKR  1020
sequence4      PSPEYETFAEYYKTKYNLDLTNLNQPLLDVDHTSSRLNLLTPRHLNQKGKALPLSSAEKR  1020
sequence5      PSPEYETFAEYYKTKYNLDLTNLNQPLLDVDHTSSRLNLLTPRHLNQKGKALPLSSAEKR  1020
               ************************************************************ sequence1      KAKWESLQNKQILVPELCAIHPIPASLWRKAVCLPSILYRLHCLLTAEELRAQTASDAGV  1080
sequence2      KAKWESLQNKQILVPELCAIHPIPASLWRKAVCLPSILYRLHCLLTAEELRAQTASDAGV  1080
sequence3      KAKWESLQNKQILVPELCAIHPIPASLWRKAVCLPSILYRLHCLLTAEELRAQTASDAGV  1080
sequence4      KAKWESLQNKQILVPELCAIHPIPASLWRKAVCLPSILYRLHCLLTAEELRAQTASDAGV  1080
sequence5      KAKWESLQNKQILVPELCAIHPIPASLWRKAVCLPSILYRLHCLLTAEELRAQTASDAGV  1080
               ************************************************************ sequence1      GVRSLPADFRYPNLDFGWKKSIDSKSFISISNSSSAENDNYCKHSTIVP-ENAAHQGANR  1139
sequence2      GVRSLPADFRYPNLDFGWKKSIDSKSFISISNSSSAENDNYCKHSTIVP-ENAAHQGANR  1139
sequence3      GVRSLPVDFRYPNLDFGWKKSIDSKSFISVANSSSAENENYCKHSTIVVPENAARQGANR  1140
sequence4      GVRSLPVDFRYPNLDFGWKKSIDSKSFISTCNSSLAESDNYCKHSTTVVPENAAHQGATR  1140
sequence5      GVRSLPVDFRYPNLDFGWKKSIDSKSFISSCNSSLAESDNYCKHSTTVVPEHAAHQGATR  1140
               ****** *********************  *** *:.:***:**: *  ***: ***.*
```

FIG. 13E

```
sequence1  TSSLENHDQMSVNCRTLLSESPGKLHVEVSADLTAINGLSYNQNLANGSYDLANRDFCQG  1199
sequence2  TSSLENHDQMSVNCRTLLSESPGKLHVEVSADLTAINGLSYNQNLANGSYDLANRDFCQG  1199
sequence3  TSSLENHDQMSVNCRTLFSESPGKLQIEVVTDLTAINGLSYNKNLANGSYDLANRDFCQG  1200
sequence4  P-SLENHDQMSVNCKRLPAESPAKLQSEVSVDLTAINGLSYNKSLANGSYDLVNRDFCQG  1199
sequence5  P-SLENHDQMSVNCKRLPAESPAKLQSEVSTDLTAINGLSYNKNLANGSYDLVNRDFCQG  1199
            *******: *:.***:*:.:*:. ***.*:****** sequence1  NQLNYYKQEIPVQPTTSYSIQNLYSYENQPQPSDECTLLSNKYLDGNANKSTSDGSPVMA  1259
sequence2  NQLNYYKQEIPVQPTTSYSIQNLYSYENQPQPSDECTLLSNKYLDGNANKSTSDGSPVMA  1259
sequence3  NQLNYYKQEIPVQPTTSYSIQNLYSYENQPQPSDECTLLSNKYLDGNANKSTSDGSPVMA  1259
sequence4  NQLTYFKQEIPVQPTTSYPIQNLYNYENQPKPSDECTLLSNKYLDGNANKSTSDGSPTTA  1260
sequence5  NQLNYFKQEIPVQPTTSYPIQNLYNYENQPTPSNECPLLSNKYLDGNANTSTSDGSPAGS  1259
           ***.*:************ ***** *****.**:** ***********.******..  .

sequence1  VMPGTTDTIQVLKGRMDSEQSPSIGYSSRTLGPNPGLIIQALTLSNASDGFNLERLEMLG  1319
sequence2  VMPGTTDTIQVLKGRMDSEQSPSIGYSSRTLGPNPGLIIQALTLSNASDGFNLERLEMLG  1319
sequence3  AMPGTTEAVRALKDKMGSEQSPCPGYSSRTLGPNPGLIIQALTLSNASDGFNLERLEMLG  1320
sequence4  PRPAMMTAVEALEGRTDSEQSPSVGHSSRTLGPNPGLIIQALTLSNASDGFNLERLEMLG  1319
sequence5  TMPAMMNAVKALKDRMDSEQSVGYSSPSVGYSSRTLGPNPGLIIQALTLSNASDGFNLERLEMLG  1319
            :*. :   .   .:  :***  .* ****************************** sequence1  DSFLKHAITTYLFCTYPDAHEGRLSYMRSKKVSNCNLYRLGKKKGLPSRMVVSIFDPPVN  1379
sequence2  DSFLKHAITTYLFCTYPDAHEGRLSYMRSKKVSNCNLYRLGKKKGLPSRMVVSIFDPPVN  1379
sequence3  DSFLKHAITTYLFCTYPDAHEGRLSYMRSKKVSNCNLYRLGKKKGLPSRMVVSIFDPPVN  1380
sequence4  DSFLKHAITTYLFCTYPDAHEGRLSYMRSKKVSNCNLYRLGKKQGLPSRMVVSIFDPPVN  1379
sequence5  DSFLKHAITTYLFCTYPDAHEGRLSYMRSKKVSNCNLYRLGKKKGLPSRMVVSIFDPPVN  1379
           *******************************************:***************
```

FIG. 13F

```
sequence1    WLPPGYVVNQDKSNTDKWEKDEMTKDCMLANGKLDEDYEEEDEEEESLMWRAPKEEADYE  1439
sequence2    WLPPGYVVNQDKSNTDKWEKDEMTKDCMLANGKLDEDYEEEDEEEESLMWRAPKEEADYE  1439
sequence3    WLPPGYVVNQDKSNADKWEKDEMTKDCMLANGKLDEDFEEDEEEEDLMWRAPKEDADYE   1440
sequence4    WLPPGYVVNQDKSNSEKWEKDEMTKDCLLANGKLGEDCE--EEEEELAWRAPKEEAEYE   1437
sequence5    WLPPGYVVNQDKSNSEKWEKDEMTKDCLLANGKLGEACE--EEE--DLTWRAPKEEAEDE  1435
             ************ :********:***  * :   *     ***** * sequence1    DDFLEYDQEHIRFIDNMLMGSSGAFVKKISLSPFSTTDSAYEWKMPKKSSLGSMPFSSDFE  1499
sequence2    DDFLEYDQEHIRFIDNMLMGSSGAFVKKISLSPFSTTDSAYEWKMPKKSSLGSMPFSSDFE  1499
sequence3    DDFLEYDQEHIKFIDNMLMGSSGAFVKKISLSPFSTTDSAYEWKMPKKSSLGSMPFSSDFE  1500
sequence4    DDLLEYDQEHIQFIDSMLMGSSGAFVKKIPLSPFSTSDSAYEWKMPKKASLGSVPFSSDLE  1497
sequence5    DDFLEYDQEHIQFIDSMLMGSSGAFVRKISLSPFSASDSAYEWKMPKKASLGSMPFASGLE  1495
              **** *.*******:  *** :*******:::. * sequence1    DFDYSSWDAMCYLDPSKAVEEDDFVVGFWNPSEENCGVDTGKQSISYDLHTEQCIADKSI  1559
sequence2    DFDYSSWDAMCYLDPSKAVEEDDFVVGFWNPSEENCGVDTGKQSISYDLHTEQCIADKSI  1559
sequence3    DFDYSSWDAMCYLDPSKAVEEDDFVVGFWNPSEENCGVDTGKQSISYDLHTEQCIADKSI  1560
sequence4    DFDYSSWDAMCYLDPSKAVEEDDFVVGFWNPSEENCGVDTGKQSISYDLHTEQCIADKSI  1557
sequence5    DFDYSSWDAMCYLDPSKAVEEDDFVVGFWNPSEENCGVDTGKQSISYDLHTEQCIADKSI  1555
             *********************************************************** sequence1    ADCVEALLGCYLTSCGERAAQLFLCSLGLKVLPVIKRTDREKALCPTRENFNSQQKNLSV  1619
sequence2    ADCVEALLGCYLTSCGERAAQLFLCSLGLKVLPVIKRTDREKALCPTRENFNSQQKNLSV  1619
sequence3    ADCVEALLGCYLTSCGERAAQLFLCSLGLKVLPVIKRTDREKALCPTRENFSSQQKNLSG  1620
sequence4    ADCVEALLGCYLTSCGERAAQLFLCSLGLKVLPVMKRTDREKTMCPPRENFSSQQKSPSG  1617
sequence5    ADCVEALLGCYLTSCGERAAQLFLCSLGLKVLPVIKRTSRDKASYPAQENSSSQQKSPSG  1615
             **********************************:***. :**   .:**.*****. . 
```

FIG. 13G

```
sequence1    SCAAASVASSRSSVLKDSEYGCLKIPPRCMFDHPDADKTLNHLISGFENFEKKINYRFKN   1679
sequence2    SCAAASVASSRSSVLKDSEYGCLKIPPRCMFDHPDADKTLNHLISGFENFEKKINYRFKN   1679
sequence3    GRAAASVASLRPSVLKDLEYGCLKIPPRCMFDHPDADKTLNHLISGFENFEKKINYRFKN   1680
sequence4    SCAAA--VSPRSSAGKDLEYGCLKIPPRCMFDHPDAEKTLNHLISGFENFEKKINYIFKN   1675
sequence5    SCASP--VGPRSSAGKDLEYGCLKIPPRCMFDHPDAEKTLNHLISGFETFEKKINYRFKN   1673
                   *:    *   **********:********* :***:* sequence1    KAYLLQAFTHASYHYNTITDCYQRLEFLGDAILDYLITKHLYEDPRQHSPGVLTDLRSAL   1739
sequence2    KAYLLQAFTHASYHYNTITDCYQRLEFLGDAILDYLITKHLYEDPRQHSPGVLTDLRSAL   1739
sequence3    KAYLLQAFTHASYHYNTITDCYQRLEFLGDAILDYLITKHLYEDPRQHSPGVLTDLRSAL   1740
sequence4    KAYLLQAFTHASYHYNTITDCYQRLEFLGDAILDYLITKHLYEDPRQHSPGVLTDLRSAL   1735
sequence5    KAYLLQAFTHASYHYNTITDCYQRLEFLGDAILDYLITKHLYEDPRQHSPGVLTDLRSAL   1733
             ************************************************************ sequence1    VNNTIFASLAVKYDYHKYFKAVSPELFHVIDDFVQFQLEKNEMQGMDSELRRSEEDEEKE   1799
sequence2    VNNTIFASLAVKYDYHKYFKAVSPELFHVIDDFVQFQLEKNEMQGMDSELRRSEEDEEKE   1799
sequence3    VNNTIFASLAVKYDYHKYFKAVSPELFHVIDDFVQFQLEKNEMQGMDSELRRSEEDEEKE   1800
sequence4    VNNTIFASLAVKYDYHKYFKAVSPELFHVIDDFVQFQLEKNEMQGMDSELRRSEEDEEKE   1795
sequence5    VNNTIFASLAVKYDYHKYFKAVSPELFHVIDDFVKFQLEKNEMQGMDSELRRSEEDEEKE   1793
             ********************************:*********************** sequence1    EDIEVPKAMGDIFESLAGAIYMDSGMSLETVWQVYYPMMRPLIEKFSANVPRSPVRELLE   1859
sequence2    EDIEVPKAMGDIFESLAGAIYMDSGMSLETVWQVYYPMMRPLIEKFSANVPRSPVRELLE   1859
sequence3    EDIEVPKAMGDIFESLAGAIYMDSGMSLEMVWQVYYPMMRPLIEKFSANVPRSPVRELLE   1860
sequence4    EDIEVPKAMGDIFESLAGAIYMDSGMSLEVVWQVYYPMMRPLIEKFSANVPRSPVRELLE   1855
sequence5    EDIEVPKAMGDIFESLAGAIYMDSGMSLEVVWQVYPMMQPLIEKFSANVPRSPVRELLE   1853
             *****************************: ***:** **:******************
```

FIG. 13H

```
sequence1    MEPETAKFSPAERTYDGKVRVRTVEVVGKGKFKGVGRSYRIAKSAAARRALRSLKANQPQV  1919
sequence2    MEPETAKFSPAERTYDGKVRVRTVEVVGKGKFKGVGRSYRIAKSAAARRALRSLKANQPQL  1919
sequence3    MEPETAKFSPAERTYDGKVRVRTVEVVGKGKFKGVGRSYRIAKSAAARRALRSLKANQPQV  1920
sequence4    MEPETAKFSPAERTYDGKVRVRTVEVVGKGKFKGVGRSYRIAKSAAARRALRSLKANQPLV  1915
sequence5    MEPETAKFSPAERTYDGKVRVRTVEVVGKGKFKGVGRSYRIAKSAAARRALRSLKANQPQV  1913
             ************************************************************ ::

sequence1    PNS---------  1922
sequence2    WVSLALPSTYQ   1930
sequence3    PNS---------  1923
sequence4    PNS---------  1918
sequence5    PNS---------  1916
              *
```

METHOD OF PRODUCING DICER

CROSS-REFERENCE

This application claims the benefit of U.S. Provisional Patent Application Nos. 61/515,135, filed Aug. 4, 2011, and 61/515,647, filed Aug. 5, 2011, which applications are incorporated herein by reference in their entirety.

STATEMENT REGARDING FEDERALLY SPONSORED RESEARCH

This invention was made with government support under Grant No. R01 GM073794-05 awarded by the National Institutes of Health. The government has certain rights in the invention.

BACKGROUND

RNA interference (RNAi) and related pathways trigger post-transcriptional gene silencing using single-stranded guide RNAs that base pair with cognate mRNAs to direct their endonucleolytic cleavage or translational repression by RNA-induced silencing complexes (RISCs). Silencing is initiated by long dsRNAs or RNA hairpins, which are processed by the endonuclease Dicer to yield 21-23 nt short interfering RNAs (siRNAs) or microRNAs (miRNAs), respectively. These small interfering dsRNAs are then loaded onto Argonaute2 (Ago2), the endonuclease component of RISC.

The eukaryotic endoribonuclease Dicer recognizes distinct types of double-stranded RNA (dsRNA) substrates and generates ~21 base pair products that assemble into RISCs. In humans, Dicer plays a central role in producing most of the small regulatory RNAs that enter this pathway in the cytoplasm. Structural analysis of *Giardia* Dicer and biochemical studies of human Dicer (hDicer) suggest that the enzyme functions as a monomer to bind, orient and cleave dsRNA substrates using a two-metal-ion mechanism similar to that of bacterial Ribonuclease III.

Although mammalian Dicer has been successfully produced recombinantly in eukaryotic cells, recombinant production of mammalian Dicer in prokaryotic cells has proved challenging.

LITERATURE

US Patent Publication No. 2011/0117610; U.S. Patent Publication No. 2007/0031417; U.S. Patent Publication No. 2003/0224432; WO 03/093430; MacRae and Doudna (2007) *Curr. Opin. Struct. Biol.* 17:138.

SUMMARY

The present disclosure provides a method for producing a Dicer polypeptide in a prokaryotic host cell. The present disclosure further provides a purified Dicer complex. The present disclosure further provides kits for producing a Dicer polypeptide in a prokaryotic host cell.

BRIEF DESCRIPTION OF THE DRAWINGS

FIG. 9 depicts the amino acid sequence of a wild-type human Dicer polypeptide (SEQ ID NO:1).

FIG. 10 depicts an amino acid sequence of a DExD/H-box domain (SEQ ID NO:2).

FIG. 11 depicts the amino acid sequence of a Dicer polypeptide that lacks a DExD/H-box domain (SEQ ID NO:3).

FIG. 12 depicts the amino acid sequence of a Dicer polypeptide that has a single amino acid substitution in the DExD/H-box domain (SEQ ID NO:4).

FIGS. 13A-I depict an amino acid sequence alignment of Dicer polypeptides from various mammalian species. Sequence 1: SEQ ID NO:1; Sequence 2: SEQ ID NO:5; Sequence 3: SEQ ID NO:6; Sequence 4: SEQ ID NO:7; Sequence 5: SEQ ID NO:8.

DEFINITIONS

Figure 1:
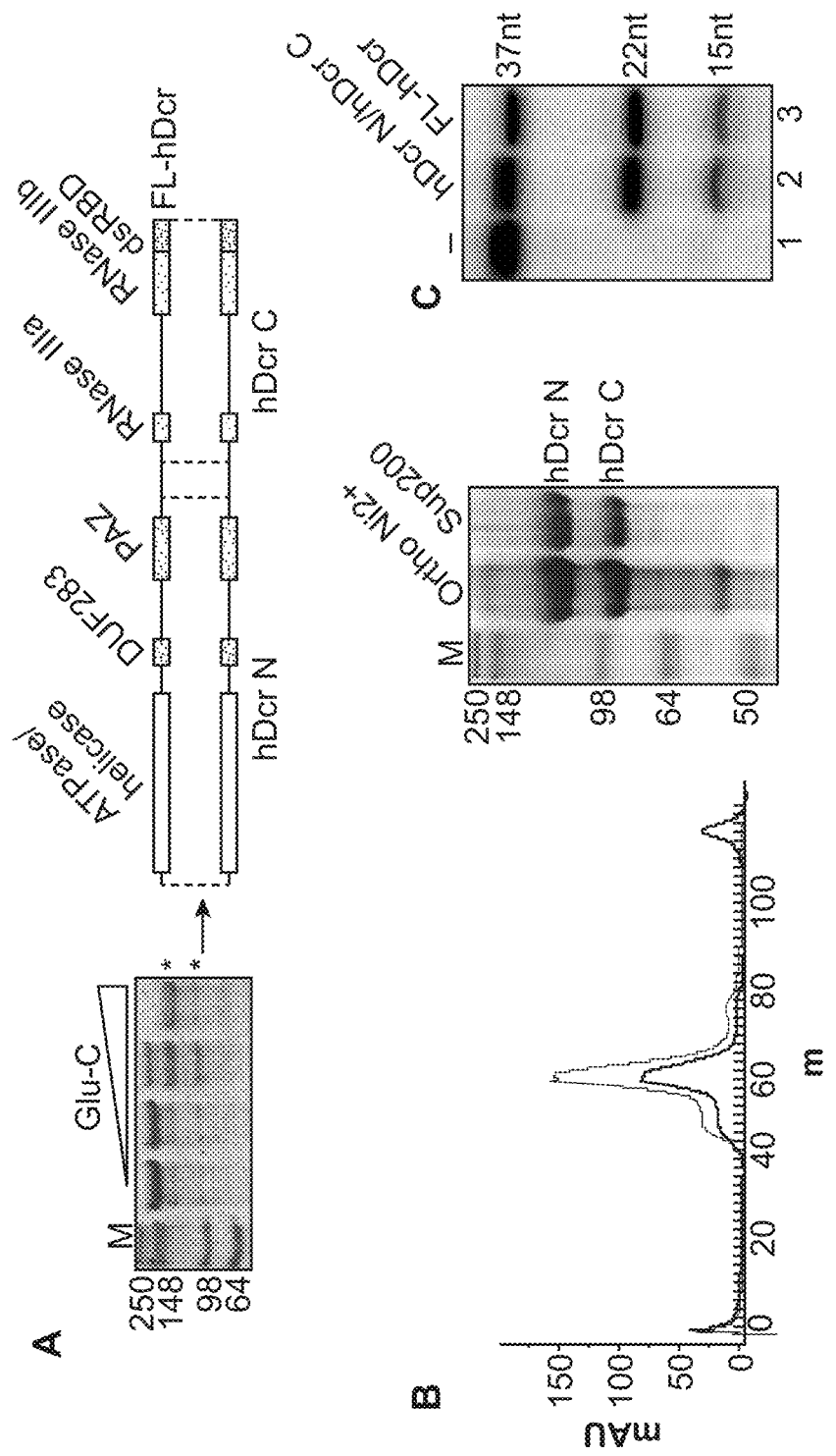
FIGS. 1A-C depict interaction of functional fragments of human Dicer (hDcr).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' terminus and a translation stop codon at the 3' terminus. A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule or between two separate RNA molecules. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

MicroRNAs (miRNAs) are encoded by genes, which encode transcripts containing short double-stranded RNA hairpins. mRNAs are transcribed as longer precursors, termed pre-miRNAs, which can be 50 to 80 nucleotides in length, and which are sometimes found in clusters and frequently found in introns. Upon transcription, miRNAs undergo nuclear cleavage by an RNase III endonuclease, producing the 60-70-nt stem-loop precursor miRNA (pre-miRNA) with a 5' phosphate and a 2-nt 3 overhang. The pre-miRNAs are cleaved by Dicer about two helical turns away from the ends of the pre-miRNA stem loop, producing double-stranded RNA with strands that are approximately the same length (21 to 24 nucleotides), and possess the characteristic 5'-phosphate and 3'-hydroxyl termini. One of the strands of this short-lived intermediate accumulates as the mature miRNA and is subsequently incorporated into a ribonucleoprotein complex, the miRNP. mRNAs interact with target RNAs at specific sites to induce cleavage of the message or inhibit translation.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

The term "heterologous," as used herein in the context of a genetically modified host cell, refers to a polypeptide wherein at least one of the following is true: (a) the polypeptide is foreign ("exogenous") to (i.e., not naturally found in) the host cell; (b) the polypeptide is naturally found in (e.g., is "endogenous to") a given host microorganism or host cell but is either produced in an unnatural (e.g., greater than expected or greater than naturally found) amount in the cell, or differs in nucleotide sequence from the endogenous nucleotide sequence such that the same encoded protein (having the same or substantially the same amino acid sequence) as found endogenously is produced in an unnatural (e.g., greater than expected or greater than naturally found) amount in the cell.

The term "heterologous," as used herein in the context of a chimeric polypeptide, refers to two components that are defined by structures derived from different sources. For example, where "heterologous" is used in the context of a chimeric polypeptide (e.g., a chimeric Dicer enzyme), the chimeric polypeptide includes operably linked amino acid sequences that can be derived from different polypeptides (e.g., a first amino acid sequence from Dicer enzyme; and a second amino acid sequence other than a Dicer enzyme). Similarly, "heterologous" in the context of a polynucleotide encoding a chimeric polypeptide includes operably linked nucleotide sequences that can be derived from different coding regions (e.g., a first nucleotide sequence encoding a Dicer enzyme; and a second nucleotide sequence encoding a polypeptide other than a Dicer enzyme).

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a Dicer polypeptide" includes a plurality of such polypeptides and reference to "the Dicer complex" includes reference to one or more Dicer complexes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method for producing a Dicer polypeptide in a prokaryotic host cell. The present disclosure further provides a purified Dicer complex. The present disclosure further provides kits for producing a Dicer polypeptide in a prokaryotic host cell.

Methods for Producing a Dicer Polypeptide

The present disclosure provides a method for producing a Dicer polypeptide in a prokaryotic host cell. The methods generally involve expressing a first Dicer polypeptide in a prokaryotic host cell, where the first Dicer polypeptide comprises a DUF and a PAZ domain, and either expressing a second Dicer polypeptide in the same prokaryotic host cell or in a separate prokaryotic host cell, where the second Dicer polypeptide comprises an RNAse IIIA domain, an RNase IIIb domain, and a double-stranded RNA binding domain (dsRBD), or where the second Dicer polypeptide comprises an RNAse IIIA domain, an RNAse IIIb domain, and lacks a functional dsRBD. The first Dicer polypeptide and the second Dicer polypeptide spontaneously associate to form an enzymatically active Dicer complex.

First Dicer Polypeptide

A first Dicer polypeptide comprises a DUF and a PAZ domain of a Dicer polypeptide. In some cases, a first Dicer polypeptide comprises an amino acid sequence having at least about 85%, at least about 90%, at least about 95%, at least about 98%, at least about 99%, or 100%, amino acid sequence identity to amino acids 1-1008, amino acids 1-1068, amino acids 605-1008, amino acids 605-1068, amino acids 886-1008, or amino acids 886-1068, of the amino acid sequence set forth in FIG. 9 (SEQ ID NO:1). The first Dicer polypeptide lacks RNAse IIIA domain, an RNase IIIb domain, and a double-stranded RNA binding domain. In some cases, the first Dicer polypeptide includes a DExD/H-box domain. In other cases, the first Dicer polypeptide lacks a DExD/H-box domain.

The first Dicer polypeptide can have a length of from about 300 amino acids (aa) to about 1300 aa, e.g., from about 300 aa to about 400 aa, from about 400 aa to about 500 aa, from about 500 aa to about 600 aa, from about 600 aa to about 700 aa, from about 700 aa to about 800 aa, from about 800 aa to about 900 aa, from about 900 aa to about 1000 aa, from about 1000 aa to about 1100 aa, from about 1100 aa to about 1200 aa, or from about 1200 aa to about 1300 aa.

In some embodiments, the first Dicer polypeptide lacks all or a portion of a DExD/H-box helicase domain, and comprises, a domain of unknown function ("DUF283") domain, and a PAZ domain. The DUF and PAZ domains are located in a fragment of amino acids 605 to 1068 of the amino acid sequence depicted in FIG. 9 (SEQ ID NO:1). See, e.g., MacRae and Doudna (2007) Curr. Opin. Struct. Biol. 17:138.

In some embodiments, the first Dicer polypeptide lacks all or a portion of a DExD/H-box helicase domain. The DExD/H-box helicase domain is an N-terminal domain found in many Dicer proteins, and is typically about 600 amino acids in length. In some embodiments, the first Dicer polypeptide lacks from about 200 amino acids to about 250 amino acids, from about 250 amino acids to about 300 amino acids, from about 300 amino acids to about 350 amino acids, from about 350 amino acids to about 400 amino acids, from about 400 amino acids to about 450 amino acids, from about 450 amino acids to about 500 amino acids, from about 500 amino acids to about 550 amino acids, or from about 550 amino acids to about 600 amino acids of a DExD/H-box helicase domain. An exemplary DExD/H-box amino acid sequence is depicted in FIG. 10 (SEQ ID NO:2).

In some embodiments, a first Dicer polypeptide comprises one or more amino acid substitutions, insertions, or deletions in the DExD/H-box domain (e.g., within amino acids 1 to about 604 of the amino acid sequence depicted in FIG. 9, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$). In some embodiments, a first Dicer polypeptide comprises one or more amino acid substitutions, insertions, or deletions in the DExD/H-box domain (e.g., within amino acids 63 to 71 of the amino acid sequence depicted in FIG. 9, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$). In some embodiments, a first Dicer polypeptide comprises one or more amino acid substitutions, insertions, or deletions in the DExD/H-box domain (e.g., within amino acids 175 to 178 of the amino acid sequence depicted in FIG. 9, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$).

In some embodiments, the first modified Dicer polypeptide comprises one or more amino acid substitutions in the DExD/H-box domain (e.g., within amino acids 1 to about 604 of the amino acid sequence depicted in FIG. 9, and as set forth in SEQ ID NO:1, where the one or more amino acid substitutions results in enhanced enzymatic activity (e.g., one or more of increased $k_{cat}$, decreased $K_m$, and increased $k_{cat} \times K_m^{-1}$).

As one non-limiting example, in some embodiments, the first Dicer polypeptide comprises a K70A substitution in the DExD/H-box domain (e.g., within amino acids 1 to about 604 of the amino acid sequence depicted in FIG. 9, and as set forth in SEQ ID NO:1), or a K70A substitution at a corresponding amino acid position, compared to a Dicer polypeptide from a species other than human. For example, in some embodiments, a first Dicer polypeptide: a) comprises a K70A substitution in the DExD/H-box domain, as shown in FIG. 12; b) shares at least about 75%, at least about 80%, at least about 85%, at least about 90%, at least about 95%, at least about 98%, or 100%, amino acid sequence identity over a contiguous stretch of from about 1600 amino acids to about 1700 amino acids, from about 1700 amino acids to about 1800 amino acids, or from about 1800 amino acids to about 1921 amino acids, of the amino acid sequence depicted in FIG. 12 and set forth in SEQ ID NO:4; and c) enhanced enzymatic activity (e.g., one or more of increased $k_{cat}$, decreased $K_m$, and increased $k_{cat} \times K_m^{-1}$) compared to a Dicer polypeptide comprising the amino acid sequence depicted in FIG. 9 and set forth in SEQ ID NO:1.

In some embodiments, a first Dicer polypeptide comprises a K70A substitution in the DExD/H-box domain (e.g., within amino acids 1 to 604 of the amino acid sequence depicted in FIG. 9, and as set forth in SEQ ID NO:1), and shares at least about 75%, at least about 80%, at least about 85%, at least about 90%, at least about 95%, at least about 98%, or 100%, amino acid sequence identity over a contiguous stretch of at least about 1100 amino acids, at least about 1200 amino acids, or at least about 1300 amino acids, of amino acids 605-1922 of the amino acid sequence depicted in FIG. 9 and set forth in SEQ ID NO:1.

As another example, a first Dicer polypeptide comprises one or more amino acid substitutions, insertions, or deletions in the DExD/H-box domain (e.g., within amino acids 63 to 71 of the amino acid sequence depicted in FIG. 9, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$). For example, in some embodiments, a first Dicer polypeptide comprises one or more amino acid substitutions in the amino acid sequence CLNTGSGKT (SEQ ID NO:19) of the amino acid sequence depicted in FIG. 9, or a corresponding amino acid sequence of a Dicer polypeptide other than a human Dicer polypeptide. As shown in the amino acid sequence alignment presented in FIGS. 13A-I, the amino acid sequence CLNTGSGKT (SEQ ID NO:19) is conserved among Dicer polypeptides from various mammalian species.

For example, in some embodiments, a first Dicer polypeptide comprises one or more non-conservative amino acid substitutions in the amino acid sequence CLNTGSGKT (SEQ ID NO:19) of the amino acid sequence depicted in FIG. 9, or a corresponding amino acid sequence of a Dicer polypeptide other than a human Dicer polypeptide. Exemplary, non-limiting examples of amino acid substitutions include, e.g., CLNDGSGKT (SEQ ID NO:20); CLNTPSGKT (SEQ ID NO:21); CLSTGSGKT (SEQ ID NO:22); and the like. For example, in some embodiments, a first Dicer polypeptide: a) comprises a non-conservative amino acid substitution in the amino acid sequence CLNTGSGKT (SEQ ID NO:19); e.g., amino acids 63-71 of the amino acid sequence depicted in FIG. 9, or a corresponding amino acid sequence from a Dicer polypeptide other than a human Dicer polypeptide; b) shares at least about 75%, at least about 80%, at least about 85%, at least about 90%, at least about 95%, at least about 98%, or 100%, amino acid sequence identity over a contiguous stretch of from about 1600 amino acids to about 1700 amino acids, from about 1700 amino acids to about 1800 amino acids, or from about 1800 amino acids to about 1921 amino acids, of the amino acid sequence depicted in FIG. 9 and set forth in SEQ ID NO:1; and c) enhanced enzymatic activity (e.g., increased $k_{cat}$ and/or increased $k_{cat} \times K_m^{-1}$) compared to a Dicer polypeptide comprising the amino acid sequence depicted in FIG. 9 and set forth in SEQ ID NO:1.

As another example, a first Dicer polypeptide comprises one or more amino acid substitutions, insertions, or deletions in the DExD/H-box domain (e.g., within amino acids 175-178 of the amino acid sequence depicted in FIG. 9, and as set forth in SEQ ID NO:1), where the one or more amino acid substitutions, insertions, or deletions result in enhanced enzymatic activity (e.g., increased $k_{cat}$ and/or increased $k_{cat} \times K_m^{-1}$). For example, in some embodiments, a first Dicer polypeptide comprises one or more amino acid substitutions in the amino acid sequence DECH (SEQ ID NO:23) of the amino acid sequence depicted in FIG. 9, or a corresponding amino acid sequence of a Dicer polypeptide other than a human Dicer polypeptide. As shown in the amino acid sequence alignment presented in FIGS. 13A-I, the amino acid sequence DECH (SEQ ID NO:23) is conserved among Dicer polypeptides from various mammalian species.

For example, in some embodiments, a first Dicer polypeptide comprises one or more non-conservative amino acid substitutions in the amino acid sequence DECH (SEQ ID NO:23) of the amino acid sequence depicted in FIG. 9, or a corresponding amino acid sequence of a Dicer polypeptide other than a human Dicer polypeptide. For example, in some embodiments, a first Dicer polypeptide: a) comprises a non-conservative amino acid substitution in the amino acid sequence DECH (SEQ ID NO:23; e.g., amino acids 175-178 of the amino acid sequence depicted in FIG. 9, or a corresponding amino acid sequence from a Dicer polypeptide other than a human Dicer polypeptide; b) shares at least about 75%, at least about 80%, at least about 85%, at least about 90%, at least about 95%, at least about 98%, or 100%, amino acid sequence identity over a contiguous stretch of from about 1600 amino acids to about 1700 amino acids, from about 1700 amino acids to about 1800 amino acids, or from about 1800 amino acids to about 1921 amino acids, of the amino acid sequence depicted in FIG. 9 and set forth in SEQ ID NO:1; and c) enhanced enzymatic activity (e.g., increased $k_{cat}$ and/or increased $k_{cat} \times K_m^{-1}$) compared to a Dicer polypeptide comprising the amino acid sequence depicted in FIG. 9 and set forth in SEQ ID NO:1.

In some embodiments, the first Dicer polypeptide is a chimeric Dicer polypeptide, e.g., the first Dicer polypeptide comprises a heterologous polypeptide. A heterologous polypeptide can be present at the carboxyl terminus, at the amino terminus, or at an internal site within the first Dicer polypeptide. Suitable heterologous polypeptides include, e.g., epitope tags, including, but not limited to, hemagglutinin, FLAG, and the like; proteins that provide for a detectable signal, including, but not limited to, fluorescent proteins, enzymes (e.g., β-galactosidase, alkaline phosphatase, luciferase, horse radish peroxidase, etc.), and the like; polypeptides that facilitate purification or isolation of the fusion protein, e.g., metal ion binding polypeptides such as 6H is tags, glutathione-S-transferase; etc.

Second Dicer Polypeptide

In some embodiments, the second Dicer polypeptide comprises an RNAse IIIA domain, an RNAse IIIb domain, and a double-stranded RNA binding domain (dsRBD), where such domains are included in a fragment of from about amino acid 1235 to 1922 of the amino acid sequence depicted in FIG. 9. See, e.g., MacRae and Doudna (2007) *Curr. Opin. Struct. Biol.* 17:138. The second Dicer polypeptide lacks a DUF domain, a PAZ domain, and a DExD/H-box domain.

In other embodiments, the second Dicer polypeptide comprises an RNAse IIIA domain, an RNAse IIIb domain, and lacks a functional dsRBD. The second Dicer polypeptide lacks a DUF domain, a PAZ domain, and a DExD/H-box domain.

In some cases, a second Dicer polypeptide comprises an amino acid sequence having at least about 85%, at least about 90%, at least about 95%, at least about 98%, at least about 99%, or 100%, amino acid sequence identity to amino acids 1235 to about 1922, or amino acids 1296 to 1922, of the amino acid sequence set forth in FIG. 9.

In some cases, e.g., where a second Dicer polypeptide lacks a functional dsRBD, the second Dicer polypeptide comprises an amino acid sequence having at least about 85%, at least about 90%, at least about 95%, at least about 98%, at least about 99%, or 100%, amino acid sequence identity to amino acids 1235 to about 1772, or amino acids 1296 to 1772, of the amino acid sequence set forth in FIG. 9. For example, in some embodiments, the second Dicer polypeptide lacks a dsRBD, e.g., lacks amino acids 1772-1912 of the amino acid sequence set forth in FIG. 9, lacks amino acids 1772-1922 of the amino acid sequence set forth in FIG. 9, or lacks a substantial portion of amino acids 1772-1912 such that the second Dicer polypeptide lacks a functional dsRBD.

The second Dicer polypeptide can have a length of from about 400 amino acids (aa) to about 950 aa, e.g., from about 400 aa to about 450 aa, from about 450 aa to about 500 aa, from about 500 aa to about 550 aa, from about 600 aa to about 650 aa, from about 650 aa to about 700 aa, from about 700 aa to about 750 aa, from about 750 aa to about 800 aa, from about 800 aa to about 850 aa, from about 850 aa to about 900 aa, or from about 900 aa to about 950 aa.

In some embodiments, the second Dicer polypeptide comprises one or more amino acid substitutions and/or deletions in the dsRBD, such that the dsRBD is non-functional.

In some embodiments, the second Dicer polypeptide is a chimeric Dicer polypeptide, e.g., the second Dicer polypeptide comprises a heterologous polypeptide. A heterologous polypeptide can be present at the carboxyl terminus, at the amino terminus, or at an internal site within the second Dicer polypeptide. Suitable heterologous polypeptides include, e.g., epitope tags, including, but not limited to, hemagglutinin, FLAG, and the like; proteins that provide for a detectable signal, including, but not limited to, fluorescent proteins, enzymes (e.g., β-galactosidase, alkaline phosphatase, luciferase, horse radish peroxidase, etc.), and the like; polypeptides that facilitate purification or isolation of the fusion protein, e.g., metal ion binding polypeptides such as 6H is tags, glutathione-S-transferase; etc.

Dicer Complex

The present disclosure provides a purified Dicer complex. A purified Dicer complex of the present disclosure is useful for producing small regulatory RNAs (e.g., siRNAs and miRNAs) from a dsRNA. A substrate dsRNA is contacted with a subject Dicer complex.

Compositions

The present invention provides a composition comprising a subject Dicer complex. A subject composition can comprise, in addition to the Dicer complex, one or more of: a salt, e.g., NaCl, MgCl$_2$, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

In some embodiments, a Dicer complex present in a subject composition is pure, e.g., at least about 75%, at least about 80%, at least about 85%, at least about 90%, at least about 95%, at least about 98%, at least about 99%, or more than 99% pure, where "% purity" means that the Dicer complex is the recited percent free from other proteins (e.g., proteins other than a subject Dicer complex), other macromolecules, or contaminants that may be present during the production of the Dicer complex.

Nucleic Acids

The present disclosure provides nucleic acids encoding the first and second Dicer polypeptides of a subject Dicer complex. A subject nucleic acid is recombinant. The present invention further provides a composition comprising a subject nucleic acid. In some cases, a subject nucleic acid comprises a nucleotide sequence encoding both the first and the second Dicer polypeptides of a subject Dicer complex. In other embodiments, two separate nucleic acids encode the two Dicer polypeptides; thus, the present disclosure provides a first nucleic acid comprising a nucleotide sequence encoding the first Dicer polypeptide of a subject Dicer complex; and a second nucleic acid comprising a nucleotide sequence encoding the second Dicer polypeptide of a subject Dicer complex.

In some embodiments, a subject nucleic acid is an expression construct, e.g., an expression vector comprising a nucleotide sequence encoding one or both of a first Dicer polypeptide and a second Dicer polypeptide of a subject Dicer complex, where the expression construct provides for production of the encoded modified Dicer polypeptide(s) in an appropriate host cell. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast).

Suitable vectors for the production of first and/or second Dicer polypeptides in a prokaryotic cell include plasmids of the types: pBR322-derived plasmids, pEMBL-derived plasmids, pEX-derived plasmids, pBTac-derived plasmids and pUC-derived plasmids for expression in prokaryotic cells, such as *Escherichia coli*. The following vectors are provided by way of example, for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia). However, any other plasmid or other vector may be used so long as it is compatible with the host cell.

A number of vectors exist for the expression of recombinant proteins in yeast. For instance, YEP24, YIPS, YEP51, YEP52, pYES2, and YRP17 are cloning and expression vehicles useful in the introduction of genetic constructs into *Saccharomyces cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a one or both of the first and second Dicer polypeptides is produced recombinantly utilizing an expression vector generated by sub-cloning a nucleotide sequence encoding one or both of the first and second Dicer polypeptides of a subject Dicer complex.

In some embodiments, the expression construct comprises a mammalian expression vector. Suitable mammalian expression vectors include those that contain both prokaryotic sequences, to facilitate the propagation of the vector in bacteria, and one or more eukaryotic transcription units that are expressed in eukaryotic cells. The pcDNAI/amp, pcDNA/neo, pRc/CMV, pSV2gpt, pSV2neo, pSV2-dhfr, pTk2, pRS-Vneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Ban virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17.

A first and/or a second Dicer polypeptide can be produced using an expression vector containing a nucleic acid encoding first and/or a second Dicer polypeptide, operably linked to at least one transcriptional regulatory sequence. Operably linked is intended to mean that the nucleotide sequence is linked to a regulatory sequence in a manner that allows expression of the nucleotide sequence. Regulatory sequences are art-recognized and are selected to direct expression of the encoded first and/or second Dicer protein. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding Dicer polypeptides to recombinantly produce a subject Dicer complex. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAG or TRC system, T7 promoter whose expression is directed by T7 RNA polymerase, the major operator and promoter regions of phage X, polyhedron promoter, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters include CMV immediate early, HSV thymidine kinase, early and late SV40, LTRs from retrovirus, and mouse metallothionein-I. Suitable promoters for expression in yeast include, but are not limited to, CYC1, HIS3, GAL1, GAL10, ADH1, PGK, PHO5, GAPDH, ADC1, TRP1, URA3, LEU2, ENO, and TP1; and, e.g., AOX1 (e.g., for use in *Pichia*).

In some embodiments, the promoter is an inducible promoter. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

Compositions

The present invention provides a composition comprising a subject nucleic acid(s). A subject composition can comprise, in addition to a subject nucleic acid(s), one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; glycerol; and the like.

Genetically Modified Host Cells

The present invention provides genetically modified host cells comprising a subject nucleic acid(s). Suitable host cells include, e.g., prokaryotic host cells (e.g., prokaryotic cells in vitro). The present invention further provides composition comprising a subject genetically modified host cell.

Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. In some embodiments, the host cell is *Escherichia coli*.

Suitable methods of genetic modification of a host cell include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. To generate a subject genetically modified host cell, a subject nucleic acid is introduced stably or transiently into a host cell, using established techniques, including, but not limited to, electroporation, lithium acetate transformation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

Compositions

The present invention provides a composition comprising a subject genetically modified host cell. A subject composition comprises a subject genetically modified host cell, and will in some embodiments comprise one or more further components, which components are selected based in part on the intended use of the genetically modified host cell, storage considerations, etc. Suitable components include, but are not limited to, salts; buffers; stabilizers; protease-inhibiting agents; nuclease-inhibiting agents; cell membrane- and/or cell wall-preserving compounds, e.g., glycerol, dimethylsulfoxide, etc.; nutritional media appropriate to the cell; and the like. In some embodiments, the cells are lyophilized.

Production of a Subject Dicer Complex

A host cell is genetically modified with a subject nucleic acid, such that one or both of the first and second polypeptides of a subject Dicer complex is produced in the genetically modified host cell, and the encoded first and/or second Dicer polypeptide is (are) produced by the cell. The genetically modified host cell is cultured in vitro under suitable conditions such that one or both of the first and second polypeptides of a subject Dicer complex is produced. Where the nucleotide sequence encoding one or both of the first and second polypeptides of a subject Dicer complex is operably linked to an inducible promoter, an inducer is added to the culture medium in which the genetically modified host cell is cultured.

The first and/or the second Dicer polypeptides can be recovered and isolated from the genetically modified host cell; and allowed to form a complex outside the cell. In some embodiments, one or both of the first and second polypeptides of a subject Dicer complex polypeptide is purified, e.g., is at least about 80%, at least about 85%, at least about 90%, at least about 95%, at least about 98%, or at least about 99% pure. Any convenient protein purification procedures may be employed, where suitable protein purification methodologies are described in Guide to Protein Purification, (Deuthser ed.) (Academic Press, 1990). For example, a lysate may be prepared from a genetically modified host cell that expresses one or both of the first and second polypeptides of a subject Dicer complex, and purified using any of a number of standard protein purification methods, e.g., high performance liquid chromatography, size exclusion chromatography, gel electrophoresis, affinity chromatography, and the like.

Utility

A subject Dicer complex is useful for producing small regulatory RNAs, which in turn are useful in a number of applications, including basic research applications, drug screening/target validation, large scale functional library screening, and therapeutic applications. Thus, the present disclosure provides methods of producing a small regulatory RNA molecule from a substrate dsRNA molecule. Small regulatory RNA molecules that can be produced using a subject method include siRNA and miRNA.

Methods of Producing a Small Regulatory RNA Molecule

The present invention provides methods of producing small regulatory RNA from a substrate dsRNA molecule, the methods generally involving contacting the substrate dsRNA molecule with a subject Dicer complex, where the Dicer complex efficiently produces a small regulatory RNA using the substrate dsRNA molecule. The methods described below are directed to producing siRNA; however, a subject method can be adapted for producing miRNA.

In some embodiments, a subject method provides for production of a plurality of small regulatory RNA molecules, e.g., a plurality of siRNA molecules or a plurality of miRNA molecules. By "plurality" is meant at least 2, at least about 5, or at least about 10, where the number of distinct siRNA or miRNA molecules produced from a given substrate dsRNA molecule in the subject methods can depend on the length of the substrate dsRNA molecule, but may be as high as about 25 or higher, e.g., about 100, or about 400 or higher.

The siRNA or miRNA product molecules can range in length from about 10 nucleotides (nt) to about 25 nt, e.g., from about 10 nt to about 15 nt, from about 15 nt to about 20 nt, or from about 20 nt to about 25 nt. In some embodiments, a subject Dicer complex produces siRNA product molecules having a length of from about 19 nt to about 24 nt, from about 20 nt to about 24 nt, from about 21 nt to about 24 nt, or from about 21 nt to about 23 nt. In some embodiments, a subject Dicer complex produces siRNA product molecules, where at least about 75%, at least about 80%, at least about 85%, at least about 90%, at least about 95%, at least about 98%, or at least about 99%, of the siRNA molecules have a length of from 21 nt to 23 nt.

A subject Dicer complex is contacted with a substrate dsRNA molecule. The length of the parent dsRNA molecule can vary, but generally the length is at least about 300 bp, at least about 500 bp, or at least about 1000 bp, where the length may be as long as about 2000 bp or longer, but often does not exceed about 8000 bp, e.g., about 6000 bp.

The dsRNA substrate can comprise two hybridized strands of polymerized ribonucleotide. The dsRNA substrate can include modifications to either the phosphate-sugar backbone or the nucleoside. For example, the phosphodiester linkages of natural RNA may be modified to include at least one of a nitrogen or a sulfur heteroatom. Modifications in RNA structure may be tailored to allow specific genetic inhibition while avoiding an adverse response in the cell harboring the RNA. Likewise, bases may be modified to block the activity of adenosine deaminase. The dsRNA substrate may be produced enzymatically or by partial/total organic synthesis, any modified ribonucleotide can be introduced by in vitro enzymatic or organic synthesis.

The dsRNA substrate is formed by a single self-complementary RNA strand or by two complementary RNA strands. dsRNA substrates comprising a nucleotide sequence identical to a portion of a target gene may be employed. RNA sequences with insertions, deletions, and single point mutations relative to the target sequence are also of interest. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BEST-FIT software program using default parameters (e.g., University of Wisconsin Genetic Computing Group). In some embodiments, there is at least about 80%, at least about 85%, at least about 90%, at least about 95%, at least about 98%, at least about 99%, or 100%, sequence identity between the siRNA or miRNA and the portion of a target gene may be of interest. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 50° C. or 70° C. hybridization for 12-16 hours; followed by washing; or conditions that are at least as stringent as these representative conditions). The length of the identical nucleotide sequences may be, for example, at least about 25, about 50, about 100, about 200, about 300 or about 400 bases or longer. In certain embodiments, the dsRNA substrate is from about 400 to about 800 bases in length. In certain embodiments 100% sequence identity between the RNA and the target gene is not required to practice inhibition applications of the invention. Thus the invention has the advantage of being able to tolerate sequence variations that might be expected due to genetic mutation, strain polymorphism, or evolutionary divergence.

The dsRNA substrate can be synthesized either in vivo or in vitro. Furthermore, the dsRNA substrate can be synthesized in vitro in a living cell, or in a cell-free in vitro system. Endogenous polymerase of the cell can mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the dsRNA strand (or strands). In some embodiments, the RNA strands of the dsRNA substrate are polyadenylated. In other embodiments, the RNA strands of the dsRNA substrate are not polyadenylated. In some embodiments, the RNA strands of the dsRNA substrate are capable of being translated into a polypeptide by a cell's translational apparatus or in a cell-free in vitro translation system. In some embodiments, the RNA strands of the dsRNA substrate are not capable of being translated into a polypeptide by a cell's translational apparatus or in a cell-free in vitro translation system.

The dsRNA substrate can be chemically or enzymatically synthesized by manual or automated reactions. The dsRNA substrate can be synthesized by a cellular RNA polymerase or a bacteriophage RNA polymerase (e.g., T3, T7, or SP6), e.g., using an expression construct encoding the dsRNA as template. The use and production of expression constructs are known in the art (see WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA can be purified prior to introduction into the cell. For example, RNA can be purified from a mixture by extraction with a solvent or resin, precipitation, electrophoresis, chromatography or a combination thereof. Alternatively, the dsRNA construct may be used with no or a minimum of purification to avoid losses due to sample processing. The dsRNA construct may be dried for storage or dissolved in an aqueous solution. The solution may contain buffers or salts to promote annealing, and/or stabilization of the duplex strands.

In some embodiments, at least about 60%, at least about 75%, at least about 80%, at least about 85%, at least about 90%, at least about 95%, at least about 98%, or at least about 99%, of the substrate dsRNA is cleaved to produce an miRNA or siRNA product.

In the reaction composition (e.g., the composition comprising a subject Dicer complex and a dsRNA substrate), the amount of Dicer complex present in the composition can vary, and can be in a range of from about 20 ng/µl to about 160 ng/µl, e.g., from about 20 ng/µl to about 40 ng/µl, from about 40 ng/µl to about 60 ng/µl, from about 60 ng/µl to about 80 ng/µl, from about 80 ng/µl to about 100 ng/µl, from about 100 ng/µl to about 120 ng/µl, from about 120 ng/µl to about 140 ng/µl, or from about 140 ng/µl to about 160 ng/µl.

In some embodiments, the reaction composition (e.g., the composition comprising a subject Dicer complex and a dsRNA substrate) is an aqueous composition, where the composition may include one or more additional components, e.g., buffers; salts such as NaCl, $MgCl_2$, and the like; EDTA; DTT; ATP; and the like.

As discussed above, a subject method comprises contacting a subject Dicer complex with a substrate dsRNA in a reaction composition that is then maintained under conditions sufficient to produce the desired siRNA or miRNA product. In some embodiments, a subject method is a cell-free in vitro method, by which is meant that the method occurs in a cell free environment, e.g., not inside of a cell or in the presence of cells. As such, in some embodiments, a subject method involves producing a product composition comprising an siRNA product or a miRNA product, where the product composition is produced by contacting a substrate dsRNA and a subject Dicer complex, as described above, where the product composition is produced in a cell-free in vitro reaction, i.e., in vitro and outside of a cell.

In some embodiments, a subject Dicer complex and a substrate dsRNA are contacted in reaction composition that includes a sufficient amount of $Mg^{2+}$ to ensure adequate Dicer activity, where the amount of $Mg^{2+}$ can range from about 0.5 mM to about 1.0 mM, or from about 2.5 mM to about 5.0 mM. In some embodiments, the reaction composition is free of ATP, and in other embodiments, 1 mM ATP is used in the reaction composition.

The reaction mixture is typically maintained under incubation conditions sufficient to produce the desired small regulatory RNA product. The reaction mixture is typically maintained at a temperature that ranges from about 30° C. to about 37° C., e.g., from about 35° C. to about 37° C. The reaction is carried out for a period of time ranging from about 15 minutes to about 24 hours, e.g., from about 15 minutes to about 30 minutes, from about 30 minutes to about 60 minutes, from about 1 hour to about 2 hours, from about 2 hours to about 4 hours, from about 4 hours to about 8 hours, from about 8 hours to about 12 hours, from about 12 hours to about 16 hours, or from about 16 hours to about 24 hours.

The small regulatory RNA product, e.g., the siRNA product or the miRNA produce, produced by a subject method may be used as is or further processed prior to use, e.g., separated from other components of the reaction mixture, e.g., the Dicer comlex, any remaining dsRNA substrate, salts, buffers, etc. Any convenient separation protocol may be employed, including gel purification, chromatographic separation based on molecular weight or affinity resins, and classical precipitation, and the like.

Research Applications

A small regulatory RNA can be used for modifying biological functions in a cell (e.g., a cell growing as a single-cell suspension in vitro; a cell in a multicellular organism; etc.), such as for example, RNA interference, gene knockdown or knockout, generating expression mutants, modulating cell growth, differentiation, signaling or a combination thereof. Thus, in some embodiments, a subject method involves: a) producing an siRNA using a subject method (i.e., using a subject Dicer complex); and b) introducing the siRNA so produced into a cell (e.g., into a cell in vitro; or into a non-human cell in a multi-cellular organism in vivo).

One representative utility is a method of identifying gene function in an organism, e.g., higher eukaryotes comprising the use of the product siRNA to inhibit the activity of a target gene of previously unknown function. Instead of the time consuming and laborious isolation of mutants by traditional genetic screening, functional genomics using the subject product siRNA determines the function of uncharacterized genes by employing the siRNA to reduce the amount and/or alter the timing of target gene activity. The product siRNA can be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for mammalian genomes, can be coupled with use of the product siRNA to determine gene function in a cell or in a whole organism. The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

A simple representative assay involves inhibition of gene expression according to the partial sequence available from an expressed sequence tag (EST). Functional alterations in growth, development, metabolism, disease resistance, or other biological processes would be indicative of the normal role of the EST's gene product.

The ease with which the product siRNA construct can be introduced into an intact cell/organism containing the target gene allows the siRNA products to be used in high throughput screening (HTS). For example, individual clones from the library can be replicated and then isolated in separate reactions, but preferably the library is maintained in individual reaction vessels (e.g., a 96-well microtiter plate) to minimize the number of steps required to practice the invention and to allow automation of the process. Solutions containing the product siRNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity.

The siRNA can be fed directly to, injected into, the cell/organism containing the target gene. The siRNA may be directly introduced into the cell (i.e., intracellularly); or introduced extracellularly into a cavity, interstitial space, into the circulation of an organism, introduced orally, or may be introduced by bathing an organism in a solution containing the siRNA. Methods for oral introduction include direct mixing of RNA with food of the organism. Physical methods of introducing nucleic, acids include injection directly into the cell or extracellular injection into the organism of an RNA solution. The siRNA may be introduced in an amount that allows delivery of at least one copy per cell. Higher doses (e.g., at least 5, 10, 100, 500 or 1000 copies per cell) of siRNA material may yield more effective inhibition; lower doses may also be useful for specific applications. Inhibition is sequence-specific in that nucleotide sequences corresponding to the duplex region of the RNA are targeted for genetic inhibition.

The function of the target gene can be assayed from the effects it has on the cell/organism when gene activity is inhibited. This screening could be amenable to small subjects that can be processed in large number, for example, tissue culture cells derived from invertebrates or vertebrates (e.g., mammals, such as murines, non-human primates, and humans).

If a characteristic of an organism is determined to be genetically linked to a polymorphism through RFLP or QTL analysis, the present invention can be used to gain insight regarding whether that genetic polymorphism might be directly responsible for the characteristic. For example, a fragment defining the genetic polymorphism or sequences in the vicinity of such a genetic polymorphism can be amplified to produce a dsRNA from which siRNA is prepared according to the subject methods, which siRNA can be introduced to the organism or cell, and whether an alteration in the characteristic is correlated with inhibition can be determined.

A Dicer complex of the present disclosure is useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of siRNA at specific times of development and locations in the organism without introducing permanent mutations into the target genome.

In situations where alternative splicing produces a family of transcripts that are distinguished by usage of characteristic exons, an siRNA can target inhibition through the appropriate exons to specifically inhibit or to distinguish among the functions of family members.

Therapeutic Applications

An siRNA produced using a subject method also finds use in a variety of therapeutic applications in which it is desired to selectively modulate one or more target genes in a host, e.g., a whole animal, or a portion thereof, e.g., a tissue, an organ, etc., as well as in cells present such an animal, tissue, or organ. In such methods, an effective amount of an siRNA is administered to the host or target portion thereof. By "effective amount" is meant a dosage sufficient to selectively modulate expression of the target gene(s), as desired. As indicated above, in many embodiments of this type of application, methods are employed to reduce/inhibit expression of one or more target genes in the host or portion thereof in order to achieve a desired therapeutic outcome.

In some embodiments, a subject method comprises: preparing an siRNA according to a subject method (i.e., using a subject Dicer complex); and administering an effective amount of the siRNA to an individual in need thereof.

Depending on the nature of the condition being treated, the target gene may be a gene derived from the cell, an endogenous gene, a pathologically mutated gene, e.g. a cancer-causing gene, one or more genes whose expression causes or is related to heart disease, lung disease, Alzheimer's disease, Parkinson's disease, diabetes, arthritis, etc.; a transgene, or a gene of a pathogen which is present in the cell after infection thereof, e.g., a viral (e.g., HIV-Human Immunodeficiency Virus; Hepatitis B virus; Hepatitis C virus; Herpes-simplex virus-1 and -2; Varicella Zoster (Chicken pox and Shingles); Rhinovirus (common cold and flu); any other viral form); or bacterial pathogen. Depending on the particular target gene and the dose of siRNA delivered, the procedure may provide partial or complete loss of function for the target gene. Lower doses of injected material and longer times after administration of siRNA may result in inhibition in a smaller fraction of cells.

An siRNA produced using a subject method finds use in the treatment of a variety of conditions in which the modulation of target gene expression in a mammalian host is desired. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable using an siRNA. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, and non-human primates such as chimpanzees and monkeys). In some embodiments, the hosts will be humans.

The present disclosure is not limited to modulation of expression of any specific type of target gene or nucleotide sequence. Representative classes of target genes of interest include but are not limited to: developmental genes (e.g., adhesion molecules, cyclin kinase inhibitors, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FOR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor genes (e.g., APC, BRCA 1, BRCA2, MADH4, MCC, NF 1, NF2, RB 1, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, Upases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); chemokines (e.g. CXCR4, CCR5); the RNA component of telomerase; vascular endothelial growth factor (VEGF); VEGF receptor; tumor necrosis factors nuclear factor kappa B; transcription factors; cell adhesion molecules; Insulin-like growth factor; transforming growth factor beta family members; cell surface receptors; RNA binding proteins (e.g. small nucleolar RNAs, RNA transport factors); translation factors; telomerase reverse transcriptase); etc.

The siRNA can be introduced into the target cell(s) using any convenient protocol, where the protocol will vary depending on whether the target cells are in vitro or in vivo.

Where the target cells are in vivo, the siRNA can be administered to the host comprising the cells using any convenient protocol, where the protocol employed is typically a nucleic acid administration protocol, where a number of different such protocols are known in the art. The following discussion provides a review of representative nucleic acid administration protocols that may be employed. The nucleic acids may be introduced into tissues or host cells by any number of routes, including microinjection, or fusion of vesicles. Jet injection may also be used for intra-muscular administration, as described by Furth et al. (1992), *Anal Biochem* 205:365-368. The nucleic acids may be coated onto gold microparticles, and delivered intradermally by a particle bombardment device, or "gene gun" as described in the literature (see, for example, Tang et al. (1992), Nature 356:152-154), where gold microprojectiles are coated with the DNA, then bombarded into skin cells.

For example, the d-siRNA agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. Methods for oral introduction include direct mixing of RNA with food of the organism. Physical methods of introducing nucleic acids include injection directly into the cell or extracellular injection into the organism of an RNA solution.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. Pat. Nos. 5,985,847 and 5,922,687 (the disclosures of which are herein incorporated by reference); Acsadi et al., New Biol. (1991) 3:71-81; Hickman et al., Hum. Gen. Ther. (1994) 5:1477-1483; and Wolff et al., Science (1990) 247: 1465-1468; etc.

An siRNA (also referred to as an "agent" or an "active agent") can be administered to the host using any convenient means capable of resulting in the desired modulation of target gene expression. Thus, the agent can be incorporated into a variety of formulations for therapeutic administration. More particularly, the agents can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

Suitable delivery reagents for administration of an siRNA include the Minis Transit TKO lipophilic reagent; lipofectin; lipofectamine; cellfectin; polycations (e.g., polylysine); and liposomes.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more agents. Similarly, unit dosage forms for injection or intravenous administration may comprise the agent(s) in a composition as a solution in sterile water, normal saline or another pharmaceutically acceptable carrier.

The term "unit dosage form," as used herein, refers to physically discrete units suitable as unitary dosages for human and non-human animal subjects, each unit containing a predetermined quantity of an active agent calculated in an amount sufficient to produce the desired effect in association with a pharmaceutically acceptable diluent, carrier or vehicle.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given active agent are readily determinable by those of skill in the art by a variety of means.

Kits

The present disclosure provides a kit for producing a subject Dicer complex. A subject kit comprises: a) a first recombinant expression vector comprising a nucleotide sequence encoding a first Dicer polypeptide, wherein the first Dicer polypeptide comprises a DUF and a PAZ domain; and b) a second recombinant expression vector comprising a nucleotide sequence encoding a second Dicer polypeptide comprises an RNAse IIIA domain, an RNase IIIb domain, and a double-stranded RNA binding domain. The first and the second Dicer polypeptides are amply described above. The components can be in separate containers.

In addition to above-mentioned components, a subject kit can include instructions for using the components of the kit to practice a subject method for producing a Dicer complex. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Dicer Complex

Experimental Procedures
RNA Substrates

All of the RNA oligonucleotides ("oligos") with exception of pre-hlet-7a-1 listed below were synthesized by IDT (Integrated DNA Technologies, Inc, Coralville, Iowa). All RNA oligos were purified by 16% urea-polyacrylamide gel electrophoresis (PAGE) before use. Human pre-let-7a-1 hairpin RNA (pre-hlet-7a-1, 73 nt) was transcribed in vitro by T7 RNA polymerase from a construct containing a double ribozyme system to ensure homogeneous 5' and 3' ends (29). An artificial hairpin RNA (37ab-loop, 79 nt) was made by the ligation of 37a-loop and 5'-phosphated 37b-loop (see below) with T4 RNA ligase from BioLabs (New England BioLabs, Inc, Beverly, Mass.). The 37ab-loop RNA was constructed such that it contains a perfectly matched stem from 37ab (see below) and a terminal loop from pre-hlet-7a-1. The RNA oligos of 37a and 37b can form a perfectly matched duplex (37ab). The RNA oligos of 21a and 21b were annealed to form duplex siRNA. The oligos of hlet7-stem-a and hlet7-stem-b can form a stem (hlet7-stem) from pre-hlet7 after annealing. For both filter binding and dicing assays, the purified RNA substrates were 5'-end labeled with $^{32}$P using T4 polynucleotide kinase (New England Biolabs, Inc. Beverly, Mass.), gel-purified and annealed before use. The sequences of all of RNA substrates used in this study are:

```
pre-hlet-7a-1:
                                       (SEQ ID NO: 9)
5'-UGAGGUAGUAGGUUGUAUAGUUUUAGGGUCACACCCAC

CACUGGGAGAUAACUAUACAAUCUACUGUCUUACC-3';
```

```
hlet7-stem-a:
                                       (SEQ ID NO: 10)
UGAGGUAGUAGGUUGUAUAGUUUGAAAGUUCACGAUU-3';

hlet7-stem-b:
                                       (SEQ ID NO: 11)
AAUCGUGAACUUUCAAACUAUACAAUCUACUGUCUUACC-3';

37a-loop:
                                       (SEQ ID NO: 14)
UGAGGUAGUAGGUUGUAUAGUUUGAUUAGGGUCACACCCACC-3';

37b-loop:
                                       (SEQ ID NO: 15)
5'-P-ACUGGGAGAUUCAAACUAUACAACCUACUACCUCAUU-3';

37a:
                                       (SEQ ID NO: 10)
5'-UGAGGUAGUAGGUUGUAUAGUUUGAAAGUUCACGAUU-3';

37b:
                                       (SEQ ID NO: 12)
5'-UCGUGAACUUUCAAACUAUACAACCUACUACCUCAUU-3';

pre-miR20a:
                                       (SEQ ID NO: 16)
5'UAAAGUGCUUAUAGUGCAGGUAGUGUGUAGCCAUCUACUGCA

UUACGAGCACUUAAAG-3';

21a:
                                       (SEQ ID NO: 17)
5'-UAUACAAUGUGCUAGCUUUCU-3';
and 21b:
                                       (SEQ ID NO: 18)
5'-AAAGCUAGCACAUUGUAUAGU-3'.
```

Dicer Constructs for Sf9 and Bacterial Expression

To structurally probe hDcr and obtain its globular fragments, limited proteolysis was performed with endoproteinase Glu-C (Sigma-Aldrich, St. Louis, Mo.). Specifically, 60 ng of Glu-C was incubated with 30 μg of hDcr on ice for 60 min. The proteolytic fragments were separated on a 10% sodium dodecyl sulfate-PAGE (SDS-PAGE) and were then either stained with Coomassie Brilliant Blue and cut for MassSpec or transferred onto a polyvinylidene fluoride (PVDF) membrane (Millipore, Billerica, Mass.) for Edman degradation sequencing.

The N-terminal (hDcr-N: 1-1068) and C-terminal (hDcr-C: 1235-1922) fragments were co-expressed in SF9 cells transfected with their baculoviruses as described previously (7). The bacteria-expression constructs were designed based on the alignment data of published Dicer sequence (4, 10) (ATPase/helicase (ATPase/Hel): 1-604; DUF283-PAZ (DP): 605-1068; hDcr-C: 1235-1922; and hDcr-CARBD: 1235-1844). The corresponding DNA fragments were generated by polymerase chain reaction (PCR) and then cloned into pENTR/TEV/D-TOPO vector (Invitrogen). After being confirmed by sequencing, the right inserts were subcloned into destination vector of pHMGWA-His6-MBP by LR Clonase™ II enzyme mix (Invitrogen). The pHMGWA-His6-MBP vector is kindly provided by Dr. Busso, CNRS/INSERM/Université Louis Pasteur, France (30).

Filter Binding Assays

Filter binding assays of hDcr and different hDcr fragments were performed in the same way as previously described (7). Briefly, serial dilutions of hDcr protein were incubated in a buffer containing 20 mM Tris-HCl (pH 7.5), 25 mM NaCl, 5 mM EDTA, 1 mM dithiothreitol (DTT), 1% glycerol and ~0.5-1 nM (1500 CPM) of 5'-end $^{32}$P-labeled duplex RNA substrate (one strand was labeled) at room temperature for 60 min in a 30 μl of total volume. Following incubation, a 25 μl aliquot of each reaction was applied to a dot-blot apparatus equipped with three membranes: Tuffryn, Protran and Nytran (from top to bottom). After drying, the bound (on Protran) or free (on Nytran) RNAs were quantified by a Phosphorimager (GE Healthcare). Percent bound RNA, calculated as the ratio of radioactivity detected on the Protran membrane over the total input radioactivity, was plotted as a function of protein concentration. $K_d$ was determined by global fitting to the equation: $k_{obsd} = (k_{max} - [Dicer])(K_d + [Dicer]) - 1$, where $k_{obsd}$ is the observed rate constant at a given protein concentration, $k_{max}$ is the maximal rate constant with saturating protein, and $K_d$ is the protein concentration that provides half the maximal rate. Curve fitting was conducted with KaleidaGraph (Synergy Software, Reading, Pa.).

Dicing Assays

The cleavage assays of hDcr were carried out similarly as described previously (7). Simply, dsRNA substrates were 5'-end labeled with γ-$^{32}$P-ATP, annealed and incubated with 30 nM of hDcr (otherwise, stated in figure legends) at 37° C. for the specified time in a 10 μl volume (unless otherwise indicated) containing 20 mM Tris-HCl (pH 6.5), 1.5 mM MgCl$_2$, 25 mM NaCl, 1 mM DTT and 1% glycerol. Reactions were stopped by addition of 1.2 volumes of loading buffer (95% formamide, 18 mM EDTA, 0.025% SDS, 0.1% xylene cyanole FF and 0.1% bromophenol blue). After heating at 70° C. for 10 min, the samples were analyzed by electrophoresis through a 15% polyacrylamide-7M urea gel run in Tris-borate-EDTA (TBE) buffer and quantified using a Phosphorimager, and data quantification was achieved using ImageQuant TL.

ATPase Hydrolysis Assays

In vitro ATPase assay was performed as described elsewhere (31) with some modifications. ATPase hydrolysis assay was carried out in a 5 μl reaction of mixture containing 200 nM hDcr or ATPase/helicase domain, 200 nM dsRNA (or without RNA), 83.3 nM γ-$^{32}$P-ATP and 20 nM cold ATP in a buffer consisting of 50 mM MES (pH 6.5), 50 mM KAc, 2.5 mM Mg(Ac)$_2$, 1 mM dithiothreitol (DTT) and 0.1 mg/ml bovine serum albumin (BSA). The reaction mixture was incubated at 37° C. for the indicated time. After incubation, the reaction was terminated by addition of 2 μl of 50 mM EDTA. The reaction mixture was separated by loading 0.5 μl of the reaction mixture on the PEI-cellulose plate and running for ~1 hour in a buffer containing 0.5 M LiCl and 1 M formic acid. After drying, the polyethyleneimine (PEI)-cellulose plate was quantified using a Phosphorimager, and data quantification was achieved by using software of ImageQuant TL.

Pull-Down Assays

Six microgram of both of hTRBP2 and mbp-ATPase/hel-HA proteins were mixed with 15 μl of anti-hemagglutinin (anti-HA) antibody-coupled agarose beads in 1× phosphate-buffered saline (PBS) buffer (Sigma, Saint Louis, Mo.) and incubated in cold room and rocked 60 min. The mixture was pelleted by 30 sec spin at 10,000×g and then washed once with 1×PBS and followed by 5 times with the washing buffer of 20 mM Hepes (pH 7.5), 250 mM NaCl, 1% glycerol and 0.1% Triton X-100. After the last wash, the pellet was boiled for 3 min in 1.2×SDS protein loading buffer. As a control, hTRBP2 alone was also processed in the same way.

Results

A Fully Active hDcr can be Reconstituted from Trans-Expressed Fragments

The large size and multi-domain composition of hDcr have presented challenges to its expression, purification and analysis in recombinant form (4, 10). Previous studies have relied on the presence of endogenous hDcr in cell extracts or purified hDcr obtained by over-expression in baculovirus-infected insect cells. These approaches preclude ready analysis of hDcr domain functions due to the difficulties of preparing mutant proteins in these systems. Although prior attempts to express hDcr in E. coli were unsuccessful, it was reasoned that it might be possible to break the protein into smaller fragments that could be individually expressed in bacteria. Using full-length active recombinant hDcr purified from its baculovirus-infected Sf9 cells, limited proteolysis was performed using endoproteinase Glu-C to obtain globular hDcr fragments. This treatment produced two stable polypeptides (FIG. 1A). The results from both mass spectrometry and Edman degradation sequencing showed that one fragment contains the ATPase/hel, DUF283, and PAZ domains (N-terminal fragment, hDcr-N) and the other contains the two tandem RNase III domains and the C-terminal dsRBD (C-terminal fragment, hDcr-C) (FIG. 1A). Recombinant baculovirus constructs were prepared for these polypeptides and their expression was tested in baculovirus-infected Sf9 cells. Although the two fragments could not be individually expressed in this system, co-expression led to production of a stable complex (FIG. 1B) that could not be disrupted by either 1 M sodium chloride or 4 M urea. To check whether the co-expressed complex was correctly folded and functional, cleavage assays were performed with a 35-base pair substrate (37ab, see FIG. 5A). These dicing assays showed that the hDcr-N/C complex is active and its activity is similar to that of wild-type hDcr (FIG. 1C, FIG. 6).

FIGS. 1A-C. Human Dicer can be Separated into Functional Fragments that Interact in Trans.

A. Proteolysis of full-length recombinant hDicer (FL-hDcr) protein. Dose-dependent proteolysis of FL-hDcr protein (10 μg for each reaction) with endoproteinase Glu-C was used to screen for optimal proteolytic conditions (left panel). The two identified globular protein fragments marked with hDcr-N and hDcr-C were isolated for mass spectrometry and Edman degradation sequencing. The isolated fragments of hDcr-N and hDcr-C from the partial proteolysis are represented in relation to wild-type FL-hDcr (right panel). B. Co-expression of the hDcr fragments in Sf9 cells. The co-expressed hDcr-N and hDcr-C fragments form a stable complex as shown from the elution profile of Superdex 200 size-exclusion chromatography (left panel). An SDS-PAGE gel shows the two protein fragments either from a Ni$^{2+}$-column after TEV protease cleavage (Ni$^{2+}$) or from the Superdex 200 size-exclusion column (Sup200). M is prestained protein ladder, SeeBlue Plus2 (Invitrogen). C. The complex (hDcr-N/hDcr-C) displays cleavage activity similar to that of FL-hDcr. In the cleavage assay, the hDcr-N/hDcr-C complex (lane 2) or FL-hDcr (lane 3) was incubated with 37ab RNA substrate, of which 37a was $^{32}$P-labeled. From this substrate, hDcr generates two products of 22-nt and 15-nt.

Figure 6:
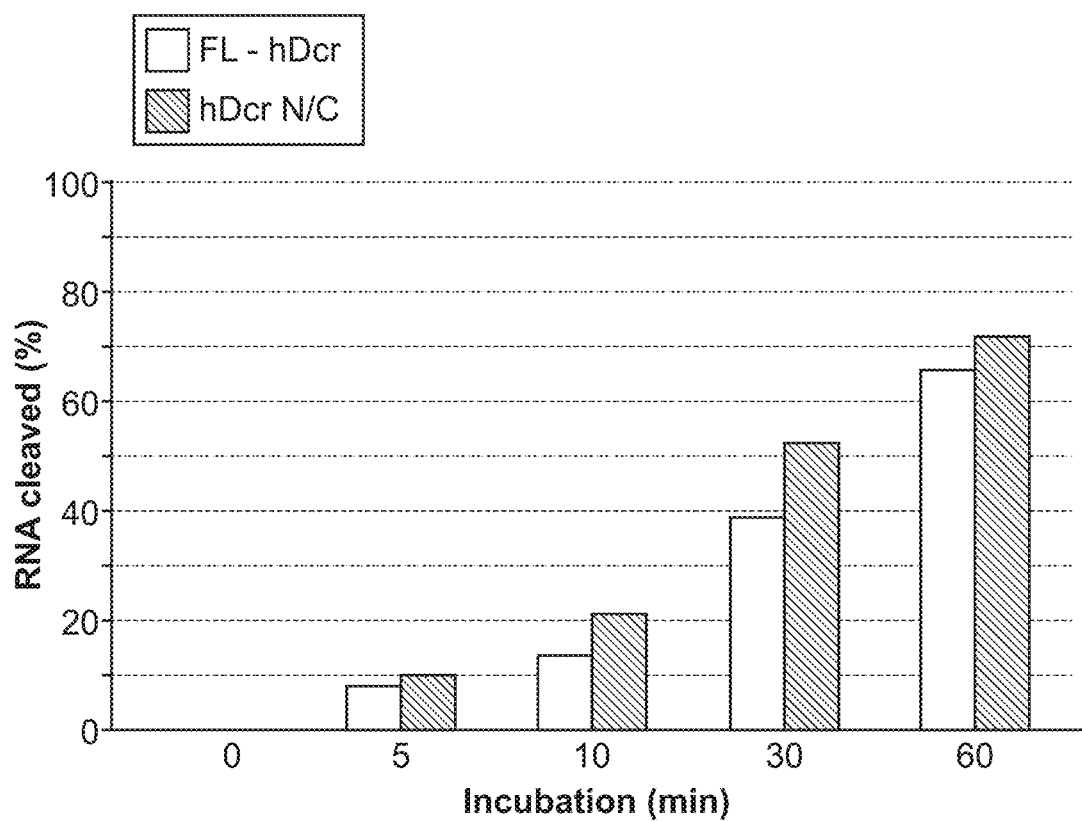
FIG. 6 depicts the activity of hDcr-N/C complex expressed in trans and the activity of wild-type hDcr.

FIG. 6. The Activity of hDcr-N/C Complex Expressed in Trans is Similar to Wild-Type hDcr.

Time course dicing assays show no significant difference between trans-expressed hDcr-N/C complex and wild-type hDcr.

Figure 2:
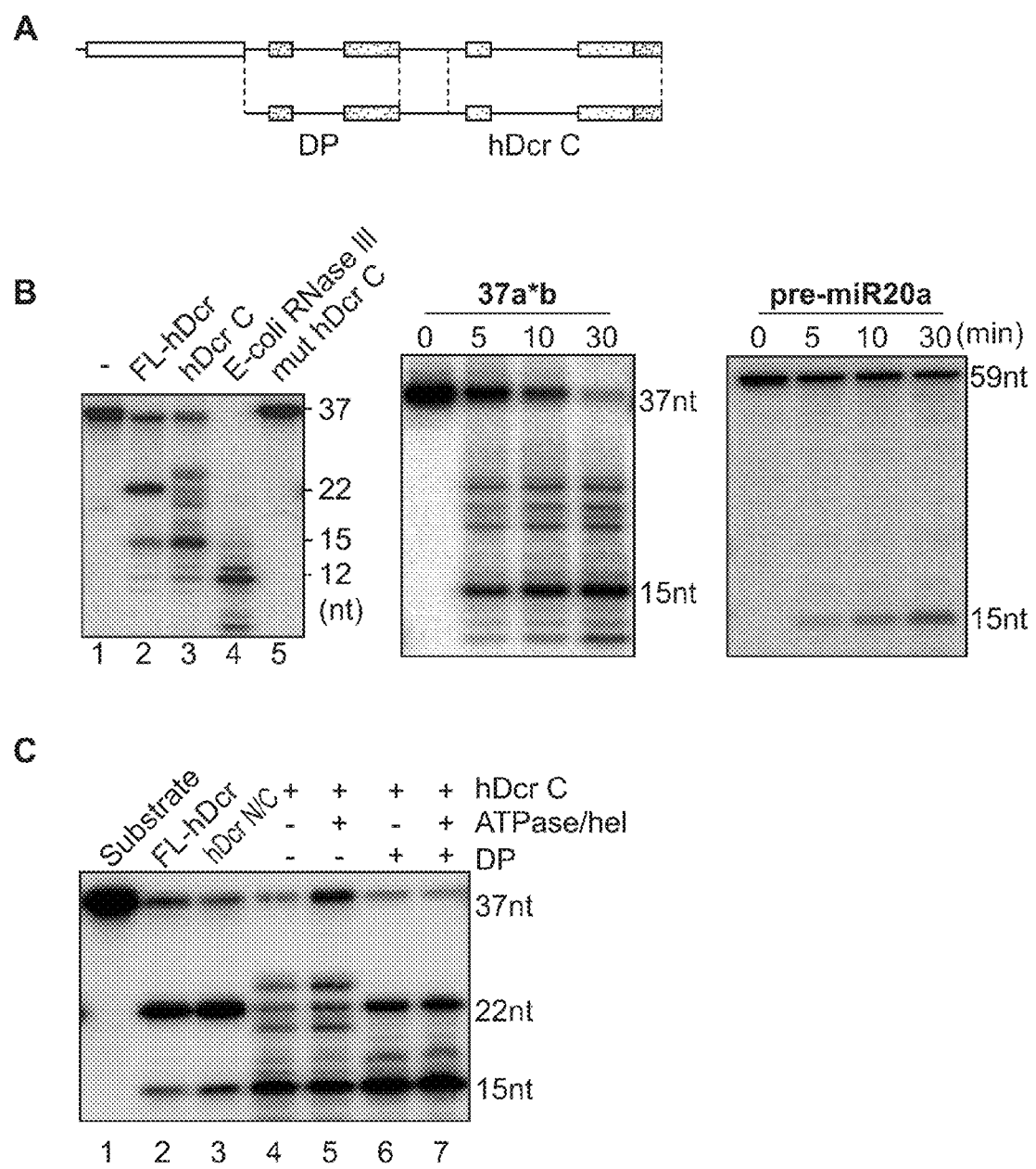
FIGS. 2A-C depict the effect of cooperative action between the PAZ and RNase III domains of hDcr on the size of dicing products.

Direct Interaction of the PAZ and RNase III Domains Determines the Length of Dicer Products The successful expression in trans of hDcr fragments in the baculovirus system encouraged us to further dissect hDcr using a bacterial expression system. It was tested whether the catalytic domains interact directly with the PAZ domain, an established RNA-binding motif that recognizes both the 5' and 3' ends at one terminus of a dsRNA (3, 6, 11-13). Based on published sequence alignment information (4, 10), hDcr-C was over-expressed in E. coli (FIG. 2A). RNA cleavage assays showed that the dominant product of the purified hDcr-C fragment is 15-nts in length, in contrast to the characteristic 22-nt products generated by full-length Dicer (lanes 2-3, left panel, FIG. 2B). For comparison, the main products generated by E. coli RNase III, a structural homolog of each of the RNase III domains of hDcr, are 12-nt in length (lane 4, left panel, FIG. 2B). Another difference is that E. coli RNase III could cleave a 19 bp substrate, but the hDcr-C could not. Further cleavage assays showed that the hDcr-C protein can also cleave hairpin RNA, for example, pre-miR-20a, in a similar manner, generating a 15-nt product (middle and right panels, FIG. 2B). To eliminate the possibility that this cleavage activity arises from RNase contamination during protein preparation, an hDcr-C protein variant containing point mutations in the two RNaseIII active sites (Glu1316Ala and Glu1705Ala) was expressed. These mutations abolished cleavage activity (lane 5, left panel, FIG. 2B).

Figure 4:
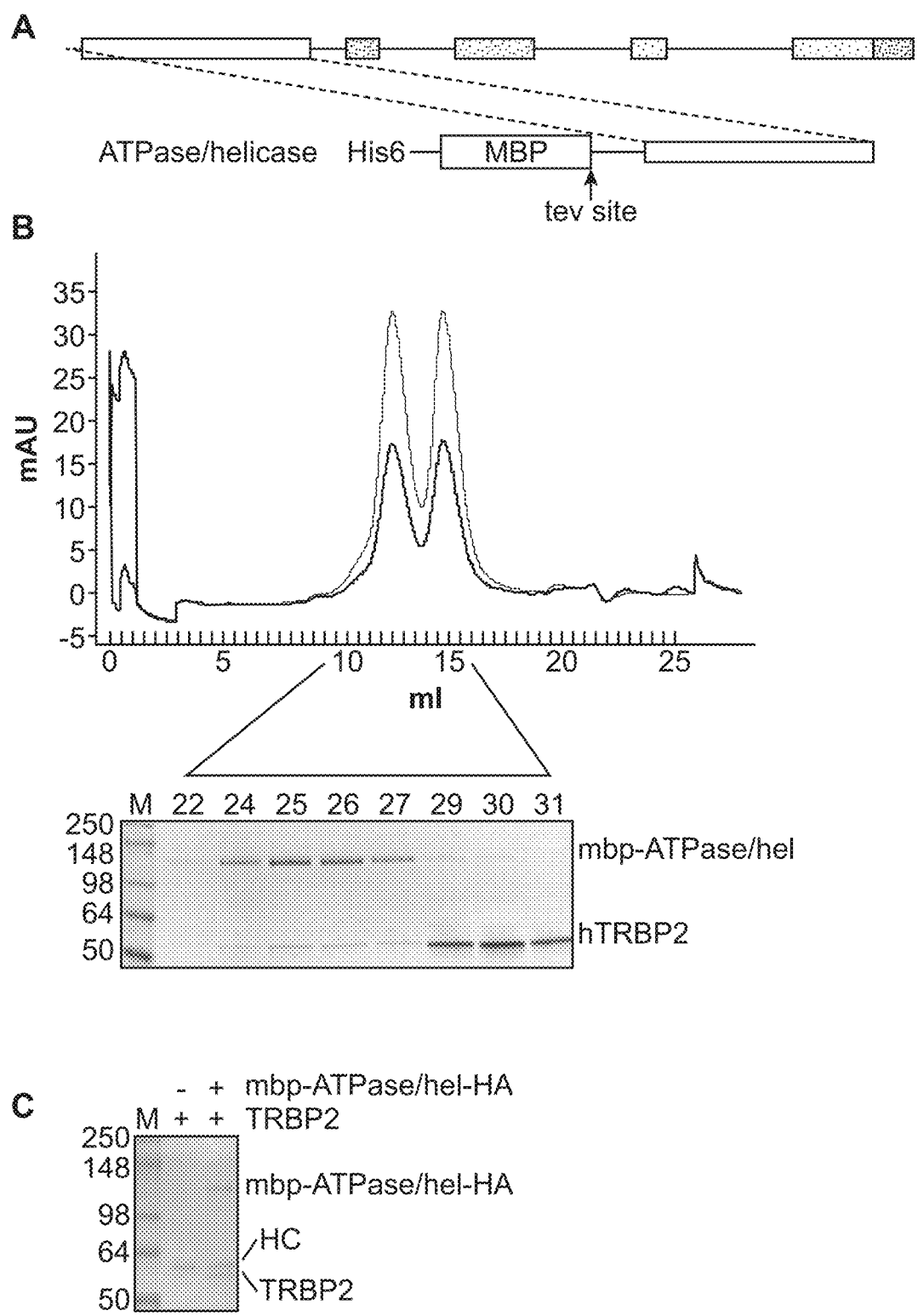
FIGS. 4A-C depict interaction of an active, bacterially expressed helicase fragment of Dicer with Trans-activation-responsive RNA-binding protein (TRBP).
Figure 7:
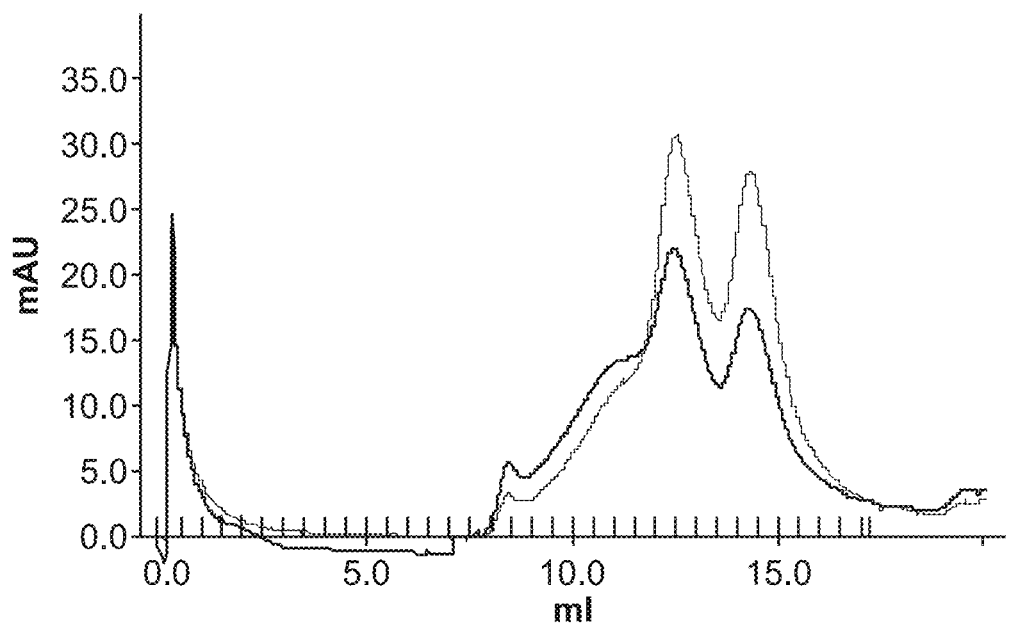
FIG. 7 depicts stable complex formation between DP and hDcr C.
Figure 7:
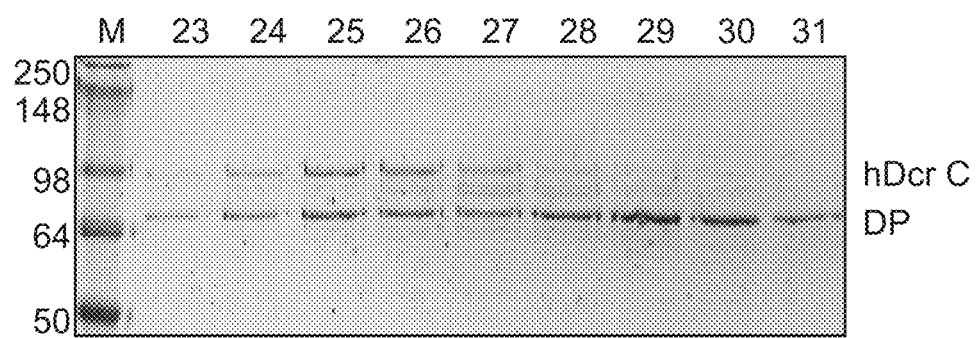

To assess the role of the PAZ domain in determining Dicer cleavage product length, an attempt was made to express the PAZ domain alone in E. coli. Although this was unsuccessful, a construct including both the PAZ domain and the adjacent DUF283 region yielded soluble protein (hereafter the tandem construct named DP, FIG. 2A). RNA cleavage assays showed that addition of the DP polypeptide to the hDcr-C cleavage reaction led to RNA products similar to those produced by full-length Dicer (lanes 6 and 7, FIG. 2C), indicating that DP and hDcr-C proteins are correctly folded and interact with each other. To test for a direct protein-protein interaction, hDcr-C and DP polypeptides were incubated together in the absence of RNA and then analyzed by size exclusion chromatography. The elution profile indicated that DP and hDcr-C form a stable complex (FIG. 7). Addition of the ATPase/Helicase domain (further discussed in FIG. 4, 5) in the cleavage reactions did not affect the cleavage pattern (lanes 3-4 or lanes 6-7, FIG. 2C). The fact that the PAZ domain binds 7-nt-long dsRNA (12, 13) and the hDcr-C generates 15-nt products suggests that the size of hDcr products (22-nt) is determined by the combined footprints of the PAZ and RNase III domains on the RNA.

FIGS. 2A-C.

Cooperative action between the PAZ and RNase III domains determines the size of hDcr products. A. Schematic representation of the bacterially expressed tandem DUF283 and PAZ domains (DP) and hDcr-C. B. Cleavage assays with hDcr-C. hDcr-C mainly generates 15-nt products from a dsRNA (lane 3), while E. coli RNase III gives 12-nt products (lane 4). As a negative control, hDcr-C with mutations in the active site glutamines (1316(E/A) and 1705(E/A)) in the RNase III domains (mthDcr-C) displayed no activity (lane 5). Middle and right panels are the cleavage assays of hDcr-C on a dsRNA (37ab) and a pre-microRNA (pre-miR-20a). In both cases, hDcr-C mainly generates a 15-nt product. C. PAZ and RNase III domains together determine the size of hDcr product. Addition of the middle domains of hDcr (DP) to the cleavage reaction (lane 6-7) restored dicing patterns displayed by FL-hDcr (compare lanes 2-3 to lanes 6-7). ATPase/hel domain played no role in cleavage activity (compare lane 4 to lane 5, or lane 6 to lane 7). FL-hDcr (lane 2) and hDcr-N/hDcr-C complex (lane 3) were used as positive controls, which generate the 22-nt and 15-nt products. The RNA substrate used in these assays was 37ab RNA, of which 37a was 5'-$^{32}$P-labeled.

FIG. 7.

DP forms a stable complex with hDcr-C. A pre-incubated mixture of the hDcr-C fragment with 3-fold excess of DP was analyzed with a Superdex 200 size-exclusion column (top panel, elution profile). SDS/PAGE analysis of the Superdex 200 fractions indicates that both proteins are present in the first peak and the excess DP elutes in the second peak (bottom panel).

The C-Terminal dsRBD is Required for RNA Substrate Binding and Cleavage Activities of hDcr-C It has been reported that the dsRBD of E. coli RNase III is not required for substrate cleavage (14), while this domain is necessary for the activity of human Drosha, another RNase III family enzyme in the microRNA pathway (8). To assess the importance of the C-terminal dsRBD in the hDcr-C construct, the hDcr-C lacking this dsRBD was expressed (hDcr-CARBD, FIG. 3A). The analysis showed that the hDcr-CARBD protein alone had no cleavage activity (lanes 1-2, FIG. 3B), indicating that the terminal dsRBD could be necessary for hDcr-C to bind or cleave dsRNA. To test whether the bacteria-expressed hDcr-CARBD retains its native fold and catalytic capability, dsRNA cleavage assays were performed by addition of the DP polypeptide to the cleavage reactions. These assays showed that the presence of DP restored the dicing pattern of hDcr (lanes 3-4, FIG. 3B). It was also found that deletion of the dsRBD from hDcr-C did not affect the complex formation of the hDcr-CARBD with DP. Therefore, the terminal dsRBD is necessary for substrate cleavage by the hDcr-C fragment, but does not affect the folding or catalytic function of the RNaseIII domains.

Figure 3:
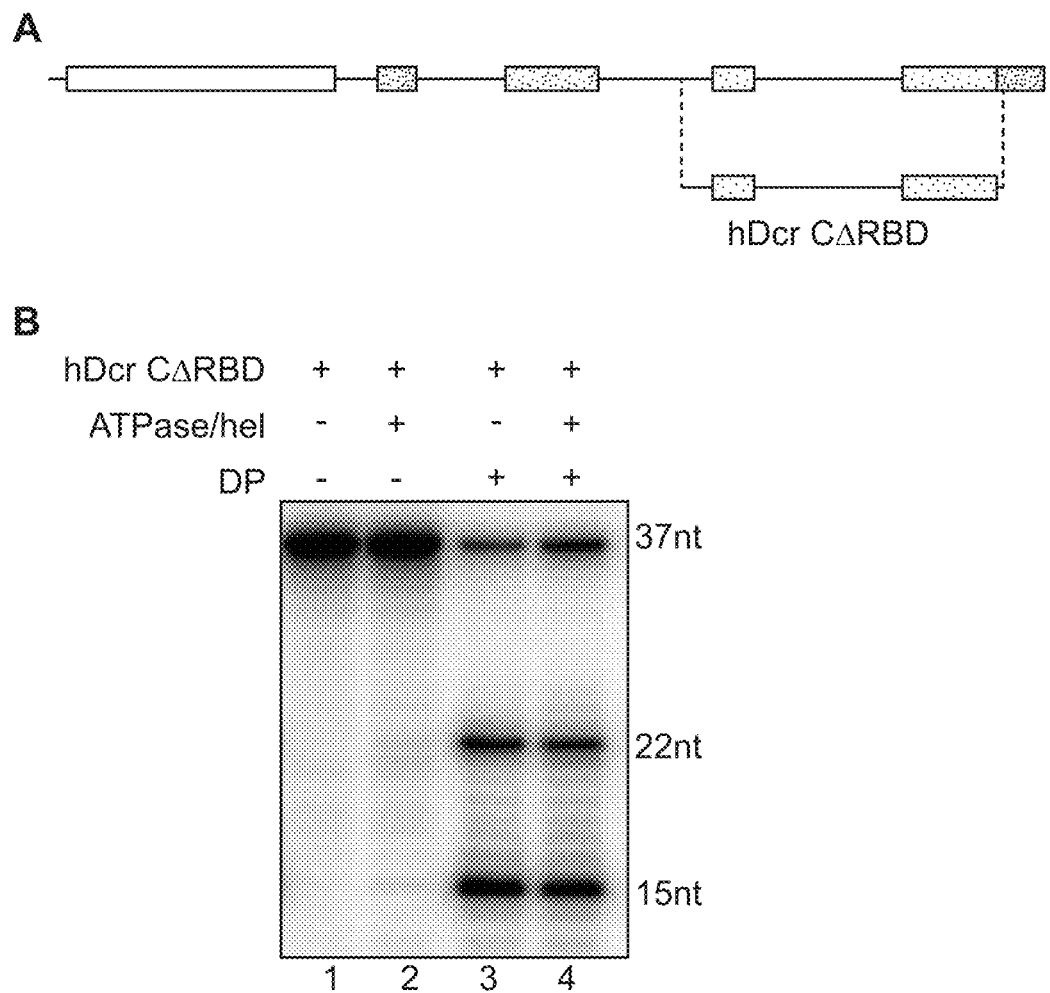
FIGS. 3A and 3B depict requirement of the C-terminal dsRBD for RNA binding and cleavage in the absence of the PAZ domain.

FIGS. 3A and 3B. The C-Terminal dsRBD is Required for RNA Binding and Cleavage in the Absence of the PAZ Domain.

A. Schematic representation of bacterially expressed hDcr-C without the C-terminal dsRBD (hDcr-CARBD). B. Requirement of dsRBD for the cleavage activity of hDcr-C. Deletion of dsRBD from hDcr-C fragment abolishes its substrate cleavage activity (lane 1-2). Addition of the middle domains of hDcr (DP) into the cleavage reactions restored FL-hDcr cleavage pattern (lanes 3-4). The ATPase/helicase domain played no role in the cleavage activity (compare lane 1 to lane 2, or lane 3 to lane 4).

To establish the relationship between cleavage activity and substrate binding, nitrocellulose filter-binding assays were performed with three kinds of RNAs under non-cleavage conditions: substrate dsRNA (37 ab), Dicer product-mimic dsRNA (19-bp) and a pre-miRNA (pre-hlet-7a-1). The DP fragment bound more strongly to perfectly matched dsRNAs (either substrate or product RNAs) than to the hairpin pre-miRNA ($K_d$~200 nM versus ~1 µM, Table 1). By contrast, the hDcr-C fragment bound with measurable affinity only to the substrate dsRNA ($K_d$~300 nM) and displayed almost no binding to either the hairpin or product RNAs (Table 1). These RNA binding data are consistent with the above cleavage results showing that the hDcr-C protein is more active towards long, perfectly matched dsRNA substrates relative to pre-miRNAs. Removal of the terminal dsRBD domain from hDcr-C abolishes its RNA binding ability, indicating that this domain is required for the binding activity of hDcr to dsRNA in the absence of PAZ domain (Table 1)

TABLE 1

| $K_D$ values (nM) for human Dicer proteins* | | | |
|---|---|---|---|
| RNA substrate | pre-hlet7a-1 | 37ab | 21ab |
| FL-hDicer | 39 ± 5 | 53 ± 8 | 144 ± 23 |
| mbp-ATPase/hel | 96 ± 10 | 476 ± 30 | n.d. |
| DP | ~1000 | 200 ± 34 | 220 ± 40 |
| hDcr C | n.d. | 300 ± 40 | n.d. |
| hDcr CARBD | n.d. | n.d. | n.d. |

*n.d. = out of the detectable limit

The hDcr ATPase/Hel Domain is Important for Substrate Selectivity Towards Pre-miRNAs Based on our previous results, it was concluded that the C-terminal hDcr fragment binds and cleaves perfect duplexes preferentially over hairpin RNAs (FIG. 2B). However, wild-type hDcr prefers to bind and cleave hairpin RNAs (7, 9). It was hypothesized that the hDcr-N polypeptide, which includes the ATPase/hel, DUF, and PAZ domains, might play a role in pre-miRNA processing. Although this fragment could not be expressed on its own either in insect cells or in *E. coli*, a construct containing the complete ATPase/helicase domain of hDcr fused with maltose-binding protein (MBP) that could be produced in *E. coli* was identified (FIG. 4A).

Figure 8:
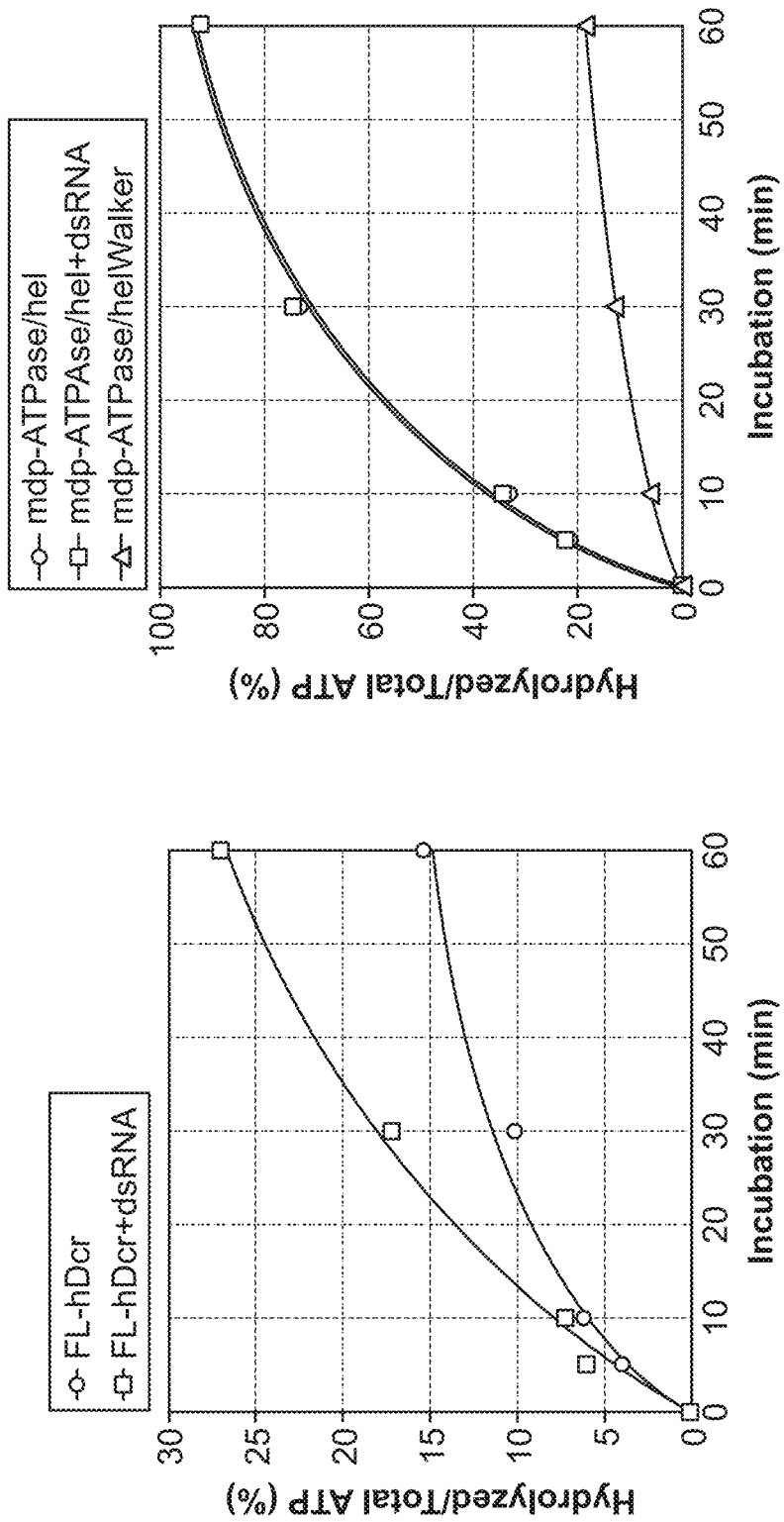
FIG. 8 depicts ATPase activity of FL-hDcr and MBP-ATPase/hel.

Since hDcr interacts with human TAR-RNA binding protein (hTRBP2) via its helicase domain (15-18), whether the MBP-ATPase/hel fusion retains the ability to bind to the recombinant hTRBP2 was tested. Both size exclusion chromatography and co-immunoprecipitation assays showed that the helicase domain interacts with hTRBP2 (FIG. 4B, C), indicating that the purified MBP-ATPase/hel protein is likely to be correctly folded. Furthermore, ATP hydrolysis assays showed that the ATPase/hel domain of hDcr retained its ability to hydrolyze ATP in vitro. FIG. 8.

It was previously demonstrated that wild-type hDcr prefers to cleave the pre-hlet7a-1 RNA relative to a perfectly matched duplex RNA substrate (7, 9). Furthermore, it has also been reported that the ATPase/hel domain is involved in the production of siRNAs from long dsRNA substrates (19, 20). To further understand the role of the helicase domain in the processing of RNA substrates, the substrate binding properties of the MBP-ATPase/hel protein were studied using filter binding assays. The helicase domain prefers to bind to the pre-hlet-7a-1 substrate with a $K_d$ of ~100 nM for the hairpin RNA. In contrast, the helicase domain bound the 37ab RNA with a Kd of ~500 nM, while it did not bind appreciably to a 21 nt RNA (Table 1).

FIGS. 4A-C.

ATPase/Helicase domain of hDcr interacts with TRBP. A. Schematic representation of bacterially expressed ATPase/hel domain tagged with MBP. B. The interaction of MBP-ATPase/hel fragment with hTRBP2. A pre-incubated mixture of the MBP-ATPase/hel fragment with 3-fold excess of hTRBP2 was fractionated with a Superdex 200 size-exclusion column (top panel, elution profile). SDS/PAGE gel analysis of the Superdex 200 fractions indicates that MBP-ATPase/hel and hTRBP2 interact as shown in the first peak (bottom panel). The excess hTRBP2 elutes in the second peak. C. MBP-ATPase/hel can pull-down hTRBP2. The MBP-ATPase/hel-domain was purified with a C-terminal hemagglutinin (HA) epitope tag. The two purified proteins (30 pmol of hDcr and 130 pmol of hTRBP2) were incubated on ice with anti-HA antibody agarose beads (Sigma-Aldrich) for 60 min prior to several washes. The bound proteins are eluted via boiling with 1.2×SDS buffer. HC is the antibody heavy chain, while the light chain was run out. M is prestained protein ladder, SeeBlue Plus2 (Invitrogen).

FIG. 8. ATPase Activity of FL-hDcr and MBP-ATPase/hel.

Quantitation of ATPase activities of FL-hDcr and MBP-ATPase/Hel are determined via TLC analyses. The ATPase activity of FL-hDcr can be moderately stimulated by dsRNA (left panel), while the activity of MBP-ATPase/Hel is not (right panel).

Figure 5:
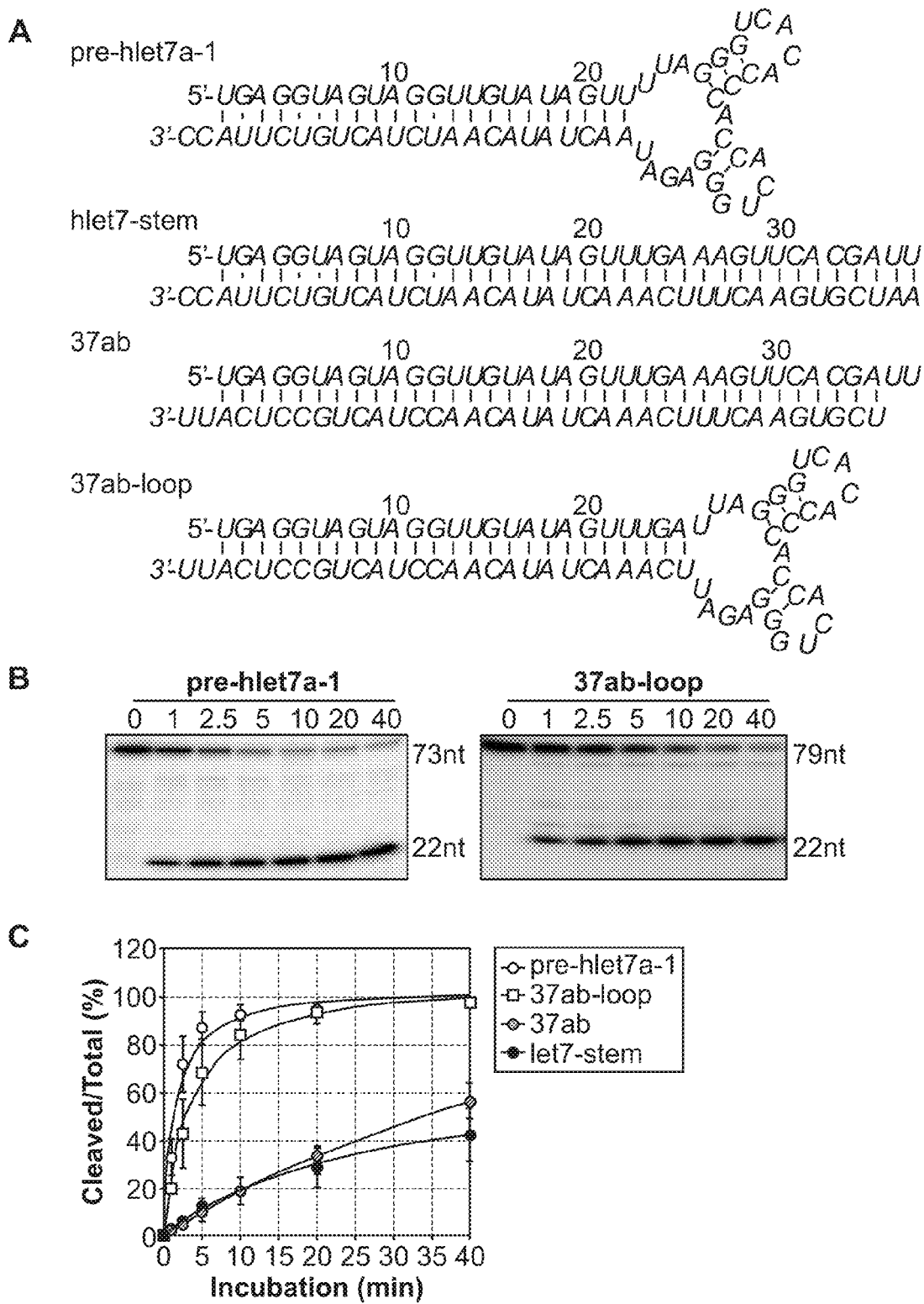
FIGS. 5A and 5B depict the effect of interaction ATPase/helicase domain with hairpin loop on the substrate selection of human Dicer. Pre-hlet7a-1: SEQ ID NO:9; hlet7-stem upper strand (5' strand): SEQ ID NO:10; hlet7-stem lower strand (3' strand): SEQ ID NO:11; 37ab upper strand (5' strand): SEQ ID NO:10; 37ab lower strand (3' strand): SEQ ID NO:12; 37ab-loop: SEQ ID NO:13.

The preferred binding of the helicase domain to pre-hlet-7a-1 may reflect the existence of an interaction between the helicase domain and the terminal loop, and this interaction may play an important role in the selection of this type of RNA substrate by hDcr. To test this possibility, a hairpin RNA (37ab-loop, FIG. 5A) was designed, containing the perfectly matched stem derived from the 37ab RNA substrate (a slow-cleavable RNA) and the terminal loop from pre-hlet-7a-1 (a fast-cleavable RNA). Dicing assays showed that hDcr cleaves the 37ab-loop substrate with a rate similar to that observed for the wild-type pre-hlet-7a-1 RNA (FIG. 5B, 5C). Specifically, under single-turnover conditions, the time required to cleave 50% of the labeled substrate ($t_{1/2}$) was approximately 1 min, 3 min, and 65 min for pre-hlet-7a-1, 37ab-loop, and 37ab, respectively (left panel, FIG. 5C). Furthermore, a bulged substrate RNA (hlet7-stem) that is derived from pre-hlet7a-1 became an unfavorable substrate, with a cleavage pattern similar to the 37 ab RNA substrate (left panel, FIG. 5C). In addition, the hDcr without the helicase domain, however, hydrolyzed all of the substrates (perfectly matched or bulged dsRNA, or pre-miRNA) in a similar manner (right panel, FIG. 5C). Taken together with above binding data, these results suggest that the ATPase/hel domain plays the role of a "gatekeeper" in order to screen RNA substrates and that its interaction with the terminal loop, not the bulged stem, regulates the dicing activity of hDcr on pre-hlet-7a-1.

FIGS. 5A and 5B.

Terminal loop of pre-hlet-7a-1 determines the substrate selection by interacting with the ATPase/helicase domain. A. Schematic representation of four RNA substrates: pre-hlet-7a-1 is abbreviated from human pre-let-7a-1; hlet7-stem is constructed from pre-hlet-7a-1 stem plus an additional 15 bps; 37ab represents a pre-siRNA; and 37ab-loop is an artificial hairpin RNA made of the 37ab stem and the terminal loop from pre-hlet-7a-1. The perfect base pairs are depicted with vertical lines in the cartoon, while G-U wobbles are marked with dots. The terminal loop structure is predicted from MFOLD and marked with grey color. B. Actual cleavage images of a natural hair RNA (pre-hlet-7a-1) and an artificial hairpin RNA (37ab-loop). These two hairpin RNAs have same terminal loop and they were cleaved similarly by wild-type hDcr. C. Interaction of terminal loop with ATPase/helicase domain determines processing activity of hDcr. The top panels show images of dicing reactions from natural pre-hlet-7a-1 and an artificial hairpin RNA, 37ab-loop. The bottom panels (from left to right) are the quantitation of dicing assays from FL-hDcr and hDcr without ATPase/hel domain on the RNA substrates shown in A.

REFERENCES

1. Siomi H & Siomi M C (2009) RISC hitches onto endosome trafficking. (Translated from eng) *Nat Cell Biol* 11(9): 1049-1051.
2. Jinek M & Doudna J A (2009) A three-dimensional view of the molecular machinery of RNA interference. (Translated from eng) *Nature* 457(7228):405-412.
3. Macrae I J, et al. (2006) Structural basis for double-stranded RNA processing by Dicer. (Translated from eng) *Science* (New York, N.Y. 311(5758):195-198.
4. Zhang H, Kolb F A, Jaskiewicz L, Westhof E, & Filipowicz W (2004) Single processing center models for human Dicer and bacterial RNase III. (Translated from eng) *Cell* 118(1):57-68.
5. Nicholson R H & Nicholson A W (2002) Molecular characterization of a mouse cDNA encoding Dicer, a ribonuclease III ortholog involved in RNA interference. (Translated from eng) *Mamm Genome* 13(2):67-73.
6. Park J E, et al. (2011) Dicer recognizes the 5' end of RNA for efficient and accurate processing. (Translated from Eng) *Nature* 475(7355):201-205.

7. Ma E, MacRae I J, Kirsch J F, & Doudna J A (2008) Autoinhibition of human dicer by its internal helicase domain. (Translated from eng) *Journal of molecular biology* 380(1):237-243.
8. Han J, et al. (2004) The Drosha-DGCR8 complex in primary microRNA processing. (Translated from eng) *Genes Dev* 18(24):3016-3027.
9. Chakravarthy S, Sternberg S H, Kellenberger C A, & Doudna J A (2010) Substrate-specific kinetics of Dicer-catalyzed RNA processing. (Translated from eng) *J Mol Biol* 404(3):392-402.
10. Provost P, et al. (2002) Ribonuclease activity and RNA binding of recombinant human Dicer. (Translated from eng) *EMBO J.* 21(21):5864-5874.
11. Song J J et al. (2003) The crystal structure of the Argonaute2 PAZ domain reveals an RNA binding motif in RNAi effector complexes. (Translated from eng) *Nat Struct Biol* 10(12):1026-1032.
12. Yan K S, et al. (2003) Structure and conserved RNA binding of the PAZ domain. (Translated from eng) *Nature* 426(6965):468-474.
13. Ma J B, Ye K, & Patel D J (2004) Structural basis for overhang-specific small interfering RNA recognition by the PAZ domain. (Translated from eng) *Nature* 429(6989):318-322.
14. Sun W, Jun E, & Nicholson A W (2001) Intrinsic double-stranded-RNA processing activity of *Escherichia coli* ribonuclease III lacking the dsRNA-binding domain. *Biochemistry* 40(49):14976-14984.
15. Daniels S M, et al. (2009) Characterization of the TRBP domain required for dicer interaction and function in RNA interference. *BMC Mol Biol* 10:38.
16. Kok K H, Ng M H, Ching Y P, & Jin D Y (2007) Human TRBP and PACT directly interact with each other and associate with dicer to facilitate the production of small interfering RNA. *J Biol Chem* 282(24):17649-17657.
17. MacRae I J, Ma E, Zhou M, Robinson C V, & Doudna J A (2008) In vitro reconstitution of the human RISC-loading complex. *Proc Natl Acad Sci USA* 105(2):512-517.
18. Chendrimada T P, et al. (2005) TRBP recruits the Dicer complex to Ago9 for microRNA processing and gene silencing. *Nature* 436(7051):740-744.
19. Lee Y S, et al. (2004) Distinct roles for *Drosophila* Dicer-1 and Dicer-2 in the siRNA/miRNA silencing pathways. *Cell* 117(1):69-81.
20. Soifer H S, et al. (2008) A role for the Dicer helicase domain in the processing of thermodynamically unstable hairpin RNAs. *Nucleic acids research* 36(20):6511-6522.
21. Li T, Pavletich N P, Schulman B A, & Zheng N (2005) High-level expression and purification of recombinant SCF ubiquitin ligases. *Methods Enzymol* 398:125-142.
22. MacRae I J, Zhou K, & Doudna J A (2007) Structural determinants of RNA recognition and cleavage by Dicer. *Nat. Struct Mol Biol* 14(10):934-940.
23. Cenik E S, et al. (2011) Phosphate and R2D2 restrict the substrate specificity of Dicer-2, an ATP-driven ribonuclease. *Mol Cell* 42(2):172-184.
24. Ye X, Paroo Z, & Liu Q (2007) Functional anatomy of the *Drosophila* microRNA-generating enzyme. *J Biol Chem* 282(39):28373-28378.
25. Welker N C, et al. (2010) Dicer's helicase domain is required for accumulation of some, but not all, *C. elegans* endogenous siRNAs. *RNA* 16(5):893-903.
26. Trabucchi M, et al. (2009) The RNA-binding protein KSRP promotes the biogenesis of a subset of microRNAs. *Nature* 459(7249):1010-1014.
27. Rybak A, et al. (2008) A feedback loop comprising lin-28 and let-7 controls pre-let-7 maturation during neural stem-cell commitment. *Nat Cell Biol* 10(8):987-993.
28. Michlewski G & Caceres J F (2010) Antagonistic role of hnRNP A1 and KSRP in the regulation of let-7a biogenesis. *Nat Struct Mol Biol* 17(8):1011-1018.
29. Ferre-D'Amare A R & Scott W G (2010) Small self-cleaving ribozymes. *Cold Spring Harb Perspect Biol* 2(10):a003574.
30. Busso D, Delagoutte-Busso B, & Moras D (2005) Construction of a set Gateway-based destination vectors for high-throughput cloning and expression screening in *Escherichia coli*. *Anal Biochem* 343(2):313-321.
31. Cheng Z, Morisawa G, & Song H (2010) Biochemical characterization of human Upf1 helicase. *Methods Mol Biol* 587:327-338.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of producing a Dicer polypeptide in a prokaryotic host cell, the method comprising:
   a) expressing a first polypeptide in a first prokaryotic host cell, wherein the first polypeptide comprises an amino acid sequence having at least 85% sequence identity to:
      (i) amino acids 1-1008 of the amino acid sequence of SEQ ID NO: 1 comprising an ATPase/helicase domain, a DUF domain, and a PAZ domain,
      (ii) amino acids 1-1068 of the amino acid sequence of SEQ ID NO: 1 comprising an ATPase/helicase domain, a DUF domain, and a PAZ domain,
      (iii) amino acids 605-1008 of the amino acid sequence of SEQ ID NO: 1 comprising a DUF and a PAZ domain,
      (iv) amino acids 605-1068 of the amino acid sequence of SEQ ID NO: 1 comprising a DUF and a PAZ domain,
      (v) amino acids 886-1008 of the amino acid sequence of SEQ ID NO: 1 comprising a PAZ domain, or
      (vi) amino acids 886-1068 of the amino acid sequence of SEQ ID NO: 1 comprising a PAZ domain, and wherein said first polypeptide lacks an RNase IIIa domain and an RNase IIIb domain; and
   b) expressing a second polypeptide in the first prokaryotic host cell or in a second prokaryotic host cell, wherein the second polypeptide comprises an amino acid sequence having at least 85% sequence identity to:
      (i) amino acids 1235 to 1922 of the amino acid sequence of SEQ ID NO: 1 comprising an RNaseIIIa domain, and RNaseIIIb domain, and a dsRBD domain),
      (ii) amino acids 1296 to 1922 of the amino acid sequence of SEQ ID NO: 1 comprising an RNaseIIIa domain, an RNaseIIIb domain, and dsRBD domain),
      (iii) amino acids 1235 to 1772 of the amino acid sequence of SEQ ID NO: 1 comprising an RNaseIIIa and RNaseIIIb domain, or
      (iv) amino acids 1296 to 1772 of the amino acid sequence of SEQ ID NO: 1 comprising an RNaseIIIa and an RNaseIIIb domain, and wherein said second polypeptide lacks at least one of: a DUF domain and a PAZ domain, wherein said first and second polypeptides spontaneously associate to form an enzymatically active Dicer complex that has endoribonuclease activity.

2. The method of claim 1, wherein the second polypeptide is expressed in the first prokaryotic host cell.

3. The method of claim 1, wherein the second polypeptide is expressed in the second prokaryotic host cell.

4. The method of claim 1, further comprising purifying the Dicer complex from the first and/or the second prokaryotic host cell.

5. The method of claim 1, wherein the prokaryotic host cell is *Escherichia coli*.

6. The method of claim 1, wherein the first polypeptide lacks amino acids 1-604 of the amino acid sequence of SEQ ID NO: 1 (a DExD/H-box domain).

7. A genetically modified prokaryotic host cell, wherein the prokaryotic host cell is genetically modified with a first recombinant expression vector comprising a nucleotide sequence encoding a first polypeptide, wherein said first polypeptide comprises an amino acid sequence having at least 85% sequence identity to:
   (i) amino acids 1-1008 of the amino acid sequence of SEQ ID NO: 1 comprising an ATPase/helicase domain, a DUF domain, and a PAZ domain,
   (ii) amino acids 1-1068 of the amino acid sequence of SEQ ID NO: 1 comprising an ATPase/helicase domain, a DUF domain, and a PAZ domain,
   (iii) amino acids 605-1008 of the amino acid sequence of SEQ ID NO: 1 comprising a DUF and a PAZ domain,
   (iv) amino acids 605-1068 of the amino acid sequence of SEQ ID NO: 1 comprising a DUF and a PAZ domain,
   (v) amino acids 886-1008 of the amino acid sequence of SEQ ID NO: 1 comprising a PAZ domain, or
   (vi) amino acids 886-1068 of the amino acid sequence of SEQ ID NO: 1 comprising a PAZ domain, and wherein said first polypeptide lacks an RNase IIIa domain and an RNase IIIb domain.

8. The genetically modified prokaryotic host cell of claim 7, wherein the prokaryotic host cell is further genetically modified with a second recombinant expression vector comprising a nucleotide sequence encoding a second polypeptide, wherein said second polypeptide comprises an amino acid sequence having at least 85% sequence identity to:
   (i) amino acids 1235 to 1922 of the amino acid sequence of SEQ ID NO: 1 comprising an RNaseIIIa domain, and RNaseIIIb domain, and a dsRBD domain,
   (ii) amino acids 1296 to 1922 of the amino acid sequence of SEQ ID NO: 1 comprising an RNaseIIIa domain, an RNaseIIIb domain, and dsRBD domain,
   (iii) amino acids 1235 to 1772 of the amino acid sequence of SEQ ID NO: 1 comprising an RNaseIIIa and RNaseIIIb domain, or
   (iv) amino acids 1296 to 1772 of the amino acid sequence of SEQ ID NO: 1 an RNaseIIIa and an RNaseIIIb domain, and wherein said second polypeptide lacks at least one of: a DUF domain and a PAZ domain, wherein said first and second polypeptides spontaneously associate to form an enzymatically active Dicer complex.

9. A genetically modified prokaryotic host cell, wherein the prokaryotic host cell is genetically modified with a recombinant expression vector comprising a nucleotide sequence encoding a second polypeptide, wherein said second polypeptide comprises an amino acid sequence having at least 85% sequence identity to:
   (i) amino acids 1235 to 1922 of the amino acid sequence of SEQ ID NO: 1 comprising an RNaseIIIa domain, and RNaseIIIb domain, and a dsRBD domain,
   (ii) amino acids 1296 to 1922 of the amino acid sequence of SEQ ID NO: 1 comprising an RNaseIIIa domain, an RNaseIIIb domain, and dsRBD domain,
   (iii) amino acids 1235 to 1772 of the amino acid sequence of SEQ ID NO: 1 comprising an RNaseIIIa and RNaseIIIb domain, or
   (iv) amino acids 1296 to 1772 of the amino acid sequence of SEQ ID NO: 1 comprising an RNaseIIIa and an RNaseIIIb domain, and wherein said second polypeptide lacks at least one of: a DUF domain and a PAZ domain.

10. A kit comprising:
   a) a first recombinant expression vector comprising a nucleotide sequence encoding a first polypeptide, wherein said first polypeptide comprises an amino acid sequence having at least 85% sequence identity to:
      (i) amino acids 1-1008 of the amino acid sequence of SEQ ID NO: 1 comprising an ATPase/helicase domain, a DUF domain, and a PAZ domain,
      (ii) amino acids 1-1068 of the amino acid sequence of SEQ ID NO: 1 comprising an ATPase/helicase domain, a DUF domain, and a PAZ domain,
      (iii) amino acids 605-1008 of the amino acid sequence of SEQ ID NO: 1 comprising a DUF and a PAZ domain,
      (iv) amino acids 605-1068 of the amino acid sequence of SEQ ID NO: 1 comprising a DUF and a PAZ domain, (v) amino acids 886-1008 of the amino acid sequence of SEQ ID NO: 1 comprising a PAZ domain, or
(vi) amino acids 886-1068 of the amino acid sequence of SEQ ID NO: 1 comprising a PAZ domain, and wherein said first polypeptide lacks an RNase IIIa domain and an RNase IIIb domain; and
b) a second recombinant expression vector comprising a nucleotide sequence encoding a second polypeptide, wherein said second polypeptide comprises amino acid sequence having at least 85% sequence identity to:
(i) amino acids 1235 to 1922 of the amino acid sequence of SEQ ID NO: 1 comprising an RNaseIIIa domain, and RNaseIIIb domain, and a dsRBD domain,
(ii) amino acids 1296 to 1922 of the amino acid sequence of SEQ ID NO: 1 comprising an RNaseIIIa domain, an RNaseIIIb domain, and dsRBD domain,
(iii) amino acids 1235 to 1772 of the amino acid sequence of SEQ ID NO: 1 comprising an RNaseIIIa and RNaseIIIb domain, or
(iv) amino acids 1296 to 1772 of the amino acid sequence of SEQ ID NO: 1 comprising an RNaseIIIa and an RNaseIIIb domain, and wherein said second polypeptide lacks at least one of: a DUF domain and a PAZ domain.

11. The kit of claim 10, wherein the first polypeptide lacks amino acids 1-604 of the amino acid sequence of SEQ ID NO: 1 (a DExD/H-box domain).

12. The method of claim 1, wherein the second polypeptide lacks a double-stranded RNA binding domain.

13. The method of claim 1, wherein the second polypeptide lacks a DUF domain and a PAZ domain.

14. The genetically modified prokaryotic host cell of claim 8, wherein the second polypeptide lacks a DUF domain and a PAZ domain.

15. The genetically modified prokaryotic host cell of claim 9, wherein the second polypeptide lacks a DUF domain and a PAZ domain.

16. The kit of claim 10, wherein the second polypeptide lacks a DUF domain and a PAZ domain.

17. The method of claim 1, wherein at least one of the first and second polypeptides further comprises a heterologous polypeptide that provides for a detectable signal and/or facilitates protein purification or isolation.

18. The genetically modified prokaryotic host cell of claim 7, wherein the first polypeptide further comprises a heterologous polypeptide that provides for a detectable signal and/or facilitates protein purification or isolation.

19. The genetically modified prokaryotic host cell of claim 8, wherein at least one of the first and second polypeptides further comprises a heterologous polypeptide that provides for a detectable signal and/or facilitates protein purification or isolation.

20. The genetically modified prokaryotic host cell of claim 9, wherein the second polypeptide further comprises a heterologous polypeptide that provides for a detectable signal and/or facilitates protein purification or isolation.

21. The kit of claim 10, wherein at least one of the first and second polypeptides further comprises a heterologous polypeptide that provides for a detectable signal and/or facilitates protein purification or isolation.

* * * * *

SEQUENCE LISTING

<160> NUMBER OF SEQ ID NOS: 23

<210> SEQ ID NO 1
<211> LENGTH: 1922
<212> TYPE: PRT
<213> ORGANISM: Homo sapiens

<400> SEQUENCE: 1

```
Met Lys Ser Pro Ala Leu Gln Pro Leu Ser Met Ala Gly Leu Gln Leu
 1               5                  10                  15

Met Thr Pro Ala Ser Ser Pro Met Gly Pro Phe Phe Gly Leu Pro Trp
             20                  25                  30

Gln Gln Glu Ala Ile His Asp Asn Ile Tyr Thr Pro Arg Lys Tyr Gln
         35                  40                  45

Val Glu Leu Leu Glu Ala Ala Leu Asp His Asn Thr Ile Val Cys Leu
     50                  55                  60
```

```
Asn Thr Gly Ser Gly Lys Thr Phe Ile Ala Val Leu Leu Thr Lys Glu
 65                  70                  75                  80

Leu Ser Tyr Gln Ile Arg Gly Asp Phe Ser Arg Asn Gly Lys Arg Thr
                 85                  90                  95

Val Phe Leu Val Asn Ser Ala Asn Gln Val Ala Gln Gln Val Ser Ala
                100                 105                 110

Val Arg Thr His Ser Asp Leu Lys Val Gly Glu Tyr Ser Asn Leu Glu
                115                 120                 125

Val Asn Ala Ser Trp Thr Lys Glu Arg Trp Asn Gln Glu Phe Thr Lys
130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
                180                 185                 190

Cys Glu Asn Cys Pro Ser Cys Pro Arg Ile Leu Gly Leu Thr Ala Ser
                195                 200                 205

Ile Leu Asn Gly Lys Cys Asp Pro Glu Glu Leu Glu Glu Lys Ile Gln
210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
                260                 265                 270

Glu Leu Glu Glu Ala Leu Asn Phe Ile Asn Asp Cys Asn Ile Ser Val
                275                 280                 285

His Ser Lys Glu Arg Asp Ser Thr Leu Ile Ser Lys Gln Ile Leu Ser
                290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Phe Leu
                340                 345                 350

Arg Lys Ile His Ala Leu Cys Glu Glu His Phe Ser Pro Ala Ser Leu
                355                 360                 365

Asp Leu Lys Phe Val Thr Pro Lys Val Ile Lys Leu Leu Glu Ile Leu
                370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Glu Asp Glu Glu Ile Glu Glu Lys Glu Lys Pro Glu Thr
                420                 425                 430

Asn Phe Pro Ser Pro Phe Thr Asn Ile Leu Cys Gly Ile Ile Phe Val
                435                 440                 445

Glu Arg Arg Tyr Thr Ala Val Val Leu Asn Arg Leu Ile Lys Glu Ala
                450                 455                 460

Gly Lys Gln Asp Pro Glu Leu Ala Tyr Ile Ser Ser Asn Phe Ile Thr
465                 470                 475                 480
```

```
Gly His Gly Ile Gly Lys Asn Gln Pro Arg Asn Lys Gln Met Glu Ala
                    485                 490                 495

Glu Phe Arg Lys Gln Glu Glu Val Leu Arg Lys Phe Arg Ala His Glu
            500                 505                 510

Thr Asn Leu Leu Ile Ala Thr Ser Ile Val Glu Glu Gly Val Asp Ile
            515                 520                 525

Pro Lys Cys Asn Leu Val Val Arg Phe Asp Leu Pro Thr Glu Tyr Arg
            530                 535                 540

Ser Tyr Val Gln Ser Lys Gly Arg Ala Arg Ala Pro Ile Ser Asn Tyr
545                 550                 555                 560

Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
            580                 585                 590

Ser Val Asp Thr Gly Glu Thr Asp Ile Asp Pro Val Met Asp Asp Asp
            595                 600                 605

Asp Val Phe Pro Pro Tyr Val Leu Arg Pro Asp Asp Gly Gly Pro Arg
            610                 615                 620

Val Thr Ile Asn Thr Ala Ile Gly His Ile Asn Arg Tyr Cys Ala Arg
625                 630                 635                 640

Leu Pro Ser Asp Pro Phe Thr His Leu Ala Pro Lys Cys Arg Thr Arg
                645                 650                 655

Glu Leu Pro Asp Gly Thr Phe Tyr Ser Thr Leu Tyr Leu Pro Ile Asn
                660                 665                 670

Ser Pro Leu Arg Ala Ser Ile Val Gly Pro Pro Met Ser Cys Val Arg
            675                 680                 685

Leu Ala Glu Arg Val Val Ala Leu Ile Cys Cys Glu Lys Leu His Lys
            690                 695                 700

Ile Gly Glu Leu Asp Asp His Leu Met Pro Val Gly Lys Glu Thr Val
705                 710                 715                 720

Lys Tyr Glu Glu Glu Leu Asp Leu His Asp Glu Glu Thr Ser Val
                725                 730                 735

Pro Gly Arg Pro Gly Ser Thr Lys Arg Arg Gln Cys Tyr Pro Lys Ala
            740                 745                 750

Ile Pro Glu Cys Leu Arg Asp Ser Tyr Pro Arg Pro Asp Gln Pro Cys
            755                 760                 765

Tyr Leu Tyr Val Ile Gly Met Val Leu Thr Thr Pro Leu Pro Asp Glu
            770                 775                 780

Leu Asn Phe Arg Arg Lys Leu Tyr Pro Pro Glu Asp Thr Thr Arg
785                 790                 795                 800

Cys Phe Gly Ile Leu Thr Ala Lys Pro Ile Pro Gln Ile Pro His Phe
                805                 810                 815

Pro Val Tyr Thr Arg Ser Gly Glu Val Thr Ile Ser Ile Glu Leu Lys
            820                 825                 830

Lys Ser Gly Phe Met Leu Ser Leu Gln Met Leu Glu Leu Ile Thr Arg
            835                 840                 845

Leu His Gln Tyr Ile Phe Ser His Ile Leu Arg Leu Glu Lys Pro Ala
            850                 855                 860

Leu Glu Phe Lys Pro Thr Asp Ala Asp Ser Ala Tyr Cys Val Leu Pro
865                 870                 875                 880

Leu Asn Val Val Asn Asp Ser Ser Thr Leu Asp Ile Asp Phe Lys Phe
                885                 890                 895

Met Glu Asp Ile Glu Lys Ser Glu Ala Arg Ile Gly Ile Pro Ser Thr
```

```
                900             905             910
Lys Tyr Thr Lys Glu Thr Pro Phe Val Phe Lys Leu Glu Asp Tyr Gln
        915             920             925
Asp Ala Val Ile Ile Pro Arg Tyr Arg Asn Phe Asp Gln Pro His Arg
        930             935             940
Phe Tyr Val Ala Asp Val Tyr Thr Asp Leu Thr Pro Leu Ser Lys Phe
945             950             955             960
Pro Ser Pro Glu Tyr Glu Thr Phe Ala Glu Tyr Lys Thr Lys Tyr
            965             970             975
Asn Leu Asp Leu Thr Asn Leu Asn Gln Pro Leu Leu Asp Val Asp His
        980             985             990
Thr Ser Ser Arg Leu Asn Leu Leu Thr Pro Arg His Leu Asn Gln Lys
        995             1000            1005
Gly Lys Ala Leu Pro Leu Ser Ser Ala Glu Lys Arg Lys Ala Lys
        1010            1015            1020
Trp Glu Ser Leu Gln Asn Lys Gln Ile Leu Val Pro Glu Leu Cys
        1025            1030            1035
Ala Ile His Pro Ile Pro Ala Ser Leu Trp Arg Lys Ala Val Cys
        1040            1045            1050
Leu Pro Ser Ile Leu Tyr Arg Leu His Cys Leu Leu Thr Ala Glu
        1055            1060            1065
Glu Leu Arg Ala Gln Thr Ala Ser Asp Ala Gly Val Gly Val Arg
        1070            1075            1080
Ser Leu Pro Ala Asp Phe Arg Tyr Pro Asn Leu Asp Phe Gly Trp
        1085            1090            1095
Lys Lys Ser Ile Asp Ser Lys Ser Phe Ile Ser Ile Ser Asn Ser
        1100            1105            1110
Ser Ser Ala Glu Asn Asp Asn Tyr Cys Lys His Ser Thr Ile Val
        1115            1120            1125
Pro Glu Asn Ala Ala His Gln Gly Ala Asn Arg Thr Ser Ser Leu
        1130            1135            1140
Glu Asn His Asp Gln Met Ser Val Asn Cys Arg Thr Leu Leu Ser
        1145            1150            1155
Glu Ser Pro Gly Lys Leu His Val Glu Val Ser Ala Asp Leu Thr
        1160            1165            1170
Ala Ile Asn Gly Leu Ser Tyr Asn Gln Asn Leu Ala Asn Gly Ser
        1175            1180            1185
Tyr Asp Leu Ala Asn Arg Asp Phe Cys Gln Gly Asn Gln Leu Asn
        1190            1195            1200
Tyr Tyr Lys Gln Glu Ile Pro Val Gln Pro Thr Thr Ser Tyr Ser
        1205            1210            1215
Ile Gln Asn Leu Tyr Ser Tyr Glu Asn Gln Pro Gln Pro Ser Asp
        1220            1225            1230
Glu Cys Thr Leu Leu Ser Asn Lys Tyr Leu Asp Gly Asn Ala Asn
        1235            1240            1245
Lys Ser Thr Ser Asp Gly Ser Pro Val Met Ala Val Met Pro Gly
        1250            1255            1260
Thr Thr Asp Thr Ile Gln Val Leu Lys Gly Arg Met Asp Ser Glu
        1265            1270            1275
Gln Ser Pro Ser Ile Gly Tyr Ser Ser Arg Thr Leu Gly Pro Asn
        1280            1285            1290
Pro Gly Leu Ile Leu Gln Ala Leu Thr Leu Ser Asn Ala Ser Asp
        1295            1300            1305
```

-continued

Gly Phe Asn Leu Glu Arg Leu Glu Met Leu Gly Asp Ser Phe Leu
1310              1315              1320

Lys His Ala Ile Thr Thr Tyr Leu Phe Cys Thr Tyr Pro Asp Ala
1325              1330              1335

His Glu Gly Arg Leu Ser Tyr Met Arg Ser Lys Lys Val Ser Asn
1340              1345              1350

Cys Asn Leu Tyr Arg Leu Gly Lys Lys Lys Gly Leu Pro Ser Arg
1355              1360              1365

Met Val Val Ser Ile Phe Asp Pro Pro Val Asn Trp Leu Pro Pro
1370              1375              1380

Gly Tyr Val Val Asn Gln Asp Lys Ser Asn Thr Asp Lys Trp Glu
1385              1390              1395

Lys Asp Glu Met Thr Lys Asp Cys Met Leu Ala Asn Gly Lys Leu
1400              1405              1410

Asp Glu Asp Tyr Glu Glu Glu Asp Glu Glu Glu Ser Leu Met
1415              1420              1425

Trp Arg Ala Pro Lys Glu Glu Ala Asp Tyr Glu Asp Asp Phe Leu
1430              1435              1440

Glu Tyr Asp Gln Glu His Ile Arg Phe Ile Asp Asn Met Leu Met
1445              1450              1455

Gly Ser Gly Ala Phe Val Lys Lys Ile Ser Leu Ser Pro Phe Ser
1460              1465              1470

Thr Thr Asp Ser Ala Tyr Glu Trp Lys Met Pro Lys Lys Ser Ser
1475              1480              1485

Leu Gly Ser Met Pro Phe Ser Ser Asp Phe Glu Asp Phe Asp Tyr
1490              1495              1500

Ser Ser Trp Asp Ala Met Cys Tyr Leu Asp Pro Ser Lys Ala Val
1505              1510              1515

Glu Glu Asp Asp Phe Val Val Gly Phe Trp Asn Pro Ser Glu Glu
1520              1525              1530

Asn Cys Gly Val Asp Thr Gly Lys Gln Ser Ile Ser Tyr Asp Leu
1535              1540              1545

His Thr Glu Gln Cys Ile Ala Asp Lys Ser Ile Ala Asp Cys Val
1550              1555              1560

Glu Ala Leu Leu Gly Cys Tyr Leu Thr Ser Cys Gly Glu Arg Ala
1565              1570              1575

Ala Gln Leu Phe Leu Cys Ser Leu Gly Leu Lys Val Leu Pro Val
1580              1585              1590

Ile Lys Arg Thr Asp Arg Glu Lys Ala Leu Cys Pro Thr Arg Glu
1595              1600              1605

Asn Phe Asn Ser Gln Gln Lys Asn Leu Ser Val Ser Cys Ala Ala
1610              1615              1620

Ala Ser Val Ala Ser Ser Arg Ser Ser Val Leu Lys Asp Ser Glu
1625              1630              1635

Tyr Gly Cys Leu Lys Ile Pro Pro Arg Cys Met Phe Asp His Pro
1640              1645              1650

Asp Ala Asp Lys Thr Leu Asn His Leu Ile Ser Gly Phe Glu Asn
1655              1660              1665

Phe Glu Lys Lys Ile Asn Tyr Arg Phe Lys Asn Lys Ala Tyr Leu
1670              1675              1680

Leu Gln Ala Phe Thr His Ala Ser Tyr His Tyr Asn Thr Ile Thr
1685              1690              1695

-continued

Asp Cys Tyr Gln Arg Leu Glu Phe Leu Gly Asp Ala Ile Leu Asp
    1700                1705                1710

Tyr Leu Ile Thr Lys His Leu Tyr Glu Asp Pro Arg Gln His Ser
    1715                1720                1725

Pro Gly Val Leu Thr Asp Leu Arg Ser Ala Leu Val Asn Asn Thr
    1730                1735                1740

Ile Phe Ala Ser Leu Ala Val Lys Tyr Asp Tyr His Lys Tyr Phe
    1745                1750                1755

Lys Ala Val Ser Pro Glu Leu Phe His Val Ile Asp Asp Phe Val
    1760                1765                1770

Gln Phe Gln Leu Glu Lys Asn Glu Met Gln Gly Met Asp Ser Glu
    1775                1780                1785

Leu Arg Arg Ser Glu Glu Asp Glu Glu Lys Glu Asp Ile Glu
    1790                1795                1800

Val Pro Lys Ala Met Gly Asp Ile Phe Glu Ser Leu Ala Gly Ala
    1805                1810                1815

Ile Tyr Met Asp Ser Gly Met Ser Leu Glu Thr Val Trp Gln Val
    1820                1825                1830

Tyr Tyr Pro Met Met Arg Pro Leu Ile Glu Lys Phe Ser Ala Asn
    1835                1840                1845

Val Pro Arg Ser Pro Val Arg Glu Leu Leu Glu Met Glu Pro Glu
    1850                1855                1860

Thr Ala Lys Phe Ser Pro Ala Glu Arg Thr Tyr Asp Gly Lys Val
    1865                1870                1875

Arg Val Thr Val Glu Val Val Gly Lys Gly Lys Phe Lys Gly Val
    1880                1885                1890

Gly Arg Ser Tyr Arg Ile Ala Lys Ser Ala Ala Ala Arg Arg Ala
    1895                1900                1905

Leu Arg Ser Leu Lys Ala Asn Gln Pro Gln Val Pro Asn Ser
    1910                1915                1920

<210> SEQ ID NO 2
<211> LENGTH: 604
<212> TYPE: PRT
<213> ORGANISM: Artificial sequence
<220> FEATURE:
<223> OTHER INFORMATION: Synthetic sequence

<400> SEQUENCE: 2

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ser Tyr Gln Ile Arg Gly Asp Phe Ser Arg Asn Gly Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

-continued

```
Val Asn Ala Ser Trp Thr Lys Glu Arg Trp Asn Gln Glu Phe Thr Lys
130                 135                 140
His Gln Val Leu Ile Met Thr Cys Tyr Val Ala Leu Asn Val Leu Lys
145                 150                 155                 160
Asn Gly Tyr Leu Ser Leu Ser Asp Ile Asn Leu Leu Val Phe Asp Glu
                165                 170                 175
Cys His Leu Ala Ile Leu Asp His Pro Tyr Arg Glu Ile Met Lys Leu
            180                 185                 190
Cys Glu Asn Cys Pro Ser Cys Pro Arg Ile Leu Gly Leu Thr Ala Ser
        195                 200                 205
Ile Leu Asn Gly Lys Cys Asp Pro Glu Glu Leu Glu Glu Lys Ile Gln
210                 215                 220
Lys Leu Glu Lys Ile Leu Lys Ser Asn Ala Glu Thr Ala Thr Asp Leu
225                 230                 235                 240
Val Val Leu Asp Arg Tyr Thr Ser Gln Pro Cys Glu Ile Val Val Asp
                245                 250                 255
Cys Gly Pro Phe Thr Asp Arg Ser Gly Leu Tyr Glu Arg Leu Leu Met
            260                 265                 270
Glu Leu Glu Glu Ala Leu Asn Phe Ile Asn Asp Cys Asn Ile Ser Val
        275                 280                 285
His Ser Lys Glu Arg Asp Ser Thr Leu Ile Ser Lys Gln Ile Leu Ser
290                 295                 300
Asp Cys Arg Ala Val Leu Val Val Leu Gly Pro Trp Cys Ala Asp Lys
305                 310                 315                 320
Val Ala Gly Met Met Val Arg Glu Leu Gln Lys Tyr Ile Lys His Glu
                325                 330                 335
Gln Glu Glu Leu His Arg Lys Phe Leu Leu Phe Thr Asp Thr Phe Leu
            340                 345                 350
Arg Lys Ile His Ala Leu Cys Glu Glu His Phe Ser Pro Ala Ser Leu
        355                 360                 365
Asp Leu Lys Phe Val Thr Pro Lys Val Ile Lys Leu Leu Glu Ile Leu
370                 375                 380
Arg Lys Tyr Lys Pro Tyr Glu Arg Gln Gln Phe Glu Ser Val Glu Trp
385                 390                 395                 400
Tyr Asn Asn Arg Asn Gln Asp Asn Tyr Val Ser Trp Ser Asp Ser Glu
                405                 410                 415
Asp Asp Asp Glu Asp Glu Glu Ile Glu Glu Lys Glu Lys Pro Glu Thr
            420                 425                 430
Asn Phe Pro Ser Pro Phe Thr Asn Ile Leu Cys Gly Ile Ile Phe Val
        435                 440                 445
Glu Arg Arg Tyr Thr Ala Val Val Leu Asn Arg Leu Ile Lys Glu Ala
450                 455                 460
Gly Lys Gln Asp Pro Glu Leu Ala Tyr Ile Ser Ser Asn Phe Ile Thr
465                 470                 475                 480
Gly His Gly Ile Gly Lys Asn Gln Pro Arg Asn Lys Gln Met Glu Ala
                485                 490                 495
Glu Phe Arg Lys Gln Glu Glu Val Leu Arg Lys Phe Arg Ala His Glu
            500                 505                 510
Thr Asn Leu Leu Ile Ala Thr Ser Ile Val Glu Glu Gly Val Asp Ile
        515                 520                 525
Pro Lys Cys Asn Leu Val Val Arg Phe Asp Leu Pro Thr Glu Tyr Arg
530                 535                 540
Ser Tyr Val Gln Ser Lys Gly Arg Ala Arg Ala Pro Ile Ser Asn Tyr
```

```
                 545                 550                 555                 560
Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
                580                 585                 590

Ser Val Asp Thr Gly Glu Thr Asp Ile Asp Pro Val
                595                 600

<210> SEQ ID NO 3
<211> LENGTH: 1318
<212> TYPE: PRT
<213> ORGANISM: Artificial sequence
<220> FEATURE:
<223> OTHER INFORMATION: Synthetic sequence

<400> SEQUENCE: 3

Met Asp Asp Asp Val Phe Pro Pro Tyr Val Leu Arg Pro Asp Asp
1               5                   10                  15

Gly Gly Pro Arg Val Thr Ile Asn Thr Ala Ile Gly His Ile Asn Arg
                20                  25                  30

Tyr Cys Ala Arg Leu Pro Ser Asp Pro Phe Thr His Leu Ala Pro Lys
                35                  40                  45

Cys Arg Thr Arg Glu Leu Pro Asp Gly Thr Phe Tyr Ser Thr Leu Tyr
    50                  55                  60

Leu Pro Ile Asn Ser Pro Leu Arg Ala Ser Ile Val Gly Pro Pro Met
65                  70                  75                  80

Ser Cys Val Arg Leu Ala Glu Arg Val Val Ala Leu Ile Cys Cys Glu
                85                  90                  95

Lys Leu His Lys Ile Gly Glu Leu Asp Asp His Leu Met Pro Val Gly
                100                 105                 110

Lys Glu Thr Val Lys Tyr Glu Glu Leu Asp Leu His Asp Glu Glu
                115                 120                 125

Glu Thr Ser Val Pro Gly Arg Pro Gly Ser Thr Lys Arg Arg Gln Cys
    130                 135                 140

Tyr Pro Lys Ala Ile Pro Glu Cys Leu Arg Asp Ser Tyr Pro Arg Pro
145                 150                 155                 160

Asp Gln Pro Cys Tyr Leu Tyr Val Ile Gly Met Val Leu Thr Thr Pro
                165                 170                 175

Leu Pro Asp Glu Leu Asn Phe Arg Arg Arg Lys Leu Tyr Pro Pro Glu
                180                 185                 190

Asp Thr Thr Arg Cys Phe Gly Ile Leu Thr Ala Lys Pro Ile Pro Gln
                195                 200                 205

Ile Pro His Phe Pro Val Tyr Thr Arg Ser Gly Glu Val Thr Ile Ser
    210                 215                 220

Ile Glu Leu Lys Lys Ser Gly Phe Met Leu Ser Leu Gln Met Leu Glu
225                 230                 235                 240

Leu Ile Thr Arg Leu His Gln Tyr Ile Phe Ser His Ile Leu Arg Leu
                245                 250                 255

Glu Lys Pro Ala Leu Glu Phe Lys Pro Thr Asp Ala Asp Ser Ala Tyr
                260                 265                 270

Cys Val Leu Pro Leu Asn Val Asn Asp Ser Ser Thr Leu Asp Ile
                275                 280                 285

Asp Phe Lys Phe Met Glu Asp Ile Glu Lys Ser Glu Ala Arg Ile Gly
    290                 295                 300

Ile Pro Ser Thr Lys Tyr Thr Lys Glu Thr Pro Phe Val Phe Lys Leu
```

-continued

```
            305                 310                 315                 320
        Glu Asp Tyr Gln Asp Ala Val Ile Ile Pro Arg Tyr Arg Asn Phe Asp
                        325                 330                 335
        Gln Pro His Arg Phe Tyr Val Ala Asp Val Tyr Thr Asp Leu Thr Pro
                        340                 345                 350
        Leu Ser Lys Phe Pro Ser Pro Glu Tyr Glu Thr Phe Ala Glu Tyr Tyr
                        355                 360                 365
        Lys Thr Lys Tyr Asn Leu Asp Leu Thr Asn Leu Asn Gln Pro Leu Leu
                        370                 375                 380
        Asp Val Asp His Thr Ser Ser Arg Leu Asn Leu Leu Thr Pro Arg His
        385                 390                 395                 400
        Leu Asn Gln Lys Gly Lys Ala Leu Pro Leu Ser Ser Ala Glu Lys Arg
                        405                 410                 415
        Lys Ala Lys Trp Glu Ser Leu Gln Asn Lys Gln Ile Leu Val Pro Glu
                        420                 425                 430
        Leu Cys Ala Ile His Pro Ile Pro Ala Ser Leu Trp Arg Lys Ala Val
                        435                 440                 445
        Cys Leu Pro Ser Ile Leu Tyr Arg Leu His Cys Leu Leu Thr Ala Glu
                        450                 455                 460
        Glu Leu Arg Ala Gln Thr Ala Ser Asp Ala Gly Val Gly Val Arg Ser
        465                 470                 475                 480
        Leu Pro Ala Asp Phe Arg Tyr Pro Asn Leu Asp Phe Gly Trp Lys Lys
                        485                 490                 495
        Ser Ile Asp Ser Lys Ser Phe Ile Ser Ile Ser Asn Ser Ser Ser Ala
                        500                 505                 510
        Glu Asn Asp Asn Tyr Cys Lys His Ser Thr Ile Val Pro Glu Asn Ala
                        515                 520                 525
        Ala His Gln Gly Ala Asn Arg Thr Ser Ser Leu Glu Asn His Asp Gln
                        530                 535                 540
        Met Ser Val Asn Cys Arg Thr Leu Leu Ser Glu Ser Pro Gly Lys Leu
        545                 550                 555                 560
        His Val Glu Val Ser Ala Asp Leu Thr Ala Ile Asn Gly Leu Ser Tyr
                        565                 570                 575
        Asn Gln Asn Leu Ala Asn Gly Ser Tyr Asp Leu Ala Asn Arg Asp Phe
                        580                 585                 590
        Cys Gln Gly Asn Gln Leu Asn Tyr Tyr Lys Gln Glu Ile Pro Val Gln
                        595                 600                 605
        Pro Thr Thr Ser Tyr Ser Ile Gln Asn Leu Tyr Ser Tyr Glu Asn Gln
                        610                 615                 620
        Pro Gln Pro Ser Asp Glu Cys Thr Leu Leu Ser Asn Lys Tyr Leu Asp
        625                 630                 635                 640
        Gly Asn Ala Asn Lys Ser Thr Ser Asp Gly Ser Pro Val Met Ala Val
                        645                 650                 655
        Met Pro Gly Thr Thr Asp Thr Ile Gln Val Leu Lys Gly Arg Met Asp
                        660                 665                 670
        Ser Glu Gln Ser Pro Ser Ile Gly Tyr Ser Ser Arg Thr Leu Gly Pro
                        675                 680                 685
        Asn Pro Gly Leu Ile Leu Gln Ala Leu Thr Leu Ser Asn Ala Ser Asp
                        690                 695                 700
        Gly Phe Asn Leu Glu Arg Leu Glu Met Leu Gly Asp Ser Phe Leu Lys
        705                 710                 715                 720
        His Ala Ile Thr Thr Tyr Leu Phe Cys Thr Tyr Pro Asp Ala His Glu
                        725                 730                 735
```

-continued

```
Gly Arg Leu Ser Tyr Met Arg Ser Lys Lys Val Ser Asn Cys Asn Leu
            740                 745                 750

Tyr Arg Leu Gly Lys Lys Gly Leu Pro Ser Arg Met Val Val Ser
            755                 760                 765

Ile Phe Asp Pro Pro Val Asn Trp Leu Pro Pro Gly Tyr Val Val Asn
            770                 775                 780

Gln Asp Lys Ser Asn Thr Asp Lys Trp Glu Lys Asp Glu Met Thr Lys
785                 790                 795                 800

Asp Cys Met Leu Ala Asn Gly Lys Leu Asp Glu Asp Tyr Glu Glu Glu
                805                 810                 815

Asp Glu Glu Glu Ser Leu Met Trp Arg Ala Pro Lys Glu Glu Ala
                820                 825                 830

Asp Tyr Glu Asp Asp Phe Leu Glu Tyr Asp Gln Glu His Ile Arg Phe
                835                 840                 845

Ile Asp Asn Met Leu Met Gly Ser Gly Ala Phe Val Lys Lys Ile Ser
            850                 855                 860

Leu Ser Pro Phe Ser Thr Thr Asp Ser Ala Tyr Glu Trp Lys Met Pro
865                 870                 875                 880

Lys Lys Ser Ser Leu Gly Ser Met Pro Phe Ser Ser Asp Phe Glu Asp
                885                 890                 895

Phe Asp Tyr Ser Ser Trp Asp Ala Met Cys Tyr Leu Asp Pro Ser Lys
                900                 905                 910

Ala Val Glu Glu Asp Asp Phe Val Val Gly Phe Trp Asn Pro Ser Glu
                915                 920                 925

Glu Asn Cys Gly Val Asp Thr Gly Lys Gln Ser Ile Ser Tyr Asp Leu
            930                 935                 940

His Thr Glu Gln Cys Ile Ala Asp Lys Ser Ile Ala Asp Cys Val Glu
945                 950                 955                 960

Ala Leu Leu Gly Cys Tyr Leu Thr Ser Cys Gly Glu Arg Ala Ala Gln
                965                 970                 975

Leu Phe Leu Cys Ser Leu Gly Leu Lys Val Leu Pro Val Ile Lys Arg
            980                 985                 990

Thr Asp Arg Glu Lys Ala Leu Cys  Pro Thr Arg Glu Asn  Phe Asn Ser
            995                 1000                1005

Gln Gln  Lys Asn Leu Ser Val  Ser Cys Ala Ala Ala  Ser Val Ala
    1010                 1015                 1020

Ser Ser  Arg Ser Ser Val Leu  Lys Asp Ser Glu Tyr  Gly Cys Leu
    1025                 1030                 1035

Lys Ile  Pro Pro Arg Cys Met  Phe Asp His Pro Asp  Ala Asp Lys
    1040                 1045                 1050

Thr Leu  Asn His Leu Ile Ser  Gly Phe Glu Asn Phe  Glu Lys Lys
    1055                 1060                 1065

Ile Asn  Tyr Arg Phe Lys Asn  Lys Ala Tyr Leu Leu  Gln Ala Phe
    1070                 1075                 1080

Thr His  Ala Ser Tyr His Tyr  Asn Thr Ile Thr Asp  Cys Tyr Gln
    1085                 1090                 1095

Arg Leu  Glu Phe Leu Gly Asp  Ala Ile Leu Asp Tyr  Leu Ile Thr
    1100                 1105                 1110

Lys His  Leu Tyr Glu Asp Pro  Arg Gln His Ser Pro  Gly Val Leu
    1115                 1120                 1125

Thr Asp  Leu Arg Ser Ala Leu  Val Asn Asn Thr Ile  Phe Ala Ser
    1130                 1135                 1140
```

```
Leu Ala Val Lys Tyr Asp Tyr His Lys Tyr Phe Lys Ala Val Ser
    1145                1150                1155

Pro Glu Leu Phe His Val Ile Asp Asp Phe Val Gln Phe Gln Leu
    1160                1165                1170

Glu Lys Asn Glu Met Gln Gly Met Asp Ser Leu Arg Arg Ser
    1175                1180                1185

Glu Glu Asp Glu Glu Lys Glu Glu Asp Ile Glu Val Pro Lys Ala
    1190                1195                1200

Met Gly Asp Ile Phe Glu Ser Leu Ala Gly Ala Ile Tyr Met Asp
    1205                1210                1215

Ser Gly Met Ser Leu Glu Thr Val Trp Gln Val Tyr Tyr Pro Met
    1220                1225                1230

Met Arg Pro Leu Ile Glu Lys Phe Ser Ala Asn Val Pro Arg Ser
    1235                1240                1245

Pro Val Arg Glu Leu Leu Glu Met Glu Pro Glu Thr Ala Lys Phe
    1250                1255                1260

Ser Pro Ala Glu Arg Thr Tyr Asp Gly Lys Val Arg Val Thr Val
    1265                1270                1275

Glu Val Val Gly Lys Gly Lys Phe Lys Gly Val Gly Arg Ser Tyr
    1280                1285                1290

Arg Ile Ala Lys Ser Ala Ala Ala Arg Arg Ala Leu Arg Ser Leu
    1295                1300                1305

Lys Ala Asn Gln Pro Gln Val Pro Asn Ser
    1310                1315

<210> SEQ ID NO 4
<211> LENGTH: 1922
<212> TYPE: PRT
<213> ORGANISM: Artificial sequence
<220> FEATURE:
<223> OTHER INFORMATION: Synthetic sequence

<400> SEQUENCE: 4

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Ala Thr Phe Ile Ala Val Leu Leu Thr Lys Glu
65                  70                  75                  80

Leu Ser Tyr Gln Ile Arg Gly Asp Phe Ser Arg Asn Gly Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Arg Trp Asn Gln Glu Phe Thr Lys
    130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175
```

```
Cys His Leu Ala Ile Leu Asp His Pro Tyr Arg Glu Ile Met Lys Leu
                180                 185                 190

Cys Glu Asn Cys Pro Ser Cys Pro Arg Ile Leu Gly Leu Thr Ala Ser
            195                 200                 205

Ile Leu Asn Gly Lys Cys Asp Pro Glu Glu Leu Glu Glu Lys Ile Gln
        210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
            260                 265                 270

Glu Leu Glu Glu Ala Leu Asn Phe Ile Asn Asp Cys Asn Ile Ser Val
        275                 280                 285

His Ser Lys Glu Arg Asp Ser Thr Leu Ile Ser Lys Gln Ile Leu Ser
        290                 295                 300

Asp Cys Arg Ala Val Leu Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Phe Leu
            340                 345                 350

Arg Lys Ile His Ala Leu Cys Glu Glu His Phe Ser Pro Ala Ser Leu
        355                 360                 365

Asp Leu Lys Phe Val Thr Pro Lys Val Ile Lys Leu Leu Glu Ile Leu
        370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Glu Asp Glu Glu Ile Glu Glu Lys Glu Lys Pro Glu Thr
            420                 425                 430

Asn Phe Pro Ser Pro Phe Thr Asn Ile Leu Cys Gly Ile Ile Phe Val
        435                 440                 445

Glu Arg Arg Tyr Thr Ala Val Val Leu Asn Arg Leu Ile Lys Glu Ala
        450                 455                 460

Gly Lys Gln Asp Pro Glu Leu Ala Tyr Ile Ser Ser Asn Phe Ile Thr
465                 470                 475                 480

Gly His Gly Ile Gly Lys Asn Gln Pro Arg Asn Lys Gln Met Glu Ala
                485                 490                 495

Glu Phe Arg Lys Gln Glu Glu Val Leu Arg Lys Phe Arg Ala His Glu
            500                 505                 510

Thr Asn Leu Leu Ile Ala Thr Ser Ile Val Glu Glu Gly Val Asp Ile
        515                 520                 525

Pro Lys Cys Asn Leu Val Val Arg Phe Asp Leu Pro Thr Glu Tyr Arg
        530                 535                 540

Ser Tyr Val Gln Ser Lys Gly Arg Ala Arg Ala Pro Ile Ser Asn Tyr
545                 550                 555                 560

Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
            580                 585                 590

Ser Val Asp Thr Gly Glu Thr Asp Ile Asp Pro Val Met Asp Asp Asp
```

```
                595                 600                 605
Asp Val Phe Pro Pro Tyr Val Leu Arg Pro Asp Gly Gly Pro Arg
    610                 615                 620
Val Thr Ile Asn Thr Ala Ile Gly His Ile Asn Arg Tyr Cys Ala Arg
625                 630                 635                 640
Leu Pro Ser Asp Pro Phe Thr His Leu Ala Pro Lys Cys Arg Thr Arg
                645                 650                 655
Glu Leu Pro Asp Gly Thr Phe Tyr Ser Thr Leu Tyr Leu Pro Ile Asn
                660                 665                 670
Ser Pro Leu Arg Ala Ser Ile Val Gly Pro Pro Met Ser Cys Val Arg
            675                 680                 685
Leu Ala Glu Arg Val Val Ala Leu Ile Cys Cys Glu Lys Leu His Lys
            690                 695                 700
Ile Gly Glu Leu Asp Asp His Leu Met Pro Val Gly Lys Glu Thr Val
705                 710                 715                 720
Lys Tyr Glu Glu Glu Leu Asp Leu His Asp Glu Glu Thr Ser Val
                725                 730                 735
Pro Gly Arg Pro Gly Ser Thr Lys Arg Arg Gln Cys Tyr Pro Lys Ala
                740                 745                 750
Ile Pro Glu Cys Leu Arg Asp Ser Tyr Pro Arg Pro Asp Gln Pro Cys
            755                 760                 765
Tyr Leu Tyr Val Ile Gly Met Val Leu Thr Thr Pro Leu Pro Asp Glu
770                 775                 780
Leu Asn Phe Arg Arg Lys Leu Tyr Pro Pro Glu Asp Thr Thr Arg
785                 790                 795                 800
Cys Phe Gly Ile Leu Thr Ala Lys Pro Ile Pro Gln Ile Pro His Phe
                805                 810                 815
Pro Val Tyr Thr Arg Ser Gly Glu Val Thr Ile Ser Ile Glu Leu Lys
                820                 825                 830
Lys Ser Gly Phe Met Leu Ser Leu Gln Met Leu Glu Leu Ile Thr Arg
            835                 840                 845
Leu His Gln Tyr Ile Phe Ser His Ile Leu Arg Leu Glu Lys Pro Ala
            850                 855                 860
Leu Glu Phe Lys Pro Thr Asp Ala Asp Ser Ala Tyr Cys Val Leu Pro
865                 870                 875                 880
Leu Asn Val Val Asn Asp Ser Ser Thr Leu Asp Ile Asp Phe Lys Phe
                885                 890                 895
Met Glu Asp Ile Glu Lys Ser Glu Ala Arg Ile Gly Ile Pro Ser Thr
            900                 905                 910
Lys Tyr Thr Lys Glu Thr Pro Phe Val Phe Lys Leu Glu Asp Tyr Gln
        915                 920                 925
Asp Ala Val Ile Ile Pro Arg Tyr Arg Asn Phe Asp Gln Pro His Arg
    930                 935                 940
Phe Tyr Val Ala Asp Val Tyr Thr Asp Leu Thr Pro Leu Ser Lys Phe
945                 950                 955                 960
Pro Ser Pro Glu Tyr Glu Thr Phe Ala Glu Tyr Tyr Lys Thr Lys Tyr
                965                 970                 975
Asn Leu Asp Leu Thr Asn Leu Asn Gln Pro Leu Leu Asp Val Asp His
            980                 985                 990
Thr Ser Ser Arg Leu Asn Leu Leu  Thr Pro Arg His Leu  Asn Gln Lys
            995                 1000                1005
Gly Lys  Ala Leu Pro Leu Ser  Ser Ala Glu Lys Arg  Lys Ala Lys
    1010                1015                1020
```

```
Trp Glu Ser Leu Gln Asn Lys Gln Ile Leu Val Pro Glu Leu Cys
    1025                1030                1035

Ala Ile His Pro Ile Pro Ala Ser Leu Trp Arg Lys Ala Val Cys
    1040                1045                1050

Leu Pro Ser Ile Leu Tyr Arg Leu His Cys Leu Leu Thr Ala Glu
    1055                1060                1065

Glu Leu Arg Ala Gln Thr Ala Ser Asp Ala Gly Val Gly Val Arg
    1070                1075                1080

Ser Leu Pro Ala Asp Phe Arg Tyr Pro Asn Leu Asp Phe Gly Trp
    1085                1090                1095

Lys Lys Ser Ile Asp Ser Lys Ser Phe Ile Ser Ile Ser Asn Ser
    1100                1105                1110

Ser Ser Ala Glu Asn Asp Asn Tyr Cys Lys His Ser Thr Ile Val
    1115                1120                1125

Pro Glu Asn Ala Ala His Gln Gly Ala Asn Arg Thr Ser Ser Leu
    1130                1135                1140

Glu Asn His Asp Gln Met Ser Val Asn Cys Arg Thr Leu Leu Ser
    1145                1150                1155

Glu Ser Pro Gly Lys Leu His Val Glu Val Ser Ala Asp Leu Thr
    1160                1165                1170

Ala Ile Asn Gly Leu Ser Tyr Asn Gln Asn Leu Ala Asn Gly Ser
    1175                1180                1185

Tyr Asp Leu Ala Asn Arg Asp Phe Cys Gln Gly Asn Gln Leu Asn
    1190                1195                1200

Tyr Tyr Lys Gln Glu Ile Pro Val Gln Pro Thr Thr Ser Tyr Ser
    1205                1210                1215

Ile Gln Asn Leu Tyr Ser Tyr Glu Asn Gln Pro Gln Pro Ser Asp
    1220                1225                1230

Glu Cys Thr Leu Leu Ser Asn Lys Tyr Leu Asp Gly Asn Ala Asn
    1235                1240                1245

Lys Ser Thr Ser Asp Gly Ser Pro Val Met Ala Val Met Pro Gly
    1250                1255                1260

Thr Thr Asp Thr Ile Gln Val Leu Lys Gly Arg Met Asp Ser Glu
    1265                1270                1275

Gln Ser Pro Ser Ile Gly Tyr Ser Ser Arg Thr Leu Gly Pro Asn
    1280                1285                1290

Pro Gly Leu Ile Leu Gln Ala Leu Thr Leu Ser Asn Ala Ser Asp
    1295                1300                1305

Gly Phe Asn Leu Glu Arg Leu Glu Met Leu Gly Asp Ser Phe Leu
    1310                1315                1320

Lys His Ala Ile Thr Thr Tyr Leu Phe Cys Thr Tyr Pro Asp Ala
    1325                1330                1335

His Glu Gly Arg Leu Ser Tyr Met Arg Ser Lys Lys Val Ser Asn
    1340                1345                1350

Cys Asn Leu Tyr Arg Leu Gly Lys Lys Lys Gly Leu Pro Ser Arg
    1355                1360                1365

Met Val Val Ser Ile Phe Asp Pro Pro Val Asn Trp Leu Pro Pro
    1370                1375                1380

Gly Tyr Val Val Asn Gln Asp Lys Ser Asn Thr Asp Lys Trp Glu
    1385                1390                1395

Lys Asp Glu Met Thr Lys Asp Cys Met Leu Ala Asn Gly Lys Leu
    1400                1405                1410
```

Asp Glu Asp Tyr Glu Glu Glu Asp Glu Glu Glu Ser Leu Met
    1415                1420                1425

Trp Arg Ala Pro Lys Glu Glu Ala Asp Tyr Glu Asp Asp Phe Leu
    1430                1435                1440

Glu Tyr Asp Gln Glu His Ile Arg Phe Ile Asp Asn Met Leu Met
    1445                1450                1455

Gly Ser Gly Ala Phe Val Lys Lys Ile Ser Leu Ser Pro Phe Ser
    1460                1465                1470

Thr Thr Asp Ser Ala Tyr Glu Trp Lys Met Pro Lys Lys Ser Ser
    1475                1480                1485

Leu Gly Ser Met Pro Phe Ser Ser Asp Phe Glu Asp Phe Asp Tyr
    1490                1495                1500

Ser Ser Trp Asp Ala Met Cys Tyr Leu Asp Pro Ser Lys Ala Val
    1505                1510                1515

Glu Glu Asp Asp Phe Val Val Gly Phe Trp Asn Pro Ser Glu Glu
    1520                1525                1530

Asn Cys Gly Val Asp Thr Gly Lys Gln Ser Ile Ser Tyr Asp Leu
    1535                1540                1545

His Thr Glu Gln Cys Ile Ala Asp Lys Ser Ile Ala Asp Cys Val
    1550                1555                1560

Glu Ala Leu Leu Gly Cys Tyr Leu Thr Ser Cys Gly Glu Arg Ala
    1565                1570                1575

Ala Gln Leu Phe Leu Cys Ser Leu Gly Leu Lys Val Leu Pro Val
    1580                1585                1590

Ile Lys Arg Thr Asp Arg Glu Lys Ala Leu Cys Pro Thr Arg Glu
    1595                1600                1605

Asn Phe Asn Ser Gln Gln Lys Asn Leu Ser Val Ser Cys Ala Ala
    1610                1615                1620

Ala Ser Val Ala Ser Ser Arg Ser Ser Val Leu Lys Asp Ser Glu
    1625                1630                1635

Tyr Gly Cys Leu Lys Ile Pro Pro Arg Cys Met Phe Asp His Pro
    1640                1645                1650

Asp Ala Asp Lys Thr Leu Asn His Leu Ile Ser Gly Phe Glu Asn
    1655                1660                1665

Phe Glu Lys Lys Ile Asn Tyr Arg Phe Lys Asn Lys Ala Tyr Leu
    1670                1675                1680

Leu Gln Ala Phe Thr His Ala Ser Tyr His Tyr Asn Thr Ile Thr
    1685                1690                1695

Asp Cys Tyr Gln Arg Leu Glu Phe Leu Gly Asp Ala Ile Leu Asp
    1700                1705                1710

Tyr Leu Ile Thr Lys His Leu Tyr Glu Asp Pro Arg Gln His Ser
    1715                1720                1725

Pro Gly Val Leu Thr Asp Leu Arg Ser Ala Leu Val Asn Asn Thr
    1730                1735                1740

Ile Phe Ala Ser Leu Ala Val Lys Tyr Asp Tyr His Lys Tyr Phe
    1745                1750                1755

Lys Ala Val Ser Pro Glu Leu Phe His Val Ile Asp Asp Phe Val
    1760                1765                1770

Gln Phe Gln Leu Glu Lys Asn Glu Met Gln Gly Met Asp Ser Glu
    1775                1780                1785

Leu Arg Arg Ser Glu Glu Asp Glu Glu Lys Glu Glu Asp Ile Glu
    1790                1795                1800

Val Pro Lys Ala Met Gly Asp Ile Phe Glu Ser Leu Ala Gly Ala

```
                1805                1810                1815
Ile Tyr Met Asp Ser Gly Met Ser Leu Glu Thr Val Trp Gln Val
        1820                1825                1830

Tyr Tyr Pro Met Met Arg Pro Leu Ile Glu Lys Phe Ser Ala Asn
        1835                1840                1845

Val Pro Arg Ser Pro Val Arg Glu Leu Leu Glu Met Glu Pro Glu
        1850                1855                1860

Thr Ala Lys Phe Ser Pro Ala Glu Arg Thr Tyr Asp Gly Lys Val
        1865                1870                1875

Arg Val Thr Val Glu Val Val Gly Lys Gly Lys Phe Lys Gly Val
        1880                1885                1890

Gly Arg Ser Tyr Arg Ile Ala Lys Ser Ala Ala Ala Arg Arg Ala
        1895                1900                1905

Leu Arg Ser Leu Lys Ala Asn Gln Pro Gln Val Pro Asn Ser
        1910                1915                1920

<210> SEQ ID NO 5
<211> LENGTH: 1930
<212> TYPE: PRT
<213> ORGANISM: Pan troglodytes

<400> SEQUENCE: 5

Met Lys Asn Pro Ala Leu Gln Pro Leu Ser Met Ala Gly Leu Gln Leu
1                5                  10                  15

Met Thr Pro Ala Ser Ser Pro Met Gly Pro Phe Phe Gly Leu Pro Trp
                20                  25                  30

Gln Gln Glu Ala Ile His Asp Asn Ile Tyr Thr Pro Arg Lys Tyr Gln
            35                  40                  45

Val Glu Leu Leu Glu Ala Ala Leu Asp His Asn Thr Ile Val Cys Leu
        50                  55                  60

Asn Thr Gly Ser Gly Lys Thr Phe Ile Ala Val Leu Leu Thr Lys Glu
65                  70                  75                  80

Leu Ser Tyr Gln Ile Arg Gly Asp Phe Ser Arg Asn Gly Lys Arg Thr
                85                  90                  95

Val Phe Leu Val Asn Ser Ala Asn Gln Val Ala Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Arg Trp Asn Gln Glu Phe Thr Lys
130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Glu Asn Cys Pro Ser Cys Pro Arg Ile Leu Gly Leu Thr Ala Ser
        195                 200                 205

Ile Leu Asn Gly Lys Cys Asp Pro Glu Glu Leu Glu Glu Lys Ile Gln
    210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255
```

-continued

Cys Gly Pro Phe Thr Asp Arg Ser Gly Leu Tyr Glu Arg Leu Leu Met
            260                 265                 270

Glu Leu Glu Glu Ala Leu Asn Phe Ile Asn Asp Cys Asn Ile Ser Val
        275                 280                 285

His Ser Lys Glu Arg Asp Ser Thr Leu Ile Ser Lys Gln Ile Leu Ser
    290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Phe Leu
            340                 345                 350

Arg Lys Ile His Ala Leu Cys Glu Glu His Phe Ser Pro Ala Ser Leu
        355                 360                 365

Asp Leu Lys Phe Val Thr Pro Lys Val Ile Lys Leu Leu Glu Ile Leu
    370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Glu Asp Glu Glu Ile Glu Glu Lys Glu Lys Pro Glu Thr
            420                 425                 430

Asn Phe Pro Ser Pro Phe Thr Asn Ile Leu Cys Gly Ile Ile Phe Val
        435                 440                 445

Glu Arg Arg Tyr Thr Ala Val Val Leu Asn Arg Leu Ile Lys Glu Ala
    450                 455                 460

Gly Lys Gln Asp Pro Glu Leu Ala Tyr Ile Ser Ser Asn Phe Ile Thr
465                 470                 475                 480

Gly His Gly Ile Gly Lys Asn Gln Pro Arg Asn Lys Gln Met Glu Ala
                485                 490                 495

Glu Phe Arg Lys Gln Glu Glu Val Leu Arg Lys Phe Arg Ala His Glu
            500                 505                 510

Thr Asn Leu Leu Ile Ala Thr Ser Ile Val Glu Glu Gly Val Asp Ile
        515                 520                 525

Pro Lys Cys Asn Leu Val Val Arg Phe Asp Leu Pro Thr Glu Tyr Arg
    530                 535                 540

Ser Tyr Val Gln Ser Lys Gly Arg Ala Arg Ala Pro Ile Ser Asn Tyr
545                 550                 555                 560

Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
            580                 585                 590

Ser Val Asp Thr Gly Glu Ile Asp Ile Asp Pro Val Met Asp Asp Asp
        595                 600                 605

Asp Val Phe Pro Pro Tyr Val Leu Arg Pro Asp Gly Gly Pro Arg
    610                 615                 620

Val Thr Ile Asn Thr Ala Ile Gly His Ile Asn Arg Tyr Cys Ala Arg
625                 630                 635                 640

Leu Pro Ser Asp Pro Phe Thr His Leu Ala Pro Lys Cys Arg Thr Arg
                645                 650                 655

Glu Leu Pro Asp Gly Thr Phe Tyr Ser Thr Leu Tyr Leu Pro Ile Asn
            660                 665                 670

Ser Pro Leu Arg Ala Ser Ile Val Gly Pro Pro Met Ser Cys Val Arg

```
              675                 680                 685
Leu Ala Glu Arg Val Val Ala Leu Ile Cys Cys Glu Lys Leu His Lys
690                 695                 700
Ile Gly Glu Leu Asp Asp His Leu Met Pro Val Gly Lys Glu Thr Val
705                 710                 715                 720
Lys Tyr Glu Glu Leu Asp Leu His Asp Glu Glu Thr Ser Val
                    725                 730             735
Pro Gly Arg Pro Gly Ser Thr Lys Arg Arg Gln Cys Tyr Pro Lys Ala
                740                 745                 750
Ile Pro Glu Cys Leu Arg Asp Ser Tyr Pro Arg Pro Asp Gln Pro Cys
            755                 760                 765
Tyr Leu Tyr Val Ile Gly Met Val Leu Thr Thr Pro Leu Pro Asp Glu
        770                 775                 780
Leu Asn Phe Arg Arg Lys Leu Tyr Pro Pro Glu Asp Thr Thr Arg
785                 790                 795                 800
Cys Phe Gly Ile Leu Thr Ala Lys Pro Ile Pro Gln Ile Pro His Phe
                805                 810                 815
Pro Val Tyr Thr Arg Ser Gly Glu Val Thr Ile Ser Ile Glu Leu Lys
                820                 825                 830
Lys Ser Gly Phe Met Leu Ser Leu Gln Met Leu Glu Leu Ile Thr Arg
                835                 840                 845
Leu His Gln Tyr Ile Phe Ser His Ile Leu Arg Leu Glu Lys Pro Ala
850                 855                 860
Leu Glu Phe Lys Pro Thr Asp Ala Asp Ser Ala Tyr Cys Val Leu Pro
865                 870                 875                 880
Leu Asn Val Val Asn Asp Ser Ser Thr Leu Asp Ile Asp Phe Lys Phe
                885                 890                 895
Met Glu Asp Ile Glu Lys Ser Glu Ala Arg Ile Gly Ile Pro Ser Thr
                900                 905                 910
Lys Tyr Thr Lys Glu Thr Pro Phe Val Phe Lys Leu Glu Asp Tyr Gln
            915                 920                 925
Asp Ala Val Ile Ile Pro Arg Tyr Arg Asn Phe Asp Gln Pro His Arg
930                 935                 940
Phe Tyr Val Ala Asp Val Tyr Thr Asp Leu Thr Pro Leu Ser Lys Phe
945                 950                 955                 960
Pro Ser Pro Glu Tyr Glu Thr Phe Ala Glu Tyr Tyr Lys Thr Lys Tyr
                965                 970                 975
Asn Leu Asp Leu Thr Asn Leu Asn Gln Pro Leu Leu Asp Val Asp His
            980                 985                 990
Thr Ser Ser Arg Leu Asn Leu Leu Thr Pro Arg His Leu Asn Gln Lys
        995                 1000                1005
Gly Lys Ala Leu Pro Leu Ser Ser Ala Glu Lys Arg Lys Ala Lys
        1010                1015                1020
Trp Glu Ser Leu Gln Asn Lys Gln Ile Leu Val Pro Glu Leu Cys
        1025                1030                1035
Ala Ile His Pro Ile Pro Ala Ser Leu Trp Arg Lys Ala Val Cys
        1040                1045                1050
Leu Pro Ser Ile Leu Tyr Arg Leu His Cys Leu Leu Thr Ala Glu
        1055                1060                1065
Glu Leu Arg Ala Gln Thr Ala Ser Asp Ala Gly Val Gly Val Arg
        1070                1075                1080
Ser Leu Pro Ala Asp Phe Arg Tyr Pro Asn Leu Asp Phe Gly Trp
        1085                1090                1095
```

```
Lys Lys Ser Ile Asp Ser Lys Ser Phe Ile Ser Ile Ser Asn Ser
1100                1105                1110

Ser Ser Ala Glu Asn Asp Asn Tyr Cys Lys His Ser Thr Ile Val
    1115                1120                1125

Pro Glu Asn Ala Ala His Gln Gly Ala Asn Arg Thr Ser Ser Leu
1130                1135                1140

Glu Asn His Asp Gln Met Ser Val Asn Cys Arg Thr Leu Leu Ser
    1145                1150                1155

Glu Ser Pro Gly Lys Leu His Val Glu Val Ser Ala Asp Leu Thr
1160                1165                1170

Ala Ile Asn Gly Leu Ser Tyr Asn Gln Asn Leu Ala Asn Gly Ser
    1175                1180                1185

Tyr Asp Leu Ala Asn Arg Asp Phe Cys Gln Gly Asn Gln Leu Asn
1190                1195                1200

Tyr Tyr Lys Gln Glu Ile Pro Val Gln Pro Thr Thr Ser Tyr Ser
    1205                1210                1215

Ile Gln Asn Leu Tyr Ser Tyr Glu Asn Gln Pro Gln Pro Ser Asp
1220                1225                1230

Glu Cys Thr Leu Leu Ser Asn Lys Tyr Leu Asp Gly Asn Ala Asn
    1235                1240                1245

Lys Ser Thr Ser Asp Gly Ser Pro Val Met Ala Val Met Pro Gly
1250                1255                1260

Thr Thr Asp Thr Ile Gln Val Leu Lys Gly Arg Met Asp Ser Glu
    1265                1270                1275

Gln Ser Pro Ser Ile Gly Tyr Ser Ser Arg Thr Leu Gly Pro Asn
1280                1285                1290

Pro Gly Leu Ile Leu Gln Ala Leu Thr Leu Ser Asn Ala Ser Asp
    1295                1300                1305

Gly Phe Asn Leu Glu Arg Leu Glu Met Leu Gly Asp Ser Phe Leu
1310                1315                1320

Lys His Ala Ile Thr Thr Tyr Leu Phe Cys Thr Tyr Pro Asp Ala
    1325                1330                1335

His Glu Gly Arg Leu Ser Tyr Met Arg Ser Lys Lys Val Ser Asn
1340                1345                1350

Cys Asn Leu Tyr Arg Leu Gly Lys Lys Lys Gly Leu Pro Ser Arg
    1355                1360                1365

Met Val Val Ser Ile Phe Asp Pro Pro Val Asn Trp Leu Pro Pro
1370                1375                1380

Gly Tyr Val Val Asn Gln Asp Lys Ser Asn Thr Asp Lys Trp Glu
    1385                1390                1395

Lys Asp Glu Met Thr Lys Asp Cys Met Leu Ala Asn Gly Lys Leu
1400                1405                1410

Asp Glu Asp Tyr Glu Glu Glu Asp Glu Glu Glu Ser Leu Met
    1415                1420                1425

Trp Arg Ala Pro Lys Glu Glu Ala Asp Tyr Glu Asp Asp Phe Leu
1430                1435                1440

Glu Tyr Asp Gln Glu His Ile Arg Phe Ile Asp Asn Met Leu Met
    1445                1450                1455

Gly Ser Gly Ala Phe Val Lys Lys Ile Ser Leu Ser Pro Phe Ser
1460                1465                1470

Thr Thr Asp Ser Ala Tyr Glu Trp Lys Met Pro Lys Lys Ser Ser
    1475                1480                1485
```

```
Leu Gly Ser Met Pro Phe Ser Ser Asp Phe Glu Asp Phe Asp Tyr
1490                1495                1500

Ser Ser Trp Asp Ala Met Cys Tyr Leu Asp Pro Ser Lys Ala Val
1505                1510                1515

Glu Glu Asp Asp Phe Val Val Gly Phe Trp Asn Pro Ser Glu Glu
1520                1525                1530

Asn Cys Gly Val Asp Thr Gly Lys Gln Ser Ile Ser Tyr Asp Leu
1535                1540                1545

His Thr Glu Gln Cys Ile Ala Asp Lys Ser Ile Ala Asp Cys Val
1550                1555                1560

Glu Ala Leu Leu Gly Cys Tyr Leu Thr Ser Cys Gly Glu Arg Ala
1565                1570                1575

Ala Gln Leu Phe Leu Cys Ser Leu Gly Leu Lys Val Leu Pro Val
1580                1585                1590

Ile Lys Arg Thr Asp Arg Glu Lys Ala Leu Cys Pro Thr Arg Glu
1595                1600                1605

Asn Phe Asn Ser Gln Gln Lys Asn Leu Ser Val Ser Cys Ala Ala
1610                1615                1620

Ala Ser Val Ala Ser Ser Arg Ser Ser Val Leu Lys Asp Ser Glu
1625                1630                1635

Tyr Gly Cys Leu Lys Ile Pro Pro Arg Cys Met Phe Asp His Pro
1640                1645                1650

Asp Ala Asp Lys Thr Leu Asn His Leu Ile Ser Gly Phe Glu Asn
1655                1660                1665

Phe Glu Lys Lys Ile Asn Tyr Arg Phe Lys Asn Lys Ala Tyr Leu
1670                1675                1680

Leu Gln Ala Phe Thr His Ala Ser Tyr His Tyr Asn Thr Ile Thr
1685                1690                1695

Asp Cys Tyr Gln Arg Leu Glu Phe Leu Gly Asp Ala Ile Leu Asp
1700                1705                1710

Tyr Leu Ile Thr Lys His Leu Tyr Glu Asp Pro Arg Gln His Ser
1715                1720                1725

Pro Gly Val Leu Thr Asp Leu Arg Ser Ala Leu Val Asn Asn Thr
1730                1735                1740

Ile Phe Ala Ser Leu Ala Val Lys Tyr Asp Tyr His Lys Tyr Phe
1745                1750                1755

Lys Ala Val Ser Pro Glu Leu Phe His Val Ile Asp Asp Phe Val
1760                1765                1770

Gln Phe Gln Leu Glu Lys Asn Glu Met Gln Gly Met Asp Ser Glu
1775                1780                1785

Leu Arg Arg Ser Glu Glu Asp Glu Glu Lys Glu Glu Asp Ile Glu
1790                1795                1800

Val Pro Lys Ala Met Gly Asp Ile Phe Glu Ser Leu Ala Gly Ala
1805                1810                1815

Ile Tyr Met Asp Ser Gly Met Ser Leu Glu Thr Val Trp Gln Val
1820                1825                1830

Tyr Tyr Pro Met Met Arg Pro Leu Ile Glu Lys Phe Ser Ala Asn
1835                1840                1845

Val Pro Arg Ser Pro Val Arg Glu Leu Leu Glu Met Glu Pro Glu
1850                1855                1860

Thr Ala Lys Phe Ser Pro Ala Glu Arg Thr Tyr Asp Gly Lys Val
1865                1870                1875

Arg Val Thr Val Glu Val Val Gly Lys Gly Lys Phe Lys Gly Val
```

```
                1880                1885                1890

Gly Arg Ser Tyr Arg Ile Ala Lys Ser Ala Ala Ala Arg Arg Ala
        1895                1900                1905

Leu Arg Ser Leu Lys Ala Asn Gln Pro Gln Leu Trp Val Ser Leu
        1910                1915                1920

Ala Leu Pro Ser Thr Tyr Gln
        1925                1930

<210> SEQ ID NO 6
<211> LENGTH: 1923
<212> TYPE: PRT
<213> ORGANISM: Canis familiaris

<400> SEQUENCE: 6

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ser Tyr Gln Ile Arg Gly Asp Phe Asn Arg Asn Gly Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Lys Trp Asn Gln Glu Phe Thr Lys
    130                 135                 140

His Gln Val Leu Val Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Glu Asn Cys Pro Ser Cys Pro Arg Ile Leu Gly Leu Thr Ala Ser
        195                 200                 205

Ile Leu Asn Gly Lys Cys Asp Pro Glu Glu Leu Glu Glu Lys Ile Gln
    210                 215                 220

Lys Leu Glu Lys Ile Leu Lys Ser Asn Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Gly Arg Leu Leu Val
            260                 265                 270

Glu Leu Glu Glu Ala Leu Asn Phe Ile Asn Asp Cys Asn Ile Ser Val
        275                 280                 285

His Ser Lys Glu Arg Asp Ser Thr Leu Ile Ser Lys Gln Ile Leu Ser
    290                 295                 300

Asp Cys Arg Ala Val Leu Val Val Leu Gly Pro Trp Cys Ala Asp Lys
305                 310                 315                 320
```

```
Val Ala Gly Met Met Val Arg Glu Leu Gln Lys Tyr Ile Lys His Glu
            325                 330                 335

Gln Glu Glu Leu His Arg Lys Phe Leu Leu Phe Thr Asp Thr Phe Leu
        340                 345                 350

Arg Lys Ile His Ala Leu Cys Glu Glu His Phe Ser Pro Ala Ser Leu
        355                 360                 365

Asp Leu Lys Phe Val Thr Pro Lys Val Ile Lys Leu Leu Glu Ile Leu
    370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Glu Asp Glu Glu Ile Glu Glu Lys Glu Lys Pro Glu Thr
                420                 425                 430

Asn Phe Pro Ser Pro Phe Thr Asn Ile Leu Cys Gly Ile Ile Phe Val
            435                 440                 445

Glu Arg Arg Tyr Thr Ala Val Val Leu Asn Arg Leu Ile Lys Glu Ala
    450                 455                 460

Gly Lys Gln Asp Pro Glu Leu Ala Tyr Ile Ser Ser Asn Phe Ile Thr
465                 470                 475                 480

Gly His Gly Ile Gly Lys Asn Gln Pro Arg Asn Lys Gln Met Glu Ala
                485                 490                 495

Glu Phe Arg Lys Gln Glu Val Leu Arg Lys Phe Arg Ala His Glu
                500                 505                 510

Thr Asn Leu Leu Ile Ala Thr Ser Ile Val Glu Glu Gly Val Asp Ile
            515                 520                 525

Pro Lys Cys Asn Leu Val Val Arg Phe Asp Leu Pro Thr Glu Tyr Arg
    530                 535                 540

Ser Tyr Val Gln Ser Lys Gly Arg Ala Arg Ala Pro Ile Ser Asn Tyr
545                 550                 555                 560

Ile Met Leu Ala Asp Thr Asp Lys Ile Lys Ser Phe Glu Glu Asp Leu
                565                 570                 575

Lys Thr Tyr Lys Ala Ile Glu Lys Ile Leu Arg Asn Lys Cys Ser Lys
                580                 585                 590

Ser Val Asp Thr Gly Glu Thr Asp Ile Glu Pro Val Val Asp Asp Asp
            595                 600                 605

Asp Val Phe Pro Pro Tyr Val Leu Arg Pro Asp Asp Gly Gly Pro Arg
    610                 615                 620

Val Thr Ile Asn Thr Ala Ile Gly His Ile Asn Arg Tyr Cys Ala Arg
625                 630                 635                 640

Leu Pro Ser Asp Pro Phe Thr His Leu Ala Pro Lys Cys Arg Thr Arg
                645                 650                 655

Glu Leu Pro Asp Gly Thr Phe Tyr Ser Thr Leu Tyr Leu Pro Ile Asn
                660                 665                 670

Ser Pro Leu Arg Ala Ser Ile Val Gly Pro Pro Met Ser Cys Val Arg
            675                 680                 685

Leu Ala Glu Arg Val Val Ala Leu Ile Cys Cys Glu Lys Leu His Lys
    690                 695                 700

Ile Gly Glu Leu Asp Asp His Leu Met Pro Val Gly Lys Glu Thr Val
705                 710                 715                 720

Lys Tyr Glu Glu Glu Leu Asp Leu His Asp Glu Glu Thr Ser Val
                725                 730                 735

Pro Gly Arg Pro Gly Ser Thr Lys Arg Arg Gln Cys Tyr Pro Lys Ala
```

-continued

```
              740                 745                 750
Ile Pro Glu Cys Leu Arg Asp Ser Tyr Pro Lys Pro Asp Gln Pro Cys
            755                 760                 765
Tyr Leu Tyr Val Ile Gly Met Val Leu Thr Thr Pro Leu Pro Asp Glu
        770                 775                 780
Leu Asn Phe Arg Arg Arg Lys Leu Tyr Pro Pro Glu Asp Thr Thr Arg
785                 790                 795                 800
Cys Phe Gly Ile Leu Thr Ala Lys Pro Ile Pro Gln Ile Pro His Phe
                805                 810                 815
Pro Val Tyr Thr Arg Ser Gly Glu Val Thr Ile Ser Ile Glu Leu Lys
            820                 825                 830
Lys Ser Gly Phe Thr Leu Ser Leu Gln Met Leu Glu Leu Ile Thr Arg
        835                 840                 845
Leu His Gln Tyr Ile Phe Ser His Ile Leu Arg Leu Glu Lys Pro Ala
    850                 855                 860
Leu Glu Phe Lys Pro Thr Asp Ala Asp Ser Ala Tyr Cys Val Leu Pro
865                 870                 875                 880
Leu Asn Val Val Asn Asp Ser Ser Thr Leu Asp Ile Asp Phe Lys Phe
                885                 890                 895
Met Glu Asp Ile Glu Lys Ser Glu Ala Arg Ile Gly Ile Pro Ser Thr
            900                 905                 910
Lys Tyr Ser Lys Glu Thr Pro Phe Val Phe Lys Leu Glu Asp Tyr Gln
        915                 920                 925
Asp Ala Val Ile Ile Pro Arg Tyr Arg Asn Phe Asp Gln Pro His Arg
    930                 935                 940
Phe Tyr Val Ala Asp Val Tyr Thr Asp Leu Thr Pro Leu Ser Lys Phe
945                 950                 955                 960
Pro Ser Pro Glu Tyr Glu Thr Phe Ala Glu Tyr Tyr Lys Thr Lys Tyr
                965                 970                 975
Asn Leu Asp Leu Thr Asn Leu Asn Gln Pro Leu Leu Asp Val Asp His
            980                 985                 990
Thr Ser Ser Arg Leu Asn Leu Leu Thr Pro Arg His Leu Asn Gln Lys
        995                 1000                1005
Gly Lys Ala Leu Pro Leu Ser Ser Ala Glu Lys Arg Lys Ala Lys
    1010                1015                1020
Trp Glu Ser Leu Gln Asn Lys Gln Ile Leu Val Pro Glu Leu Cys
    1025                1030                1035
Ala Ile His Pro Ile Pro Ala Ser Leu Trp Arg Lys Ala Val Cys
    1040                1045                1050
Leu Pro Ser Ile Leu Tyr Arg Leu His Cys Leu Leu Thr Ala Glu
    1055                1060                1065
Glu Leu Arg Ala Gln Thr Ala Ser Asp Ala Gly Val Gly Val Arg
    1070                1075                1080
Ser Leu Pro Val Asp Phe Arg Tyr Pro Asn Leu Asp Phe Gly Trp
    1085                1090                1095
Lys Lys Ser Ile Asp Ser Lys Ser Phe Ile Ser Val Ala Asn Ser
    1100                1105                1110
Ser Ser Ala Glu Asn Glu Asn Tyr Cys Lys His Ser Thr Ile Val
    1115                1120                1125
Val Pro Glu Asn Ala Ala Arg Gln Gly Ala Asn Arg Thr Ser Ser
    1130                1135                1140
Leu Glu Asn His Asp Gln Met Ser Val Asn Cys Arg Thr Leu Phe
    1145                1150                1155
```

```
Ser Glu Ser Pro Gly Lys Leu Gln Ile Glu Val Val Thr Asp Leu
    1160            1165                1170
Thr Ala Ile Asn Gly Leu Ser Tyr Asn Lys Asn Leu Ala Asn Gly
    1175            1180                1185
Ser Tyr Asp Leu Ala Asn Arg Asp Phe Cys Gln Gly Asn Gln Leu
    1190            1195                1200
Asn Tyr Tyr Lys Gln Glu Ile Pro Val Gln Pro Thr Thr Ser Tyr
    1205            1210                1215
Pro Ile Gln Asn Leu Tyr Asn Tyr Glu Asn Gln Pro Lys Pro Ser
    1220            1225                1230
Asp Glu Cys Thr Leu Leu Ser Asn Lys Tyr Leu Asp Gly Asn Ala
    1235            1240                1245
Asn Lys Ser Thr Ser Asp Gly Ser Pro Thr Thr Ala Ala Met Pro
    1250            1255                1260
Gly Thr Thr Glu Ala Val Arg Ala Leu Lys Asp Lys Met Gly Ser
    1265            1270                1275
Glu Gln Ser Pro Cys Pro Gly Tyr Ser Ser Arg Thr Leu Gly Pro
    1280            1285                1290
Asn Pro Gly Leu Ile Leu Gln Ala Leu Thr Leu Ser Asn Ala Ser
    1295            1300                1305
Asp Gly Phe Asn Leu Glu Arg Leu Glu Met Leu Gly Asp Ser Phe
    1310            1315                1320
Leu Lys His Ala Ile Thr Thr Tyr Leu Phe Cys Thr Tyr Pro Asp
    1325            1330                1335
Ala His Glu Gly Arg Leu Ser Tyr Met Arg Ser Lys Lys Val Ser
    1340            1345                1350
Asn Cys Asn Leu Tyr Arg Leu Gly Lys Lys Lys Gly Leu Pro Ser
    1355            1360                1365
Arg Met Val Val Ser Ile Phe Asp Pro Pro Val Asn Trp Leu Pro
    1370            1375                1380
Pro Gly Tyr Val Val Asn Gln Asp Lys Ser Asn Ala Asp Lys Trp
    1385            1390                1395
Glu Lys Asp Glu Met Thr Lys Asp Cys Met Leu Ala Asn Gly Lys
    1400            1405                1410
Leu Asp Glu Asp Phe Glu Glu Asp Asp Glu Glu Glu Asp Leu
    1415            1420                1425
Met Trp Arg Ala Pro Lys Glu Asp Ala Asp Tyr Glu Asp Asp Phe
    1430            1435                1440
Leu Glu Tyr Asp Gln Glu His Ile Lys Phe Ile Asp Asn Met Leu
    1445            1450                1455
Met Gly Ser Gly Ala Phe Val Lys Lys Ile Ser Leu Ser Pro Phe
    1460            1465                1470
Ser Thr Thr Asp Ser Ala Tyr Glu Trp Lys Met Pro Lys Lys Ser
    1475            1480                1485
Ser Leu Gly Ser Met Pro Phe Ser Ser Asp Phe Glu Asp Phe Asp
    1490            1495                1500
Tyr Ser Ser Trp Asp Ala Met Cys Tyr Leu Asp Pro Ser Lys Ala
    1505            1510                1515
Val Glu Glu Asp Asp Phe Val Val Gly Phe Trp Asn Pro Ser Glu
    1520            1525                1530
Glu Asn Cys Gly Val Asp Thr Gly Lys Gln Ser Ile Ser Tyr Asp
    1535            1540                1545
```

Leu His Thr Glu Gln Cys Ile Ala Asp Lys Ser Ile Ala Asp Cys
1550                1555                1560

Val Glu Ala Leu Leu Gly Cys Tyr Leu Thr Ser Cys Gly Glu Arg
1565                1570                1575

Ala Ala Gln Leu Phe Leu Cys Ser Leu Gly Leu Lys Val Leu Pro
1580                1585                1590

Val Met Lys Arg Thr Asp Arg Glu Lys Thr Met Cys Pro Pro Arg
1595                1600                1605

Glu Asn Phe Ser Ser Gln Gln Lys Asn Leu Ser Gly Gly Arg Ala
1610                1615                1620

Ala Ala Ser Val Ala Ser Leu Arg Pro Ser Val Leu Lys Asp Leu
1625                1630                1635

Glu Tyr Gly Cys Leu Lys Ile Pro Pro Arg Cys Met Phe Asp His
1640                1645                1650

Pro Asp Ala Asp Lys Thr Leu Asn His Leu Ile Ser Gly Phe Glu
1655                1660                1665

Asn Phe Glu Lys Lys Ile Asn Tyr Arg Phe Lys Asn Lys Ala Tyr
1670                1675                1680

Leu Leu Gln Ala Phe Thr His Ala Ser Tyr His Tyr Asn Thr Ile
1685                1690                1695

Thr Asp Cys Tyr Gln Arg Leu Glu Phe Leu Gly Asp Ala Ile Leu
1700                1705                1710

Asp Tyr Leu Ile Thr Lys His Leu Tyr Glu Asp Pro Arg Gln His
1715                1720                1725

Ser Pro Gly Val Leu Thr Asp Leu Arg Ser Ala Leu Val Asn Asn
1730                1735                1740

Thr Ile Phe Ala Ser Leu Ala Val Lys Tyr Asp Tyr His Lys Tyr
1745                1750                1755

Phe Lys Ala Val Ser Pro Glu Leu Phe His Val Ile Asp Asp Phe
1760                1765                1770

Val Gln Phe Gln Leu Glu Lys Asn Glu Met Gln Gly Met Asp Ser
1775                1780                1785

Glu Leu Arg Arg Ser Glu Glu Asp Glu Glu Lys Glu Glu Asp Ile
1790                1795                1800

Glu Val Pro Lys Ala Met Gly Asp Ile Phe Glu Ser Leu Ala Gly
1805                1810                1815

Ala Ile Tyr Met Asp Ser Gly Met Ser Leu Glu Met Val Trp Gln
1820                1825                1830

Val Tyr Tyr Pro Met Met Arg Pro Leu Ile Glu Lys Phe Ser Ala
1835                1840                1845

Asn Val Pro Arg Ser Pro Val Arg Glu Leu Leu Glu Met Glu Pro
1850                1855                1860

Glu Thr Ala Lys Phe Ser Pro Ala Glu Arg Thr Tyr Asp Gly Lys
1865                1870                1875

Val Arg Val Thr Val Glu Val Val Gly Lys Gly Lys Phe Lys Gly
1880                1885                1890

Val Gly Arg Ser Tyr Arg Ile Ala Lys Ser Ala Ala Ala Arg Arg
1895                1900                1905

Ala Leu Arg Ser Leu Lys Ala Asn Gln Pro Gln Val Pro Asn Ser
1910                1915                1920

<210> SEQ ID NO 7
<211> LENGTH: 1918
<212> TYPE: PRT

<213> ORGANISM: Rattus norvegicus

<400> SEQUENCE: 7

```
Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Val Leu Leu Thr Lys Glu
65                  70                  75                  80

Leu Ala His Gln Ile Arg Gly Asp Leu Ser Pro His Ala Lys Arg Thr
                85                  90                  95

Val Phe Leu Val Asn Ser Ala Asn Gln Val Ala Gln Gln Val Ser Ala
            100                 105                 110

Val Arg Thr His Ser Asp Leu Lys Val Gly Glu Tyr Ser Asn Leu Glu
        115                 120                 125

Val Asn Ala Ser Trp Thr Lys Glu Arg Trp Ser Gln Glu Phe Thr Lys
    130                 135                 140

His Gln Val Leu Ile Met Thr Cys Tyr Val Ala Leu Asn Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
            180                 185                 190

Cys Asp Ser Cys Pro Ser Cys Pro Arg Ile Leu Gly Leu Thr Ala Ser
        195                 200                 205

Ile Leu Asn Gly Lys Cys Asp Pro Asp Glu Leu Glu Glu Lys Ile Gln
    210                 215                 220

Lys Leu Glu Lys Ile Leu Lys Ser Gly Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
            260                 265                 270

Glu Leu Glu Glu Ala Leu Asp Phe Ile Asn Asp Cys Asn Val Ser Val
        275                 280                 285

His Ser Lys Glu Arg Asp Ser Thr Leu Ile Ser Lys Gln Ile Leu Ser
    290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Leu Leu
            340                 345                 350

Arg Lys Ile His Ala Leu Cys Glu Glu Tyr Phe Ser Pro Ala Ser Leu
        355                 360                 365

Asp Leu Lys Tyr Val Thr Pro Lys Val Met Lys Leu Leu Glu Ile Leu
    370                 375                 380

Arg Lys Tyr Lys Pro Tyr Glu Arg Gln Gln Phe Glu Ser Val Glu Trp
385                 390                 395                 400
```

-continued

```
Tyr Asn Asn Arg Asn Gln Asp Asn Tyr Val Ser Trp Ser Asp Ser Glu
                405                 410                 415
Asp Asp Asp Asp Glu Glu Ile Glu Glu Lys Glu Lys Pro Glu Thr
        420                 425                 430
Asn Phe Pro Ser Pro Phe Thr Asn Ile Leu Cys Gly Ile Ile Phe Val
        435                 440                 445
Glu Arg Arg Tyr Thr Ala Val Val Leu Asn Arg Leu Ile Lys Glu Ala
        450                 455                 460
Gly Lys Gln Asp Pro Glu Leu Ala Tyr Ile Ser Asn Phe Ile Thr
465                 470                 475                 480
Gly His Gly Ile Gly Lys Asn Gln Pro Arg Ser Lys Gln Met Glu Ala
                485                 490                 495
Glu Phe Arg Lys Gln Glu Val Leu Arg Lys Phe Arg Ala His Glu
        500                 505                 510
Thr Asn Leu Leu Ile Ala Thr Ser Val Val Glu Glu Gly Val Asp Ile
        515                 520                 525
Pro Lys Cys Asn Leu Val Val Arg Phe Asp Leu Pro Thr Glu Tyr Arg
        530                 535                 540
Ser Tyr Val Gln Ser Lys Gly Arg Ala Arg Ala Pro Ile Ser Asn Tyr
545                 550                 555                 560
Val Met Leu Ala Asp Thr Asp Lys Ile Lys Ser Phe Glu Glu Asp Leu
                565                 570                 575
Lys Thr Tyr Lys Ala Ile Glu Lys Ile Leu Arg Asn Lys Cys Ser Lys
                580                 585                 590
Ser Val Asp Gly Ala Glu Ala Asp Val His Ala Val Asp Asp Asp
        595                 600                 605
Asp Val Phe Pro Pro Tyr Val Leu Arg Pro Asp Asp Gly Gly Pro Arg
        610                 615                 620
Val Thr Ile Asn Thr Ala Ile Gly His Ile Asn Arg Tyr Cys Ala Arg
625                 630                 635                 640
Leu Pro Ser Asp Pro Phe Thr His Leu Ala Pro Lys Cys Arg Thr Arg
                645                 650                 655
Glu Leu Pro Asp Gly Thr Phe Tyr Ser Thr Leu Tyr Leu Pro Ile Asn
        660                 665                 670
Ser Pro Leu Arg Ala Ser Ile Val Gly Pro Pro Met Gly Cys Val Arg
        675                 680                 685
Leu Ala Glu Arg Val Val Ala Leu Ile Cys Cys Glu Lys Leu His Lys
        690                 695                 700
Ile Gly Glu Leu Asp Glu His Leu Met Pro Val Gly Lys Glu Thr Val
705                 710                 715                 720
Lys Tyr Glu Glu Glu Leu Asp Leu His Asp Glu Glu Thr Ser Val
                725                 730                 735
Pro Gly Arg Pro Gly Ser Thr Lys Arg Arg Gln Cys Tyr Pro Lys Ala
        740                 745                 750
Ile Pro Glu Cys Leu Arg Glu Ser Tyr Pro Lys Pro Asp Gln Pro Cys
        755                 760                 765
Tyr Leu Tyr Val Ile Gly Met Val Leu Thr Thr Pro Leu Pro Asp Glu
        770                 775                 780
Leu Asn Phe Arg Arg Arg Lys Leu Tyr Pro Pro Glu Asp Thr Thr Arg
785                 790                 795                 800
Cys Phe Gly Ile Leu Thr Ala Lys Pro Ile Pro Gln Ile Pro His Phe
                805                 810                 815
Pro Val Tyr Thr Arg Ser Gly Glu Val Thr Ile Ser Ile Glu Leu Lys
```

-continued

```
                820               825               830
Lys Ser Gly Phe Thr Leu Ser Gln Gln Met Leu Glu Leu Val Thr Arg
            835               840               845
Leu His Gln Tyr Ile Phe Ser His Ile Leu Arg Leu Glu Lys Pro Ala
        850               855               860
Leu Glu Phe Gln Pro Ala Gly Ala Glu Ser Ala Tyr Cys Val Leu Pro
865               870               875               880
Leu Asn Val Val Asn Asp Ser Ser Thr Leu Asp Ile Asp Phe Lys Phe
                885               890               895
Met Glu Asp Ile Glu Lys Ser Glu Ala Arg Ile Gly Ile Pro Ser Thr
            900               905               910
Lys Tyr Ser Lys Glu Thr Pro Phe Val Phe Lys Leu Glu Asp Tyr Gln
        915               920               925
Asp Ala Val Ile Ile Pro Arg Tyr Arg Asn Phe Asp Gln Pro His Arg
    930               935               940
Phe Tyr Val Ala Asp Val Tyr Thr Asp Leu Thr Pro Leu Ser Lys Phe
945               950               955               960
Pro Ser Pro Glu Tyr Glu Thr Phe Ala Glu Tyr Tyr Lys Thr Lys Tyr
                965               970               975
Asn Leu Asp Leu Thr Asn Leu Asn Gln Pro Leu Leu Asp Val Asp His
            980               985               990
Thr Ser Ser Arg Leu Asn Leu Leu Thr Pro Arg His Leu Asn Gln Lys
        995              1000              1005
Gly Lys Ala Leu Pro Leu Ser Ser Ala Glu Lys Arg Lys Ala Lys
    1010              1015              1020
Trp Glu Ser Leu Gln Asn Lys Gln Ile Leu Val Pro Glu Leu Cys
    1025              1030              1035
Ala Ile His Pro Ile Pro Ala Ser Leu Trp Arg Lys Ala Val Cys
    1040              1045              1050
Leu Pro Ser Ile Leu Tyr Arg Leu His Cys Leu Leu Thr Ala Glu
    1055              1060              1065
Glu Leu Arg Ala Gln Thr Ala Ser Asp Ala Gly Val Gly Val Arg
    1070              1075              1080
Ser Leu Pro Ala Asp Phe Arg Tyr Pro Asn Leu Asp Phe Gly Trp
    1085              1090              1095
Lys Lys Ser Ile Asp Ser Lys Ser Phe Ile Ser Thr Cys Asn Ser
    1100              1105              1110
Ser Leu Ala Glu Ser Asp Asn Tyr Cys Lys His Ser Thr Thr Val
    1115              1120              1125
Val Pro Glu Asn Ala Ala His Gln Gly Ala Thr Arg Pro Ser Leu
    1130              1135              1140
Glu Asn His Asp Gln Met Ser Val Asn Cys Lys Arg Leu Pro Ala
    1145              1150              1155
Glu Ser Pro Ala Lys Leu Gln Ser Glu Val Ser Val Asp Leu Thr
    1160              1165              1170
Ala Ile Asn Gly Leu Ser Tyr Asn Lys Ser Leu Ala Asn Gly Ser
    1175              1180              1185
Tyr Asp Leu Val Asn Arg Asp Phe Cys Gln Gly Asn Gln Leu Thr
    1190              1195              1200
Tyr Phe Lys Gln Glu Ile Pro Val Gln Pro Thr Thr Ser Tyr Pro
    1205              1210              1215
Ile Gln Asn Leu Tyr Asn Tyr Glu Asn Gln Pro Thr Pro Ser Asn
    1220              1225              1230
```

-continued

```
Glu Cys Pro Leu Leu Ser Asn Lys Tyr Leu Asp Gly Asn Ala Asn
    1235                1240                1245

Thr Ser Thr Ser Asp Gly Ser Pro Ala Gly Ser Pro Arg Pro Ala
    1250                1255                1260

Met Met Thr Ala Val Glu Ala Leu Glu Gly Arg Thr Asp Ser Glu
    1265                1270                1275

Gln Ser Pro Ser Val Gly His Ser Ser Arg Thr Leu Gly Pro Asn
    1280                1285                1290

Pro Gly Leu Ile Leu Gln Ala Leu Thr Leu Ser Asn Ala Ser Asp
    1295                1300                1305

Gly Phe Asn Leu Glu Arg Leu Glu Met Leu Gly Asp Ser Phe Leu
    1310                1315                1320

Lys His Ala Ile Thr Thr Tyr Leu Phe Cys Thr Tyr Pro Asp Ala
    1325                1330                1335

His Glu Gly Arg Leu Ser Tyr Met Arg Ser Lys Lys Val Ser Asn
    1340                1345                1350

Cys Asn Leu Tyr Arg Leu Gly Lys Lys Gln Gly Leu Pro Ser Arg
    1355                1360                1365

Met Val Val Ser Ile Phe Asp Pro Pro Val Asn Trp Leu Pro Pro
    1370                1375                1380

Gly Tyr Val Val Asn Gln Asp Lys Ser Asn Ser Glu Lys Trp Glu
    1385                1390                1395

Lys Asp Glu Met Thr Lys Asp Cys Leu Leu Ala Asn Gly Lys Leu
    1400                1405                1410

Gly Glu Asp Cys Glu Glu Glu Glu Glu Glu Leu Ala Trp Arg
    1415                1420                1425

Ala Pro Lys Glu Glu Ala Glu Tyr Glu Asp Asp Leu Leu Glu Tyr
    1430                1435                1440

Asp Gln Glu His Ile Gln Phe Ile Asp Ser Met Leu Met Gly Ser
    1445                1450                1455

Gly Ala Phe Val Lys Lys Ile Pro Leu Ser Pro Phe Ser Thr Ser
    1460                1465                1470

Asp Ser Ala Tyr Glu Trp Lys Met Pro Lys Lys Ala Ser Leu Gly
    1475                1480                1485

Ser Val Pro Phe Ser Ser Asp Leu Glu Asp Phe Asp Tyr Ser Ser
    1490                1495                1500

Trp Asp Ala Met Cys Tyr Leu Asp Pro Ser Lys Ala Val Glu Glu
    1505                1510                1515

Asp Asp Phe Val Val Gly Phe Trp Asn Pro Ser Glu Glu Asn Cys
    1520                1525                1530

Gly Val Asp Thr Gly Lys Gln Ser Ile Ser Tyr Asp Leu His Thr
    1535                1540                1545

Glu Gln Cys Ile Ala Asp Lys Ser Ile Ala Asp Cys Val Glu Ala
    1550                1555                1560

Leu Leu Gly Cys Tyr Leu Thr Ser Cys Gly Glu Arg Ala Ala Gln
    1565                1570                1575

Leu Phe Leu Cys Ser Leu Gly Leu Lys Val Leu Pro Val Ile Lys
    1580                1585                1590

Arg Thr Ser Arg Asp Lys Ala Ser Tyr Pro Ala Gln Glu Asn Ser
    1595                1600                1605

Ser Ser Gln Gln Lys Ser Pro Ser Gly Ser Cys Ala Ala Ala Val
    1610                1615                1620
```

| Ser | Pro | Arg | Ser | Ser | Ala | Gly | Lys | Asp | Leu | Glu | Tyr | Gly | Cys | Leu |
| | 1625 | | | | 1630 | | | | 1635 | | | | | |

Lys Ile Pro Pro Arg Cys Met Phe Asp His Pro Asp Ala Glu Lys
    1640                1645                1650

Thr Leu Asn His Leu Ile Ser Gly Phe Glu Asn Phe Glu Lys Lys
    1655                1660                1665

Ile Asn Tyr Ile Phe Lys Asn Lys Ala Tyr Leu Leu Gln Ala Phe
    1670                1675                1680

Thr His Ala Ser Tyr His Tyr Asn Thr Ile Thr Asp Cys Tyr Gln
    1685                1690                1695

Arg Leu Glu Phe Leu Gly Asp Ala Ile Leu Asp Tyr Leu Ile Thr
    1700                1705                1710

Lys His Leu Tyr Glu Asp Pro Arg Gln His Ser Pro Gly Val Leu
    1715                1720                1725

Thr Asp Leu Arg Ser Ala Leu Val Asn Asn Thr Ile Phe Ala Ser
    1730                1735                1740

Leu Ala Val Lys Tyr Asp Tyr His Lys Tyr Phe Lys Ala Val Ser
    1745                1750                1755

Pro Glu Leu Phe His Val Ile Asp Asp Phe Val Gln Phe Gln Leu
    1760                1765                1770

Glu Lys Asn Glu Met Gln Gly Met Asp Ser Glu Leu Arg Arg Ser
    1775                1780                1785

Glu Glu Asp Glu Glu Lys Glu Glu Asp Ile Glu Val Pro Lys Ala
    1790                1795                1800

Met Gly Asp Ile Phe Glu Ser Leu Ala Gly Ala Ile Tyr Met Asp
    1805                1810                1815

Ser Gly Met Ser Leu Glu Val Val Trp Gln Val Tyr Tyr Pro Met
    1820                1825                1830

Met Arg Pro Leu Ile Glu Lys Phe Ser Ala Asn Val Pro Arg Ser
    1835                1840                1845

Pro Val Arg Glu Leu Leu Glu Met Glu Pro Glu Thr Ala Lys Phe
    1850                1855                1860

Ser Pro Ala Glu Arg Thr Tyr Asp Gly Lys Val Arg Val Thr Val
    1865                1870                1875

Glu Val Val Gly Lys Gly Lys Phe Lys Gly Val Gly Arg Ser Tyr
    1880                1885                1890

Arg Ile Ala Lys Ser Ala Ala Ala Arg Arg Ala Leu Arg Ser Leu
    1895                1900                1905

Lys Ala Asn Gln Pro Leu Val Pro Asn Ser
    1910                1915

<210> SEQ ID NO 8
<211> LENGTH: 1916
<212> TYPE: PRT
<213> ORGANISM: Mus musculus

<400> SEQUENCE: 8

Leu Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

```
Asn Thr Gly Ser Gly Lys Thr Phe Ile Ala Val Leu Leu Thr Lys Glu
 65                  70                  75                  80

Leu Ala His Gln Ile Arg Gly Asp Leu Asn Pro His Ala Lys Arg Thr
                 85                  90                  95

Val Phe Leu Val Asn Ser Ala Asn Gln Val Ala Gln Gln Val Ser Ala
                100                 105                 110

Val Arg Thr His Ser Asp Leu Lys Val Gly Glu Tyr Ser Asp Leu Glu
                115                 120                 125

Val Asn Ala Ser Trp Thr Lys Glu Arg Trp Ser Gln Glu Phe Thr Lys
                130                 135                 140

His Gln Val Leu Ile Met Thr Cys Tyr Val Ala Leu Thr Val Leu Lys
145                 150                 155                 160

Asn Gly Tyr Leu Ser Leu Ser Asp Ile Asn Leu Leu Val Phe Asp Glu
                165                 170                 175

Cys His Leu Ala Ile Leu Asp His Pro Tyr Arg Glu Ile Met Lys Leu
                180                 185                 190

Cys Glu Ser Cys Pro Ser Cys Pro Arg Ile Leu Gly Leu Thr Ala Ser
                195                 200                 205

Ile Leu Asn Gly Lys Cys Asp Pro Glu Glu Leu Glu Glu Lys Ile Gln
210                 215                 220

Lys Leu Glu Arg Ile Leu Arg Ser Asp Ala Glu Thr Ala Thr Asp Leu
225                 230                 235                 240

Val Val Leu Asp Arg Tyr Thr Ser Gln Pro Cys Glu Ile Val Val Asp
                245                 250                 255

Cys Gly Pro Phe Thr Asp Arg Ser Gly Leu Tyr Glu Arg Leu Leu Met
                260                 265                 270

Glu Leu Glu Ala Ala Leu Asp Phe Ile Asn Asp Cys Asn Val Ala Val
                275                 280                 285

His Ser Lys Glu Arg Asp Ser Thr Leu Ile Ser Lys Gln Ile Leu Ser
290                 295                 300

Asp Cys Arg Ala Val Leu Val Val Leu Gly Pro Trp Cys Ala Asp Lys
305                 310                 315                 320

Val Ala Gly Met Met Val Arg Glu Leu Gln Lys Tyr Ile Lys His Glu
                325                 330                 335

Gln Glu Glu Leu His Arg Lys Phe Leu Leu Phe Thr Asp Thr Leu Leu
                340                 345                 350

Arg Lys Ile His Ala Leu Cys Glu Glu Tyr Phe Ser Pro Ala Ser Leu
                355                 360                 365

Asp Leu Lys Tyr Val Thr Pro Lys Val Met Lys Leu Leu Glu Ile Leu
                370                 375                 380

Arg Lys Tyr Lys Pro Tyr Glu Arg Gln Gln Phe Glu Ser Val Glu Trp
385                 390                 395                 400

Tyr Asn Asn Arg Asn Gln Asp Asn Tyr Val Ser Trp Ser Asp Ser Glu
                405                 410                 415

Asp Asp Asp Asp Glu Glu Ile Glu Glu Lys Glu Lys Pro Glu Thr
                420                 425                 430

Asn Phe Pro Ser Pro Phe Thr Asn Ile Leu Cys Gly Ile Ile Phe Val
                435                 440                 445

Glu Arg Arg Tyr Thr Ala Val Val Leu Asn Arg Leu Ile Lys Glu Ala
                450                 455                 460

Gly Lys Gln Asp Pro Glu Leu Ala Tyr Ile Ser Ser Asn Phe Ile Thr
465                 470                 475                 480
```

```
Gly His Gly Ile Gly Lys Asn Gln Pro Arg Ser Lys Gln Met Glu Ala
            485                 490                 495

Glu Phe Arg Lys Gln Glu Glu Val Leu Arg Lys Phe Arg Ala His Glu
        500                 505                 510

Thr Asn Leu Leu Ile Ala Thr Ser Val Val Glu Glu Gly Val Asp Ile
        515                 520                 525

Pro Lys Cys Asn Leu Val Val Arg Phe Asp Leu Pro Thr Glu Tyr Arg
        530                 535                 540

Ser Tyr Val Gln Ser Lys Gly Arg Ala Arg Ala Pro Ile Ser Asn Tyr
545                 550                 555                 560

Val Met Leu Ala Asp Thr Asp Lys Ile Lys Ser Phe Glu Glu Asp Leu
            565                 570                 575

Lys Thr Tyr Lys Ala Ile Glu Lys Ile Leu Arg Asn Lys Cys Ser Lys
            580                 585                 590

Ser Ala Asp Gly Ala Glu Ala Asp Val His Ala Gly Val Asp Asp Glu
            595                 600                 605

Asp Ala Phe Pro Pro Tyr Val Leu Arg Pro Asp Asp Gly Gly Pro Arg
        610                 615                 620

Val Thr Ile Asn Thr Ala Ile Gly His Ile Asn Arg Tyr Cys Ala Arg
625                 630                 635                 640

Leu Pro Ser Asp Pro Phe Thr His Leu Ala Pro Lys Cys Arg Thr Arg
                645                 650                 655

Glu Leu Pro Asp Gly Thr Phe Tyr Ser Thr Leu Tyr Leu Pro Ile Asn
                660                 665                 670

Ser Pro Leu Arg Ala Ser Ile Val Gly Pro Pro Met Asp Ser Val Arg
        675                 680                 685

Leu Ala Glu Arg Val Val Ala Leu Ile Cys Cys Glu Lys Leu His Lys
        690                 695                 700

Ile Gly Glu Leu Asp Glu His Leu Met Pro Val Gly Lys Glu Thr Val
705                 710                 715                 720

Lys Tyr Glu Glu Glu Leu Asp Leu His Asp Glu Glu Thr Ser Val
            725                 730                 735

Pro Gly Arg Pro Gly Ser Thr Lys Arg Arg Gln Cys Tyr Pro Lys Ala
            740                 745                 750

Ile Pro Glu Cys Leu Arg Glu Ser Tyr Pro Lys Pro Asp Gln Pro Cys
        755                 760                 765

Tyr Leu Tyr Val Ile Gly Met Val Leu Thr Thr Pro Leu Pro Asp Glu
        770                 775                 780

Leu Asn Phe Arg Arg Lys Leu Tyr Pro Pro Glu Asp Thr Thr Arg
785                 790                 795                 800

Cys Phe Gly Ile Leu Thr Ala Lys Pro Ile Pro Gln Ile Pro His Phe
                805                 810                 815

Pro Val Tyr Thr Arg Ser Gly Glu Val Thr Ile Ser Ile Glu Leu Lys
            820                 825                 830

Lys Ser Gly Phe Thr Leu Ser Gln Gln Met Leu Glu Leu Ile Thr Arg
            835                 840                 845

Leu His Gln Tyr Ile Phe Ser His Ile Leu Arg Leu Glu Lys Pro Ala
    850                 855                 860

Leu Glu Phe Lys Pro Thr Gly Ala Glu Ser Ala Tyr Cys Val Leu Pro
865                 870                 875                 880

Leu Asn Val Val Asn Asp Ser Gly Thr Leu Asp Ile Asp Phe Lys Phe
                885                 890                 895

Met Glu Asp Ile Glu Lys Ser Glu Ala Arg Ile Gly Ile Pro Ser Thr
```

```
                   900             905             910
Lys Tyr Ser Lys Glu Thr Pro Phe Val Phe Lys Leu Glu Asp Tyr Gln
            915             920             925
Asp Ala Val Ile Ile Pro Arg Tyr Arg Asn Phe Asp Gln Pro His Arg
            930             935             940
Phe Tyr Val Ala Asp Val Tyr Thr Asp Leu Thr Pro Leu Ser Lys Phe
945             950             955             960
Pro Ser Pro Glu Tyr Glu Thr Phe Ala Glu Tyr Lys Thr Lys Tyr
                965             970             975
Asn Leu Asp Leu Thr Asn Leu Asn Gln Pro Leu Leu Asp Val Asp His
            980             985             990
Thr Ser Ser Arg Leu Asn Leu Leu Thr Pro Arg His Leu Asn Gln Lys
            995             1000            1005
Gly Lys Ala Leu Pro Leu Ser Ser Ala Glu Lys Arg Lys Ala Lys
        1010            1015            1020
Trp Glu Ser Leu Gln Asn Lys Gln Ile Leu Val Pro Glu Leu Cys
        1025            1030            1035
Ala Ile His Pro Ile Pro Ala Ser Leu Trp Arg Lys Ala Val Cys
        1040            1045            1050
Leu Pro Ser Ile Leu Tyr Arg Leu His Cys Leu Leu Thr Ala Glu
        1055            1060            1065
Glu Leu Arg Ala Gln Thr Ala Ser Asp Ala Gly Val Gly Val Arg
        1070            1075            1080
Ser Leu Pro Val Asp Phe Arg Tyr Pro Asn Leu Asp Phe Gly Trp
        1085            1090            1095
Lys Lys Ser Ile Asp Ser Lys Ser Phe Ile Ser Ser Cys Asn Ser
        1100            1105            1110
Ser Leu Ala Glu Ser Asp Asn Tyr Cys Lys His Ser Thr Thr Val
        1115            1120            1125
Val Pro Glu His Ala Ala His Gln Gly Ala Thr Arg Pro Ser Leu
        1130            1135            1140
Glu Asn His Asp Gln Met Ser Val Asn Cys Lys Arg Leu Pro Ala
        1145            1150            1155
Glu Ser Pro Ala Lys Leu Gln Ser Glu Val Ser Thr Asp Leu Thr
        1160            1165            1170
Ala Ile Asn Gly Leu Ser Tyr Asn Lys Asn Leu Ala Asn Gly Ser
        1175            1180            1185
Tyr Asp Leu Val Asn Arg Asp Phe Cys Gln Gly Asn Gln Leu Asn
        1190            1195            1200
Tyr Phe Lys Gln Glu Ile Pro Val Gln Pro Thr Thr Ser Tyr Pro
        1205            1210            1215
Ile Gln Asn Leu Tyr Asn Tyr Glu Asn Gln Pro Lys Pro Ser Asn
        1220            1225            1230
Glu Cys Pro Leu Leu Ser Asn Thr Tyr Leu Asp Gly Asn Ala Asn
        1235            1240            1245
Thr Ser Thr Ser Asp Gly Ser Pro Ala Val Ser Thr Met Pro Ala
        1250            1255            1260
Met Met Asn Ala Val Lys Ala Leu Lys Asp Arg Met Asp Ser Glu
        1265            1270            1275
Gln Ser Pro Ser Val Gly Tyr Ser Ser Arg Thr Leu Gly Pro Asn
        1280            1285            1290
Pro Gly Leu Ile Leu Gln Ala Leu Thr Leu Ser Asn Ala Ser Asp
        1295            1300            1305
```

```
Gly Phe Asn Leu Glu Arg Leu Glu Met Leu Gly Asp Ser Phe Leu
1310                1315                1320

Lys His Ala Ile Thr Thr Tyr Leu Phe Cys Thr Tyr Pro Asp Ala
1325                1330                1335

His Glu Gly Arg Leu Ser Tyr Met Arg Ser Lys Lys Val Ser Asn
1340                1345                1350

Cys Asn Leu Tyr Arg Leu Gly Lys Lys Lys Gly Leu Pro Ser Arg
1355                1360                1365

Met Val Val Ser Ile Phe Asp Pro Val Asn Trp Leu Pro Pro
1370                1375                1380

Gly Tyr Val Val Asn Gln Asp Lys Ser Asn Ser Glu Lys Trp Glu
1385                1390                1395

Lys Asp Glu Met Thr Lys Asp Cys Leu Leu Ala Asn Gly Lys Leu
1400                1405                1410

Gly Glu Ala Cys Glu Glu Glu Asp Leu Thr Trp Arg Ala Pro
1415                1420                1425

Lys Glu Glu Ala Glu Asp Glu Asp Phe Leu Glu Tyr Asp Gln
1430                1435                1440

Glu His Ile Gln Phe Ile Asp Ser Met Leu Met Gly Ser Gly Ala
1445                1450                1455

Phe Val Arg Lys Ile Ser Leu Ser Pro Phe Ser Ala Ser Asp Ser
1460                1465                1470

Ala Tyr Glu Trp Lys Met Pro Lys Lys Ala Ser Leu Gly Ser Met
1475                1480                1485

Pro Phe Ala Ser Gly Leu Glu Asp Phe Asp Tyr Ser Ser Trp Asp
1490                1495                1500

Ala Met Cys Tyr Leu Asp Pro Ser Lys Ala Val Glu Glu Asp Asp
1505                1510                1515

Phe Val Val Gly Phe Trp Asn Pro Ser Glu Glu Asn Cys Gly Val
1520                1525                1530

Asp Thr Gly Lys Gln Ser Ile Ser Tyr Asp Leu His Thr Glu Gln
1535                1540                1545

Cys Ile Ala Asp Lys Ser Ile Ala Asp Cys Val Glu Ala Leu Leu
1550                1555                1560

Gly Cys Tyr Leu Thr Ser Cys Gly Glu Arg Ala Ala Gln Leu Phe
1565                1570                1575

Leu Cys Ser Leu Gly Leu Lys Val Leu Pro Val Ile Lys Arg Thr
1580                1585                1590

Ser Arg Glu Lys Ala Leu Asp Pro Ala Gln Glu Asn Gly Ser Ser
1595                1600                1605

Gln Gln Lys Ser Leu Ser Gly Ser Cys Ala Ser Pro Val Gly Pro
1610                1615                1620

Arg Ser Ser Ala Gly Lys Asp Leu Glu Tyr Gly Cys Leu Lys Ile
1625                1630                1635

Pro Pro Arg Cys Met Phe Asp His Pro Asp Ala Glu Lys Thr Leu
1640                1645                1650

Asn His Leu Ile Ser Gly Phe Glu Thr Phe Glu Lys Lys Ile Asn
1655                1660                1665

Tyr Arg Phe Lys Asn Lys Ala Tyr Leu Leu Gln Ala Phe Thr His
1670                1675                1680

Ala Ser Tyr His Tyr Asn Thr Ile Thr Asp Cys Tyr Gln Arg Leu
1685                1690                1695
```

| Glu | Phe | Leu | Gly | Asp | Ala | Ile | Leu | Asp | Tyr | Leu | Ile | Thr | Lys | His |
|---|---|---|---|---|---|---|---|---|---|---|---|---|---|---|
| 1700 | | | | | 1705 | | | | | 1710 | | | | |

| Leu | Tyr | Glu | Asp | Pro | Arg | Gln | His | Ser | Pro | Gly | Val | Leu | Thr | Asp |
|---|---|---|---|---|---|---|---|---|---|---|---|---|---|---|
| 1715 | | | | | 1720 | | | | | 1725 | | | | |

| Leu | Arg | Ser | Ala | Leu | Val | Asn | Asn | Thr | Ile | Phe | Ala | Ser | Leu | Ala |
|---|---|---|---|---|---|---|---|---|---|---|---|---|---|---|
| 1730 | | | | | 1735 | | | | | 1740 | | | | |

| Val | Lys | Tyr | Asp | Tyr | His | Lys | Tyr | Phe | Lys | Ala | Val | Ser | Pro | Glu |
|---|---|---|---|---|---|---|---|---|---|---|---|---|---|---|
| 1745 | | | | | 1750 | | | | | 1755 | | | | |

| Leu | Phe | His | Val | Ile | Asp | Asp | Phe | Val | Lys | Phe | Gln | Leu | Glu | Lys |
|---|---|---|---|---|---|---|---|---|---|---|---|---|---|---|
| 1760 | | | | | 1765 | | | | | 1770 | | | | |

| Asn | Glu | Met | Gln | Gly | Met | Asp | Ser | Glu | Leu | Arg | Arg | Ser | Glu | Glu |
|---|---|---|---|---|---|---|---|---|---|---|---|---|---|---|
| 1775 | | | | | 1780 | | | | | 1785 | | | | |

| Asp | Glu | Glu | Lys | Glu | Glu | Asp | Ile | Glu | Val | Pro | Lys | Ala | Met | Gly |
|---|---|---|---|---|---|---|---|---|---|---|---|---|---|---|
| 1790 | | | | | 1795 | | | | | 1800 | | | | |

| Asp | Ile | Phe | Glu | Ser | Leu | Ala | Gly | Ala | Ile | Tyr | Met | Asp | Ser | Gly |
|---|---|---|---|---|---|---|---|---|---|---|---|---|---|---|
| 1805 | | | | | 1810 | | | | | 1815 | | | | |

| Met | Ser | Leu | Glu | Val | Val | Trp | Gln | Val | Tyr | Tyr | Pro | Met | Met | Gln |
|---|---|---|---|---|---|---|---|---|---|---|---|---|---|---|
| 1820 | | | | | 1825 | | | | | 1830 | | | | |

| Pro | Leu | Ile | Glu | Lys | Phe | Ser | Ala | Asn | Val | Pro | Arg | Ser | Pro | Val |
|---|---|---|---|---|---|---|---|---|---|---|---|---|---|---|
| 1835 | | | | | 1840 | | | | | 1845 | | | | |

| Arg | Glu | Leu | Leu | Glu | Met | Glu | Pro | Glu | Thr | Ala | Lys | Phe | Ser | Pro |
|---|---|---|---|---|---|---|---|---|---|---|---|---|---|---|
| 1850 | | | | | 1855 | | | | | 1860 | | | | |

| Ala | Glu | Arg | Thr | Tyr | Asp | Gly | Lys | Val | Arg | Val | Thr | Val | Glu | Val |
|---|---|---|---|---|---|---|---|---|---|---|---|---|---|---|
| 1865 | | | | | 1870 | | | | | 1875 | | | | |

| Val | Gly | Lys | Gly | Lys | Phe | Lys | Gly | Val | Gly | Arg | Ser | Tyr | Arg | Ile |
|---|---|---|---|---|---|---|---|---|---|---|---|---|---|---|
| 1880 | | | | | 1885 | | | | | 1890 | | | | |

| Ala | Lys | Ser | Ala | Ala | Ala | Arg | Arg | Ala | Leu | Arg | Ser | Leu | Lys | Ala |
|---|---|---|---|---|---|---|---|---|---|---|---|---|---|---|
| 1895 | | | | | 1900 | | | | | 1905 | | | | |

| Asn | Gln | Pro | Gln | Val | Pro | Asn | Ser |
|---|---|---|---|---|---|---|---|
| 1910 | | | | | 1915 | | |

```
<210> SEQ ID NO 9
<211> LENGTH: 73
<212> TYPE: RNA
<213> ORGANISM: Homo sapiens

<400> SEQUENCE: 9
ugagguagua gguuguauag uuuuaggguc acacccacca cugggagaua acuauacaau      60
cuacugucuu acc                                                       73

<210> SEQ ID NO 10
<211> LENGTH: 37
<212> TYPE: RNA
<213> ORGANISM: Artificial sequence
<220> FEATURE:
<223> OTHER INFORMATION: Synthetic sequence

<400> SEQUENCE: 10
ugagguagua gguuguauag uuugaaaguu cacgauu                              37

<210> SEQ ID NO 11
<211> LENGTH: 39
<212> TYPE: RNA
<213> ORGANISM: Artificial sequence
<220> FEATURE:
<223> OTHER INFORMATION: Synthetic sequence

<400> SEQUENCE: 11
```

```
aaucgugaac uuucaaacua uacaaucuac ugucuuacc                          39

<210> SEQ ID NO 12
<211> LENGTH: 37
<212> TYPE: RNA
<213> ORGANISM: Artificial sequence
<220> FEATURE:
<223> OTHER INFORMATION: Synthetic sequence

<400> SEQUENCE: 12
ucgugaacuu ucaaacuaua caaccuacug ccucauu                            37

<210> SEQ ID NO 13
<211> LENGTH: 79
<212> TYPE: RNA
<213> ORGANISM: Artificial sequence
<220> FEATURE:
<223> OTHER INFORMATION: Synthetic sequence

<400> SEQUENCE: 13
ugagguagua gguuguauag uuugauuagg gucacaccca ccacugggag auucaaacua   60
uacaaccuac ugccucauu                                               79

<210> SEQ ID NO 14
<211> LENGTH: 42
<212> TYPE: RNA
<213> ORGANISM: Artificial sequence
<220> FEATURE:
<223> OTHER INFORMATION: Synthetic sequence

<400> SEQUENCE: 14
ugagguagua gguuguauag uuugauuagg gucacaccca cc                     42

<210> SEQ ID NO 15
<211> LENGTH: 37
<212> TYPE: RNA
<213> ORGANISM: Artificial sequence
<220> FEATURE:
<223> OTHER INFORMATION: Synthetic sequence

<400> SEQUENCE: 15
acugggagau ucaaacuaua caaccuacua ccucauu                            37

<210> SEQ ID NO 16
<211> LENGTH: 58
<212> TYPE: RNA
<213> ORGANISM: Artificial sequence
<220> FEATURE:
<223> OTHER INFORMATION: Synthetic sequence

<400> SEQUENCE: 16 uaaagucuu auaugcagg uagugguag ccaucuacug cauuacgagc acuuaaag        58

<210> SEQ ID NO 17
<211> LENGTH: 21
<212> TYPE: RNA
<213> ORGANISM: Artificial sequence
<220> FEATURE:
<223> OTHER INFORMATION: Synthetic sequence

<400> SEQUENCE: 17
uauacaaugu gcuagcuuuc u                                            21

<210> SEQ ID NO 18
<211> LENGTH: 21
```

```
<212> TYPE: RNA
<213> ORGANISM: Artificial sequence
<220> FEATURE:
<223> OTHER INFORMATION: Synthetic sequence

<400> SEQUENCE: 18
aaagcuagca cauuguauag u                                              21

<210> SEQ ID NO 19
<211> LENGTH: 9
<212> TYPE: PRT
<213> ORGANISM: Artificial sequence
<220> FEATURE:
<223> OTHER INFORMATION: Synthetic sequence

<400> SEQUENCE: 19

Cys Leu Asn Thr Gly Ser Gly Lys Thr
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic sequence

<400> SEQUENCE: 20

Cys Leu Asn Asp Gly Ser Gly Lys Thr
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic sequence

<400> SEQUENCE: 21

Cys Leu Asn Thr Pro Ser Gly Lys Thr
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic sequence

<400> SEQUENCE: 22

Cys Leu Ser Thr Gly Ser Gly Lys Thr
1               5

<210> SEQ ID NO 23
<211> LENGTH: 4
<212> TYPE: PRT
<213> ORGANISM: Artificial sequence
<220> FEATURE:
<223> OTHER INFORMATION: Synthetic sequence

<400> SEQUENCE: 23

Asp Glu Cys His
1
```